(12) United States Patent
Gutmann et al.

(10) Patent No.: US 12,280,060 B2
(45) Date of Patent: Apr. 22, 2025

(54) METHODS OF TREATING CANCER USING NEURONAL ACTIVITY INHIBITING AGENTS

(71) Applicants: David Gutmann, St. Louis, MO (US); Corina Anastasaki, St. Louis, MO (US)

(72) Inventors: David Gutmann, St. Louis, MO (US); Corina Anastasaki, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 18/069,317

(22) Filed: Dec. 21, 2022

(65) Prior Publication Data

US 2023/0190758 A1    Jun. 22, 2023

Related U.S. Application Data

(60) Provisional application No. 63/331,326, filed on Apr. 15, 2022, provisional application No. 63/292,023, filed on Dec. 21, 2021.

(51) Int. Cl.
| | | |
|---|---|---|
| *A61K 31/53* | (2006.01) | |
| *A61K 31/4192* | (2006.01) | |
| *A61K 38/48* | (2006.01) | |
| *A61P 35/00* | (2006.01) | |

(52) U.S. Cl.
CPC .......... *A61K 31/53* (2013.01); *A61K 31/4192* (2013.01); *A61K 38/4886* (2013.01); *A61P 35/00* (2018.01)

(58) Field of Classification Search
CPC ...................................................... A61P 35/00
See application file for complete search history.

(56) References Cited

U.S. PATENT DOCUMENTS

2019/0151239 A1    5/2019    Abrams et al.

FOREIGN PATENT DOCUMENTS

| WO | 2013183985 A1 | 12/2013 |
|---|---|---|
| WO | 2021173916 A1 | 9/2021 |

OTHER PUBLICATIONS

Hakami T. Neuropharmacology of Antiseizure Drugs. Neuropsychopharmacol Rep. Sep. 2021;41(3):336-351. (Year: 2021).*
Huguenard JR. Block of T-Type Ca(2+) Channels Is an Important Action of Succinimide Antiabsence Drugs. Epilepsy Curr. Mar. 2002;2(2):49-52. (Year: 2002).*
Mo et al. (2021) Humanized neurofibroma model from induced pluripotent stem cells delineates tumor pathogenesis and developmental origins. J Clin Invest 131, doi:10.1172/JCI139807.
Moosmang et al. (2001) Cellular expression and functional characterization of four hyperpolarization-activated pacemaker channels in cardiac and neuronal tissues. Eur J Biochem 268, 1646-1652, doi: 10.1046/i.1432-1327.2001.02036.x.
Morcos et al. (1996) Identification of neurofibromin mutants that exhibit allele specificity or increased Ras affinity resulting in suppression of activated ras alleles. Mol Cell Biol 16, 2496-2503, doi:10.1128/MCB.16.5.2496.
Muller et al. (2003) HCN channels are expressed differentially in retinal bipolar cells and concentrated at synaptic terminals. Eur J Neurosci 17, 2084-2096, doi:10.1046/j.1460-9568.2003.02634.x.
Omrani et al. (2015) HCN channels are a novel therapeutic target for cognitive dysfunction in Neurofibromatosis type 1. Mol Psychiatry 20, 1311-1321, doi: 10.1038/mp.2015.48.
Pan et al. (2018) Athymic mice reveal a requirement for T-cell-microglia interactions in establishing a microenvironment supportive of Nf1 low-grade glioma growth. Genes Dev 32, 491-496, doi:10.1101/gad.310797.117.
Pan et al. (2021) NF1 mutation drives neuronal activity-dependent initiation of optic glioma. Nature 594, 277-282, doi:10.1038/s41586-021-03580-6.
Pan et al. (2017) Ccl5 establishes an autocrine high-grade glioma growth regulatory circuit critical for mesenchymal glioblastoma survival. Oncotarget 8, 32977-32989, doi:10.18632/oncotarget.16516.
Peltonen et al. (1986) Collagens in neurofibromas and neurofibroma cell cultures. Ann N Y Acad Sci 486, 260-270, doi:10.1111/j.1749-6632.1986.tb48079.x.
Pinna et al. (2015) p.Arg1809Cys substitution in neurofibromin is associated with a distinctive NF1 phenotype without neurofibromas. Eur J Hum Genet 23, 1068-1071, doi:10.1038/ejhg.2014.243.
Pong et al. (2013) Reduced microglial CX3CR1 expression delays neurofibromatosis-1 glioma formation. Ann Neurol 73, 303-308, doi: 10.1002/ana.23813.
Poolos et al. (2006) Modulation of h-channels in hippocampal pyramidal neurons by p38 mitogen-activated protein kinase. J Neurosci v. 26(30), 7995-8003, doi:10.1523/JNEUROSCI.2069-06.2006.

(Continued)

*Primary Examiner* — Aurora M Fontainhas
*Assistant Examiner* — Jennifer A Benavides

(57) ABSTRACT

Among the various aspects of the present disclosure is the provision of methods for inhibiting neuronal activity in NF1 tumors. One aspect of the disclosure provides for a method of inhibiting tumor growth comprising administering a neuronal activity inhibiting agent to a subject in need thereof. Another aspect of the disclosure provides for a method of attenuating neuronal excitability, activity-regulated mitogen production, and tumor progression comprising administering a neuronal activity inhibiting agent to a subject in need thereof. Yet another aspect of the disclosure provides for a method of activating HCN channels in a subject comprising administering a neuronal activity inhibiting agent to a subject in need thereof. Yet another aspect of the disclosure provides for a method of treating brain or and nerve tumors in Neurofibromatosis type 1 (NF1) comprising administering a neuronal activity inhibiting agent to a subject in need thereof.

8 Claims, 79 Drawing Sheets
(31 of 79 Drawing Sheet(s) Filed in Color)

(56) References Cited

OTHER PUBLICATIONS

Poolos (2012) Hyperpolarization-Activated Cyclic Nucleotide-Gated (HCN) Ion Channelopathy in Epilepsy. In: Noebels JL, Avoli M, Rogawski MA, et al., editors. Jasper's Basic Mechanisms of the Epilepsies [Internet]. 4th edition. Bethesda (MD): National Center for Biotechnology Information (US). https://www.ncbi.nlm.nih.gov/books/NBK98137/.
Prada et al. (2013) Neurofibroma-associated macrophages play roles in tumor growth and response to pharmacological inhibition. Acta Neuropathol 125, 159-168, doi:10.1007/s00401-012-1056-7.
Riccioni (2010) Ivabradine: from molecular basis to clinical effectiveness. Adv Ther 27, 160- 167, doi: 10.1007/s12325-010-0014-9.
Rodriguez et al. (2012) Pathology of peripheral nerve sheath tumors: diagnostic overview and update on selected diagnostic problems. Acta Neuropathol 123, 295-319, doi: 10.1007/s00401-012-0954-z.
Rojnueangnit et al. (2015) High Incidence of Noonan Syndrome Features Including Short Stature and Pulmonic Stenosis in Patients carrying NF1 Missense Mutations Affecting p.Arg1809: Genotype-Phenotype Correlation. Hum Mutat 36, 1052-1063, doi:10.1002/humu.22832.
Santoro et al. (2020) Hyperpolarization-Activated Cyclic Nucleotide-Gated Channels as Drug Targets for Neurological Disorders. Annu Rev Pharmacol Toxicol 60, 109-131, doi:10.1146/annurev-pharmtox-010919-023356.
Sherekar et al. (2020) Biochemical and structural analyses reveal that the tumor suppressor neurofibromin (NF1) forms a high-affinity dimer. J Biol Chem 295, 1105-1119, doi:10.1074/jbc.RA119.010934.
Solga et al. (2015) RNA Sequencing of Tumor-Associated Microglia Reveals Ccl5 as a Stromal Chemokine Critical for Neurofibromatosis-1 Glioma Growth. Neoplasia 17, 776-788, doi:10.1016/j.neo.2015.10.002.
Toonen et al. (2016) NF1 germline mutation differentially dictates optic glioma formation and growth in neurofibromatosis-1. Hum Mol Genet 25, 1703-1713, doi:10.1093/hmg/ddw039.
Ungefroren et al. (2011) Interaction of tumor cells with the microenvironment. Cell Commun Signal 9, 18, doi:10.1186/1478-811X-9-18.
Vallee et al. (2012) Nf1 RasGAP inhibition of LIMK2 mediates a new cross-talk between Ras and Rho pathways. PLoS One 7, e47283, doi:10.1371/journal.pone.0047283.
Vasilyev et al. (2007) Direct inhibition of Ih by analgesic loperamide in rat DRG neurons. J Neurophysiol 97, 3713-3721, doi:10.1152/jn.00841.2006.
Venkataramani et al. (2019) Glutamatergic synaptic input to glioma cells drives brain tumour progression. Nature 573, 532-538, doi: 10.1038/s41586-019-1564-x.
Venkatesh et al. (2019) Electrical and synaptic integration of glioma into neural circuits. Nature 573, 539-545, doi:10.1038/s41586-019-1563-y.
Venkatesh et al. (2015) Neuronal Activity Promotes Glioma Growth through Neuroligin-3 Secretion. Cell 161, 803-816, doi:10.1016/j.cell.2015.04.012.
Venkatesh et al. (2017) Targeting neuronal activity-regulated neuroligin-3 dependency in high-grade glioma. Nature 549, 533-537, doi: 10.1038/nature24014.
Walker et al. (2018): Emerging therapeutic targets for neurofibromatosis type 1, Expert Opinion on Therapeutic Targets, DOI: 10.1080/14728222.2018.1465931.
Wang et al. (2011) Valosin-containing protein and neurofibromin interact to regulate dendritic spine density. J Clin Invest 121, 4820-4837, doi:10.1172/JCI45677.
Wang et al. (2005) Sensory neurons from Nf1 haploinsufficient mice exhibit increased excitability. J Neurophysiol 94, 3670-3676, doi:10.1152/jn.00489.2005.
Widemann et al. (2014) Phase II trial of pirfenidone in children and young adults with neurofibromatosis type 1 and progressive plexiform neurofibromas. Pediatr Blood Cancer 61, 1598-1602, doi:10.1002/pbc.25041.
Yang et al. (2006) Nf1+/− mast cells induce neurofibroma like phenotypes through secreted TGF-beta signaling. Hum Mol Genet 15, 2421-2437, doi:10.1093/hmg/ddl165.
Yang et al. (2008) Nf1-dependent tumors require a microenvironment containing Nf1+/− and c-kit-dependent bone marrow. Cell 135, 437-448, doi:10.1016/j.cell.2008.08.041.
Yu et al. (2020) PIK3CA variants selectively initiate brain hyperactivity during gliomagenesis. Nature 578, 166-171, doi:10.1038/s41586-020-1952-2.
Zhu et al. (2001) Ablation of NF1 function in neurons induces abnormal development of cerebral cortex and reactive gliosis in the brain. Genes Dev 15, 859-876, doi:10.1101/gad.862101.
Anastasaki et al. (2020) Human iPSC-Derived Neurons and Cerebral Organoids Establish Differential Effects of Germline NF1 Gene Mutations. Stem Cell Reports 14, 541-550, doi:10.1016/j.stemcr.2020.03.007.
Anastasaki et al. (2015) Elucidating the impact of neurofibromatosis-1 germline mutations on neurofibromin function and dopamine-based learning. Hum Mol Genet 24, 3518-3528, doi:10.1093/hmg/ddv103.
Atit et al. (1999) The Nf1 tumor suppressor regulates mouse skin wound healing, fibroblast proliferation, and collagen deposited by fibroblasts. J Invest Dermatol 112, 835-842, doi: 10.1046/j.1523-1747.1999.00609.x.
Badalamente et al. (2007) Efficacy and safety of injectable mixed collagenase subtypes in the treatment of Dupuytren's contracture. J Hand Surg Am 32, 767-774, doi:10.1016/j.jhsa.2007.04.002.
Bajenaru et al. (2002) Astrocyte-specific inactivation of the neurofibromatosis 1 gene (NF1) is insufficient for astrocytoma formation. Mol Cell Biol 22, 5100-5113, doi:10.1128/MCB.22.14.5100-5113.2002.
Bajenaru et al. (2003) Optic nerve glioma in mice requires astrocyte Nf1 gene inactivation and Nf1 brain heterozygosity. Cancer Res 63, 8573-8577.
Blaszczyk et al. (2010) Efficacy, safety, and potential of extended-release lamotrigine in the treatment of epileptic patients. Neuropsychiatric Disease and Treatment, v. 6, pp. 145-150.
Brannan et al. (1994) Targeted disruption of the neurofibromatosis type-1 gene leads to developmental abnormalities in heart and various neural crest-derived tissues. Genes Dev 8, 1019-1029, doi:10.1101/gad.8.9.1019.
Brosseau et al. (2021) Human cutaneous neurofibroma matrisome revealed by single-cell RNA sequencing. Acta Neuropathol Commun 9, 11, doi:10.1186/s40478-020-01103-4.
Brossier et al. (2021) Temporal, spatial, and genetic constraints contribute to the patterning and penetrance of murine neurofibromatosis-1 optic glioma. Neuro Oncol 23, 625-637, doi:10.1093/neuonc/noaa237.
Buckingham et al. (2011) Glutamate release by primary brain tumors induces epileptic activity. Nat Med 17, 1269-1274, doi:10.1038/nm.2453.
Campbell et al. (2015) GABAergic disinhibition and impaired KCC2 cotransporter activity underlie tumor-associated epilepsy. Glia 63, 23-36, doi:10.1002/glia.22730.
Campbell et al. (2012) Human glioma cells induce hyperexcitability in cortical networks. Epilepsia 53, 1360-1370, doi:10.1111/j.1528-1167.2012.03557.x.
Chen et al. (2010) Nf1-/- Schwann cell-conditioned medium modulates mast cell degranulation by c-Kit-mediated hyperactivation of phosphatidylinositol 3-kinase. Am J Pathol 177, 3125-3132, doi:10.2353/ajpath.2010.100369.
Chen et al. (2014) Cells of origin in the embryonic nerve roots for NF1-associated plexiform neurofibroma. Cancer Cell 26, 695-706, doi:10.1016/j.ccell.2014.09.009.
Chen et al. (2019) Spatiotemporal Loss of NF1 in Schwann Cell Lineage Leads to Different Types of Cutaneous Neurofibroma Susceptible to Modification by the Hippo Pathway. Cancer Discov 9, 114-129, doi: 10.1158/2159-8290.CD-18-0151.

(56) References Cited

OTHER PUBLICATIONS

Chi et al. (1993) Isolation and age-related characterization of mouse Schwann cells from dorsal root ganglion explants in type I collagen gels. J Neurosci Res 35, 183-187, doi:10.1002/jnr.490350208.

Cho et al. (2009) Inflammation-induced increase in hyperpolarization-activated, cyclic nucleotide-gated channel protein in trigeminal ganglion neurons and the effect of buprenorphine. Neuroscience 162, 453-461, doi:10.1016/j.neuroscience.2009.04.063.

CTF Conference Proceedings (2015). Children's Tumor Foundation NF Conference "The Path Forward", 113 pages.

Daginakatte et al. (2007) Neurofibromatosis-1 (Nf1) heterozygous brain microglia elaborate paracrine factors that promote Nf1-deficient astrocyte and glioma growth. Hum Mol Genet 16, 1098-1112, doi:10.1093/hmg/ddm059.

Daginakatte et al. (2008) Increased c-Jun-NH2-kinase signaling in neurofibromatosis-1 heterozygous microglia drives microglia activation and promotes optic glioma proliferation. Cancer Res 68, 10358-10366, doi:10.1158/0008-5472.CAN-08-2506.

D'Angelo et al. (2006) A novel bipartite phospholipid-binding module in the neurofibromatosis type 1 protein. EMBO Rep 7, 174-179, doi:10.1038/sj.embor.7400602.

Deraredj Nadim et al. (2016) Physical interaction between neurofibromin and serotonin 5-HT6 receptor promotes receptor constitutive activity. Proc Natl Acad Sci U S A 113, 12310-12315, doi: 10.1073/pnas.1600914113.

Evans et al. (2010) Birth incidence and prevalence of tumor-prone syndromes: estimates from a UK family genetic register service. Am J Med Genet A 152A, 327-332, doi:10.1002/ajmg.a.33139.

Ferner et al. (2013) Neurofibromatosis type 1 (NF1): diagnosis and management. Handb Clin Neurol 115, 939-955, doi:10.1016/B978-0-444-52902-2.00053-9.

Fletcher et al. (2019) Cxcr3-expressing leukocytes are necessary for neurofibroma formation in mice. JCI Insight 4, doi:10.1172/jci.insight.98601.

Fletcher et al. (2019) STAT3 inhibition reduces macrophage number and tumor growth in neurofibroma. Oncogene 38, 2876-2884, doi:10.1038/s41388-018-0600-x.

Fletcher et al. (2020) After Nf1 loss in Schwann cells, inflammation drives neurofibroma formation. Neurooncol Adv 2, 123-i32, doi:10.1093/noajnl/vdz045.

Friedman (1999) Epidemiology of neurofibromatosis type 1. Am J Med Genet 89, 1-6.

Gorzalczany et al. (2017) Mast cells are directly activated by contact with cancer cells by a mechanism involving autocrine formation of adenosine and autocrine/paracrine signaling of the adenosine A3 receptor. Cancer Lett 397, 23-32, doi:10.1016/j.canlet.2017.03.026.

Guo et al. (2020) Midkine activation of CD8(+) T cells establishes a neuron-immune-cancer axis responsible for low-grade glioma growth. Nat Commun 11, 2177, doi:10.1038/s41467-020-15770-3.

Guo et al. (2019) Genetic and genomic alterations differentially dictate low-grade glioma growth through cancer stem cell-specific chemokine recruitment of T cells and microglia. Neuro Oncol 21, 1250-1262, doi:10.1093/neuonc/noz080.

Hegedus et al. (2008) Preclinical cancer therapy in a mouse model of neurofibromatosis-1optic glioma. Cancer Res 68, 1520-1528, doi:10.1158/0008-5472.CAN-07-5916.

Herrmann et al. (2015) HCN channels—modulators of cardiac and neuronal excitability. Int J Mol Sci 16, 1429-1447, doi:10.3390/ijms16011429.

Hu et al. (2005) Distinct epigenetic changes in the stromal cells of breast cancers. Nat Genet 37, 899-905, doi:10.1038/ng1596.

Jacks et al. (1994) Tumour predisposition in mice heterozygous for a targeted mutation in Nf1. Nat Genet 7, 353-361, doi:10.1038/ng0794-353.

Jett et al. (2010) Clinical and genetic aspects of neurofibromatosis 1. Genet Med 12, 1-11, doi:10.1097/GIM.0b013e3181bf15e3.

John Lin et al. (2017) Identification of diverse astrocyte populations and their malignant analogs. Nat Neurosci 20, 396-405, doi:10.1038/nn.4493.

Joyce (2005) Therapeutic targeting of the tumor microenvironment. Cancer Cell 7, 513-520, doi:10.1016/j.ccr.2005.05.024.

Kazmierska-Grebowska et al. (2021) Lamotrigine Attenuates Neuronal Excitability, Depresses GABA Synaptic Inhibition, and Modulates Theta Rhythms in Rat Hippocampus. International Journal of Molecular Sciences, 22(24), 13604.

Keilhoff et al. (2003) Bio-compatibility of type I/III collagen matrix for peripheral nerve reconstruction. Biomaterials 24, 2779-2787, doi: 10.1016/s0142-9612(03)00084-x.

Kharouf et al. (2020) Testing broad-spectrum and isoform-preferring HCN channel blockers for anticonvulsant properties in mice. Epilepsy Res 168, 106484, doi:10.1016/j.eplepsyres.2020.106484.

Kim et al. (2015) Neurofibromatosis. Philanthropy Advisory Service "A Giving Smarter Guide", 32 pages.

Kitano et al. (1992) Effects of several growth factors on cultured neurofibroma cells. J Dermatol Sci 3, 137-144, doi:10.1016/0923-1811(92)90027-9.

Koczkowska et al. (2018) Genotype-Phenotype Correlation in NF1: Evidence for a More Severe Phenotype Associated with Missense Mutations Affecting NF1 Codons 844-848. Am J Hum Genet 102, 69-87, doi:10.1016/j.ajhg.2017.12.001.

Le et al. (2009) Cell of origin and microenvironment contribution for NF1-associated dermal neurofibromas. Cell Stem Cell 4, 453-463, doi:10.1016/j.stem.2009.03.017.

Lee et al. (2012) Innate neural stem cell heterogeneity determines the patterning of glioma formation in children. Cancer Cell 22, 131-138, doi:10.1016/j.ccr.2012.05.036.

Li et al. (2016) Mice with missense and nonsense NF1 mutations display divergent phenotypes compared with human neurofibromatosis type I. Dis Model Mech 9, 759-767, doi:10.1242/dmm.025783.

Liao et al. (2018) Contributions of inflammation and tumor microenvironment to neurofibroma tumorigenesis. J Clin Invest 128, 2848-2861, doi:10.1172/JCI99424.

Mashour et al. (2001) The angiogenic factor midkine is aberrantly expressed in NF1-deficient Schwann cells and is a mitogen for neurofibroma-derived cells. Oncogene 20, 97-105, doi:10.1038/sj.onc.1204026.

\* cited by examiner

METHODS OF TREATING CANCER USING NEURONAL ACTIVITY INHIBITING AGENTS

CROSS-REFERENCE TO RELATED APPLICATIONS

This application claims priority from U.S. Provisional Application Ser. No. 63/292,023 filed on 21 Dec. 2021 and 63/331,326 filed on 15 Apr. 2022, which are incorporated herein by reference in their entireties.

STATEMENT REGARDING FEDERALLY SPONSORED RESEARCH OR DEVELOPMENT

This invention was made with government support under NS097211 and CA233164 awarded by the National Institutes of Health. The government has certain rights in the invention.

MATERIAL INCORPORATED-BY-REFERENCE

Not applicable.

FIELD

The present disclosure generally relates to neuronal activity inhibiting agents for treating nervous system tumors.

SUMMARY

Among the various aspects of the present disclosure is the provision of methods for inhibiting neuronal activity in Neurofibromatosis type 1 (NF1)-related tumors. An aspect of the present disclosure provides for a method of inhibiting tumor growth in a subject in need thereof comprising administering a neuronal activity inhibiting agent to the subject. Another aspect of the present disclosure provides for a method of attenuating neuronal hyperexcitability or hyperpolarization-activated cyclic nucleotide-gated (HCN) channel dysregulation in a subject in need thereof comprising administering to the subject an effective amount of a neuronal activity inhibiting agent. Yet another aspect of the present disclosure provides for a method of activating HCN channels in a subject comprising administering a neuronal activity inhibiting agent to a subject in need thereof. Yet another aspect of the present disclosure provides for a method of treating brain and/or nerve tumors in NF1 comprising administering a neuronal activity inhibiting agent to a subject in need thereof.

In some embodiments, the neuronal activity inhibiting agent is an HCN channel activation agent. In some embodiments, the neuronal activity inhibiting agent is an FDA-approved drug already in use for treating children with epilepsy and related disorders In some embodiments, the neuronal activity inhibiting agent is an anti-epileptic drug (AED). In some embodiments, the HCN channel activating agent is an HCN channel agonist. In some embodiments, the neuronal activity inhibiting agent is an HCN channel activating agent selected from lamotrigine and rufinamide. In some embodiments, the neuronal activity inhibiting agent is selected from VALIUM® (diazepam); TOPAMAX® (topiramate); ZONEGRAN® (zonisamide); TEGRETOL® (carbamazepine); TRILEPTAL® (oxcarbazepine); APTIOM® (eslicarbazepine); EPITOL® (carbamazepine); DEPAKOTE® (divalproex sodium); LYRICA® (pregabalin); NEURONTIN® (gabapentin); DILANTIN® (phenytoin); VIMPAT® (lacosamide); KEPPRA® (levetiracetam); LAMICTAL® (lamotrigine); GABITRIL® (tiagabine); MEBARAL® (mephobarbital); LUMINAL® (phenobarbital); DIAMOX® (acetazolamide); CARBATROL® (carbamazepine); EQUETRO® (carbamazepine); OXTELLAR XR® (oxcarbazepine); CARNEXIV® (carbamazepine); DEPAKENE® (valproic acid); STAVZOR® (valproic acid); DEPACON® (valproic acid); HORIZANT® (gabapentin enacarbil); GRALISE® (gabapentin); GABORONE® (gabapentin); SABRIL® (vigabatrin); FANATREX™ (gabapentin); DIACOMIT® (stiripentol); PHENYTEK® (phenytoin); PEGANONE® (phenytoin); MESANTOIN® (mephenytoin); CEREBYX® (fosphenytoin); FINETELPLAR (fenfluramine); EPIDIOLEX® (cannabidiol); POTIGA™ (ezogabine); TRIDIONE® (trimethadione); BRIVIACT® (brivaracetam); SPRITAM® (levetiracetam); ROWEEPRA® (levetiracetam); ZARONTIN® (ethosuximide); CELONTIN® (methsuximide); FYCOMPA® (perampanel); KLONOPIN® (clonazepam); VERSED® (midazolam); FELBATOL® (felbamate); XCOPRI® (cenobamate); MYSOLINE® (primidone); ONFI® (clobazam); ATIVAN® (lorazepam); TRANXENE-T® (clorazepate); BANZEL® (rufinamide); or TROKENDI XR® (topiramate).

In some embodiments, the subject has Neurofibromatosis type 1 (NF1) optic pathway gliomas or peripheral nerve sheath tumors (neurofibromas). In some embodiments, the subject has Optic Pathway Glioma (OPG) in NF1. In some embodiments, the subject has NF1-mutant CNS neurons. In some embodiments, the subject has a brain, nerve sheath or spinal cord tumor. In some embodiments, the brain, peripheral nerve sheath, or spinal cord tumor is selected from the group consisting of glioma; astrocytoma; brainstem glioma; glioblastoma (GBM); juvenile pilocytic astrocytoma (JPA); plexiform neurofibroma; neurofibroma; optic pathway glioma; malignant peripheral nerve sheath tumor; atypical neurofibromatous neoplasm of uncertain biologic potential (ANNUBP). In some embodiments, the astrocytoma is selected from grade 1 pilocytic astrocytoma, grade 2 low-grade astrocytoma, grade 3 anaplastic astrocytoma, or grade 4 glioblastoma (GBM). In some embodiments, the glioma is selected from brainstem glioma, mixed glioma, optic pathway glioma, or low-grade glioma. In some embodiments, the neuronal activity inhibiting agent is an amount sufficient to reduce or inhibit neuronal activity, activate HCN channels, substantially inhibit tumor growth or cancer proliferation, slow the progress of tumor growth or cancer proliferation, or limit the development of tumor growth or cancer proliferation.

In some embodiments, the subject has Neurofibromatosis type 1 (NF1) and an NF1 gene mutation selected from c.1149 C>A, p.Cys381X; c.2041 C>T, pArg681X; or c.6619 C>T, p.Gln2207X. In some embodiments, the methods comprise administering the neuronal activity inhibiting agent to the subject reduces neuronal excitability, paracrine factor production or secretion, or Schwann cell proliferation in the subject. In some embodiments, the neuronal activity inhibiting agent reduces excitability or paracrine factor production of retinal ganglion cells (RGCs), sensory neurons, or dorsal root ganglion cells (DRGs). In some embodiments, the methods comprise administering the neuronal activity inhibiting agent to the subject reduces Nlgn3, midkine, or Col1a2 transcript or protein expression or secretion in the subject. In some embodiments, the methods further comprise administering an effective amount of a COL1A2 inhibitor to the subject. In some embodiments, the COL1A2 inhibitor is collagenase.

DESCRIPTION OF THE DRAWINGS

The patent or application file contains at least one drawing executed in color. Copies of this patent or patent application publication with color drawing(s) will be provided by the Office upon request and payment of the necessary fee.

Those of skill in the art will understand that the drawings, described below, are for illustrative purposes only. The drawings are not intended to limit the scope of the present teachings in any way.

FIG. 1A is a table showing the summary of litters of Arg1809Cys Nf1 heterozygous mouse intercrosses. FIG. 1B is a bar graph showing weights of male and female Arg1809Cys Nf1-mutant mice are similar to WT littermates at 1 month of age. n=4 for all groups. Data are represented as means±SEM. One-way ANOVA with Bonferroni post-test correction. p values were not significant (ns).

FIG. 2A is a table showing incidence of optic pathway glioma (OPG) in NF1 patients harboring the c.5425C>T NF1 germline mutation. (a) 44, (b) 45, (c) 40. FIG. 2B includes representative images of dissected optic nerves from control (Nf1$^{f/f}$; CTL) and Nf1-mutant mice harboring conditional somatic Nf1 inactivation in neuroglial progenitors (Nf1$^{f/1809}$; GFAP-Cre, F1809C; Nf1$^{f/neo}$; GFAP-Cre, Nf1-OPG). Whereas Nf1-OPG mice form OPGs (red asterisk), CTL and F1809C mice do not. The number of mice that formed OPGs is shown in each panel. Scale bar: 1 mm. FIG. 2C is a graph demonstrating the relationship between optic nerve volumes and Ki67$^+$ cells in CTL, F1809C, and Nf1-OPG optic nerves. n=6 for all groups. FIG. 2D includes images and bar graphs showing Ki67, Iba1, CD3, and GFAP immunostaining of optic nerves in CTL, F1809C, and Nf1-OPG mice. Scale bars, 50 μm. (Ki67: CTL n=8, F1809C n=7, Nf1-OPG n=4, P<0.0001; Iba1: CTL n=5, F1809C n=4, Nf1-OPG n=4, P=0.0023; CD3: CTL n=4, F1809C n=4, Nf1-OPG n=4, P=0.0003). Data are represented as means±SEM. One-way ANOVA with Dunnett's post-test correction.

FIG. 3A and FIG. 3B include graphs and traces showing Nf1$^{+/neo}$, but not Nf1$^{+/1809}$, RGC neuron activity (AP firing rates), as measured by (FIG. 3A) multi-electrode arrays (CTL n=27, Nf1$^{+/neo}$ n=15, P=0.0012, Nf1$^{+/1809}$ n=4), or (FIG. 3B) calcium imaging (CTL n=24, Nf1$^{+/neo}$ n=13, P<0.0001, Nf1$^{+/1809}$ n=6), is elevated relative to WT RGC neurons. Each dot represents (FIG. 3A) the average of a minimum of three technical replicates for a single animal, or (FIG. 3B) a single neuron. Right panels depict representative (FIG. 3A) spike plots of entire multi-electrode array well recordings over 30 s and (FIG. 3B) traces of neuronal activity represented as fluorescence differentials over 3 min. FIG. 3C includes a graph and traces showing the amplitudes of action potentials are similar in Nf1$^{+/neo}$ and Nf1$^{+/1809}$ RGC neurons relative to WT controls (CTL n=4, Nf1$^{+/neo}$ n=4, Nf1$^{+/1809}$ n=3). ns not significant. Right panels: representative traces of action potentials recorded over 3 ms (gray). The average of the action potentials is shown in black. One-way ANOVA with Dunnett's post-test correction (FIG. 3B and FIG. 3C), or (FIG. 3A) two-tailed unpaired Student's t test.

FIG. 4 includes images showing immunocharacterization of retinal ganglion cells (RGCs; RPBML$^+$, Brn3a$^+$, TUJ-1$^+$), hippocampal neurons (Glutamate Synthetase$^+$, GAD65$^+$, TUJ-1$^+$) and dorsal root ganglia (DRG) neurons (peripherin$^+$, Islet-1$^+$, TUJ-1$^+$). Scale bar, 100 μm. Immunostaining of primary neurons was repeated independently 4 times with similar results.

FIG. 5A includes bar graphs showing Neuroligin-3 transcript (Nlgn3) relative expression (CTL n=4, Nf1$^{+/neo}$ n=4, O.N. P=0.0016, retina P=0.0008, Nf1$^{+/1809}$ n=3, ns) is increased in Nf1$^{+/neo}$ optic nerves (ON) and retinae relative to WT and Nf1$^{+/1809}$ counterparts. FIG. 5B includes bar graphs showing Nlgn3 (CTL n=4, Nf1$^{+/neo}$ n=4, Nf1$^{+/1809}$ n=3; P=0.0046) and Mdk (CTL n=7, Nf1$^{+/neo}$ n=6, Nf1$^{+/1809}$ n=5; P<0.0001) transcript relative expression is increased in Nf1$^{+/neo}$ retinal ganglion cell (RGC) neurons relative to WT and Nf1$^{+/1809}$ RGCs. FIG. 5C includes images and a bar graph showing soluble neuroligin-3 (s-Nlgn3; CTL n=13, Nf1$^{+/neo}$ n=6, P<0.0001, Nf1$^{+/1809}$ n=7, ns) is increased in Nf1$^{+/neo}$ optic nerves (ON) and retinae relative to WT and Nf1$^{+/1809}$ counterparts. β-actin was used as a loading control. FIG. 5D includes bar graphs showing Midkine transcript (Mdk) relative expression is increased in whole optic nerves and retinae from Nf1$^{+/neo}$ mice relative to WT controls and Nf1$^{+/1809}$ mice. n=3 for all groups. O.N. Mdk R.E., P=0.0002; retinal Mdk R.E., P=0.0123. FIG. 5E is a bar graph and FIG. 5F contains images showing Midkine protein expression is elevated in (FIG. 5E) the Nf1$^{+/neo}$ conditioned media (CM) from RGCs in vitro (n=7 for all groups; P<0.0001), and (FIG. 5F) the RGC layer of Nf1$^{+/neo}$ mice relative to WT and Nf1$^{+/1809}$ mice. Scale bar, 50 μm. Dotted lines and arrow highlight the RGC layer. Data are represented as means±SEM. One-way ANOVA with Dunnett's post-test correction (FIG. 5A-5E).

FIG. 6 contains images showing Midkine expression is increased in Nf1$^{+/R681X}$ mutant RGCs relative to controls. Scale bar, 50 μm. Immunostaining of mouse retinae was repeated on a minimum of 3 independent animals per genotype with similar results.

FIG. 7A and FIG. 7B are bar graphs showing Midkine (FIG. 7A) transcript (Mdk) and (FIG. 7B) protein expression are increased in hippocampal neurons from Nf1$^{+/neo}$ mice (n=8; Mdk R.E. p=0.0008; Midkine p<0.0001) relative to WT controls (n=7) and Nf1$^{+/1809}$ mice (n=3). FIG. 7C is a bar graph showing hippocampal neuron activity, as measured by action potential (AP) firing rates, is increased in Nf1$^{+/neo}$ (n=4; p=0.025) relative to WT (n=8) and Nf1$^{+/1809}$ (n=4) neurons.

FIG. 8 includes images showing immunocharacterization of excitatory (Glutamate Synthetase$^+$, NeuN$^+$, TUJ-1$^+$) and inhibitory (GABA$^+$, GAD67+, TUJ-1+) hiPSC-derived CNS neurons. Scale bar, 100 μm. Immunostaining of hiPSC-derived neurons was repeated independently 3 times with similar results.

FIG. 9 is a bar graph showing Midkine expression is elevated in human CNS excitatory NF1-C383X (P=0.0004), NF1-R681X (P<0.0001) and NF1-E2207X (P<0.0001) mutant neurons, but not NF1-R1809C neurons, relative to controls (CTL). n=3 for all groups. One-way ANOVA with Dunnett's post-test correction.

FIG. 10 is a bar graph showing Midkine expression is increased in human CNS inhibitory (GABAergic) NF1-C383X, NF1-R681X and NF1-E2207X, but not in NF1-R1809C, mutant neurons relative to controls (CTL). n=3 for all groups, p=0.0002. Data are represented as means±SEM. One-way ANOVA with Dunnett's post-test correction.

FIG. 11A shows a representative summary of multi-electrode array recordings of WT, $Nf1^{+/neo}$ and $Nf1^{+/1809}$ RGCs illustrating action potentials detected by each electrode over a period of 5 minutes. FIG. 11B-FIG. 11D are bar graphs showing Adam-10 (Adam10) transcript expression is increased in $Nf1^{+/neo}$ relative to WT and $Nf1^{+/1809}$ optic nerves, retinae and RGCs. (FIG. 11B) n=4 for all groups, p=0.0010; (FIG. 11C) n=4 for all groups, p=0.0161; (FIG. 11D) WT n=5, $Nf1^{+/neo}$, $Nf1^{+/1809}$ n=4, p=0.0007. FIG. 11E is a bar graph showing Nlgn3 transcript expression is similar in $Nf1^{+/neo}$, $Nf1^{+/1809}$ and WT DRG neurons. n=4 for all groups. FIG. 11F and FIG. 11G are bar graphs showing that Midkine (Mdk) (FIG. 11G) RNA and (FIG. 11F) protein expression are not increased in Nf1-mutant DRG neurons relative to WT controls. FIG. 11F, n=8 for all groups, p=0.007. FIG. 11G, WT n=8, $Nf1^{+/neo}$ n=8, $Nf1^{+/1809}$ n=4, p=0.0104. FIG. 11H is a bar graph showing Ccl4 expression is increased similarly in WT (n=4) and Arg1809Cys Nf1-mutant (n=3) hippocampal neurons following midkine treatment. FIG. 11I is a bar graph showing Ccl5 is similarly elevated in WT (n=3) and Arg1809Cys Nf1-mutant (n=3) hippocampal neurons following Ccl4 treatment. Data are represented as means±SEM. (FIG. 11B-FIG. 11I) One-way ANOVA with (FIG. 11B-FIG. 11G) Dunnett's post-test correction.

FIG. 12A and FIG. 12B include bar graphs and traces showing tetrodotoxin (TTX; 1 μM) reduced the AP firing rate of $Nf1^{+/neo}$ RGC neurons relative to controls, as measured by (FIG. 12A) multi-electrode arrays (vehicle n=5, TTX n=7; P=0.0003) and (FIG. 12B) calcium imaging (vehicle n=17, TTX n=17; P<0.0001). Right panels: representative (FIG. 12A) spike plots of entire multi-electrode array well recordings over 30 s, and (FIG. 12B) traces of neuronal activity over 3 min. FIG. 12C is a bar graph showing TTX reduced midkine secretion by $Nf1^{+/neo}$ RGC neurons. n=5 for all groups (P=0.0046). Data are represented as means±SEM. (FIG. 12A-FIG. 12B) two-tailed unpaired and (FIG. 12C) two-tailed paired Student's t test.

FIG. 13A and FIG. 13B are bar graphs showing (FIG. 13A) Neuroligin (Nlgn3; P<0.0001) but not (FIG. 13B) midkine (Mdk; ns not significant) transcript relative expression is decreased in retinae of $Nf1^{+/neo}$ mice following dark-rearing from 4 to 8 weeks. Light-reared n=5, dark-reared n=8. FIG. 13C includes images showing Midkine expression is not reduced in the RGC layer (dotted lines, black arrow) or retinae in 8-week-old $Nf1^{+/neo}$ mice following dark-rearing from 4 to 8 weeks. Light-reared n=5, dark-reared n=8. Data are represented as means±SEM, unpaired two-tailed Student's t test. P values are indicated within each panel.

FIG. 14 includes bar graphs showing Hcn1-4 RNA expression is not different in Nf1-mutant RGC neurons relative to WT controls. n=4 for all groups. Data are represented as means±SEM. One-way ANOVA with Bonferroni post-test correction.

FIG. 15A and FIG. 15B includes graphs and traces showing RGC activity is reduced following 200 μM lamotrigine (LTR) treatment, as measured by (FIG. 15A) multi-electrode array (vehicle n=6; LTR n=6; P<0.0001), or (FIG. 15B) calcium imaging (vehicle n=18; LTR n=18; P<0.0001). Right panels: representative (FIG. 15A) spike plots of entire multi-electrode array well recordings over 30 s, and (FIG. 15B) traces of neuronal activity over 3 min. FIG. 15C is a bar graph showing Nlgn3 relative expression is unaltered in retinae of $Nf1^{+/neo}$ mice following LTR treatment in vivo. n=5 for all groups. Data are represented as means±SEM, unpaired two-tailed Student's t test.

FIG. 16A is a bar graph showing Adam10 transcript expression is unchanged in retinae of 12 week-old $Nf1^{+/neo}$ mice following in vivo lamotrigine (LTR; 200 μM) treatment. n=5 for all groups. FIG. 16B includes bar graphs showing Mdk, Adam10, and Nlgn3 transcript expression in the optic nerves (O.N.) of 12-week-old $Nf1^{+/neo}$ mice following in vivo LTR treatment. n=5 for all groups, O.N. Mdk R.E.p=0.015. FIG. 16C and FIG. 16D includes bar graphs showing Mdk, Adam10, and Nlgn3 transcript expression in (FIG. 16C) retinae (Mdk R.E. p=0.0020) and (FIG. 16D) optic nerves (Mdk R.E. p=0.0109) of 12 week-old Nf1-OPG mice following in vivo LTR treatment. n=4 for all groups. Data are represented as means±SEM, two-tailed paired t-test.

FIG. 17A is a bar graph showing Mdk transcript relative expression is decreased in retinae of $Nf1^{+/neo}$ mice following LTR treatment in vivo. n=5 for all groups. P=0.0204. FIG. 17B is a bar graph and FIG. 17C includes images showing Midkine expression is reduced in (FIG. 17B) $Nf1^{+/neo}$ RGC neurons in vitro (n=6 for all groups; P=0.0013), and (FIG. 17C) in the RGC layer (dotted lines, black arrow) of retinae in 12-week-old $Nf1^{f/neo}$; GFAP-Cre (Nf1-OPG) mice following LTR treatment in vivo (vehicle n=8; LTR n=7). FIG. 17D and FIG. 17E include bar graphs showing ZD7288 (ZD) treatment (30 μM) of WT and $Nf1^{+/1809}$ RGC neurons (FIG. 17D) increased midkine production (P<0.0001), but (FIG. 17E) did not alter Adam10 or Nlgn3 transcript expression in vitro (ns, not significant). n=4 for all groups. Data are represented as means±SEM, (FIG. 17A) unpaired two-tailed Student's t test, (FIG. 17B) paired Student's t test, (FIG. 17D and FIG. 17E) One-way ANOVA with (FIG. 17D) Tukey's or (FIG. 17E) Dunnett's post-test correction. P values are indicated within each panel. ns, not significant.

FIG. 18A-FIG. 18D are bar graphs showing (FIG. 18A-FIG. 18B) Tetrodotoxin (TTX; 1 μM; FIG. 18A, n=4 for both groups, p=0.0221; FIG. 18B, n=5 for both groups, p=0.0031) and (FIG. 18C-FIG. 18D) lamotrigine (LTR; 200 μM; FIG. 18C, vehicle n=3, LTR n=4, p=0.0491; FIG. 18D, n=6 for both groups, p<0.001) reduced (FIG. 18A) AP firing rates of and (FIG. 18B) midkine expression in $Nf1^{+/neo}$ hippocampal neurons. FIG. 18E is a bar graph showing ZD-7288 (30 μM) increases midkine secretion by $Nf1^{+/neo}$ hippocampal neurons. n=3 for both groups, p=0.0046. Data are represented as means±SEM, unpaired two-tailed student's t-test.

FIG. 19A and FIG. 19B contain representative phase-contrast images depicting (FIG. 19A) RGCs or (FIG. 19B) DRG neurons infected with scrambled control, shHcn1, shHcn2, or a combination of shHcn1 and shHcn2. Silencing of Hcn1/2 lead to neuronal death. Independently generated primary RGC and DRG neurons were infected 3 times with similar results. FIG. 19C contains images showing 6-hour treatment with TTX induced RGC and DRG neuronal cell death. Independently generated primary RGC and DRG neurons were treated with TTX 3 times with similar results. Scale bars, 100 μm.

FIG. 20 is a bar graph showing RAS activity is elevated in $Nf1^{+/neo}$ and $Nf1^{+/1809}$ RGC neurons relative to WT controls (P<0.0001). Data are represented as means±SEM. One-way ANOVA with Dunnett's post-test correction. P values are indicated within each panel.

FIG. 21 is a bar graph showing RAS activity is elevated in $Nf1^{+/neo}$ and $Nf1^{+/1809}$ hippocampal neurons relative to WT controls. n=5 for both groups, p<0.0001. Data are represented as means±SEM, one-way ANOVA with Dunnett's post-test correction.

FIG. 22A is a bar graph showing RAS activity is reduced in $Nf1^{+/neo}$ neurons following IN-1 treatment (1 μM; P=0.0003). n=5 for all groups. FIG. 22B is a bar graph showing Midkine levels are reduced in $Nf1^{+/neo}$ RGC neurons following IN-1 treatment. n=6 for all groups; P=0.0033. Data are represented as means±SEM, (FIG. 22A) unpaired two-tailed Student's t test, (FIG. 22B) paired Student's t test.

FIG. 23 is a bar graph showing hippocampal neuron midkine secretion is reduced following IN-1 treatment (1 μM). Vehicle n=12, IN-1 n=7, p<0.0001. Data are represented as means±SEM, unpaired two-tailed student's t-test.

FIG. 24A includes images showing RGC layer (dotted lines, black arrow) midkine expression is reduced following lovastatin treatment of 12-week-old Nf1-OPG animals in vivo. n=5 for all groups. FIG. 24B is a bar graph showing RAS-GTP is reduced in TTX (1 μM)- and LTR-treated $Nf1^{+/neo}$ RGCs. n=6 for all groups, P<0.0001. Data are represented as means±SEM, (FIG. 24B) One-way ANOVA with Dunnett's post-test correction.

FIG. 25 is a bar graph showing RAS activity is reduced in $Nf1^{+/neo}$ neurons following TTX and LTR treatment. n=6 for all groups, p<0.0001. Data are represented as means±SEM, one-way ANOVA with Dunnett's post-test correction.

FIG. 26A and FIG. 26B include bar graphs and traces showing $Nf1^{+/neo}$ RGC neuron AP firing rate is not reduced following IN-1 treatment, as measured by (FIG. 26A) multi-electrode array (vehicle n=5; IN-1 n=4), or (FIG. 26B) calcium-imaging recordings (vehicle n=22; IN-1 n=22). Right: (FIG. 26A) spike plots of entire multi-electrode array well recordings over 30 s, and (FIG. 26B) traces of neuronal activity over 3 min. Data are represented as means±SEM, unpaired two-tailed Student's t test.

FIG. 27 is a bar graph showing $Nf1^{+/neo}$ hippocampal neuron AP firing rates are not reduced following IN-1 treatment. n=4 for both groups. Data are represented as means±SEM, unpaired two-tailed student's t-test.

FIG. 28A is a graph demonstrating the relationship between optic nerve volumes and Ki67$^+$ cells in vehicle- and LTR-treated Nf1-OPG optic nerves. n=7 for both groups. FIG. 28B includes graphs and images showing LTR-treated (25 mg/kg/day intraperitoneally) Nf1-OPG mouse optic nerves have reduced Ki67$^+$ (P<0.0001), Iba1$^+$ (P=0.0033) and CD3$^+$ cells (P=0.0245) relative to vehicle-treated Nf1-OPG mice. n=7 for all groups. Scale bars, 100 μm. (FIG. 28B) Data are represented as means±SEM, unpaired two-tailed Student's t test.

FIG. 29A is a table showing incidence of peripheral nervous system tumors in NF1 patients harboring the c.5425 C>T NF1 germline mutation. pNF: plexiform neurofibroma; (a) 44, (b) 45, (c) 40. FIG. 29B includes representative gross images (brightfield) of spinal cords from 6-month-old $Nf1^{f/neo}$; Hoxb7-Cre (n=16), $Nf1^{f/f}$; Hoxb7-Cre (n=13), and $Nf1^{f/1809}$; Hoxb7-Cre (n=52) mice, showing enlarged DRG (red asterisks). Scale bars: 1 mm. The number of mice that formed pNFs is also shown in the top panels. FIG. 29C is a bar graph showing DRG are enlarged in Nf1$^{f/neo}$; Hoxb7-Cre (n=17; P<0.0001) and Nf1$^{f/f}$; Hoxb7-Cre mice (n=17; P=0.0313), but not in Nf1$^{f/1809}$; Hoxb7-Cre mice (n=17). FIG. 29D and FIG. 29E include images showing representative (FIG. 29D) H+E staining, GAP43, Factor XIIIa and CD34 staining, and (FIG. 29E) SOX10 and S100β, immunostaining. n=4 for all groups. FIG. 29F and FIG. 29G are bar graphs showing quantification of SOX10$^+$ (n=3 for all groups; Nf1$^{f/neo}$; Hoxb7-Cre, P=0.0028; Nf1$^{f/f}$; Hoxb7-Cre, P=0.0022) and DAPI$^+$ cells (Nf1$^{f/neo}$; Hoxb7-Cre, n=5, P=0.0028; Nf1$^{f/f}$; Hoxb7-Cre, n=5, P=0.0067; Nf1$^{+/1809}$; Hoxb7-Cre, n=4) in DRGs. Scale bars, 50 µm. Data are presented as the mean±SEM. One-way ANOVA with Tukey's test for multiple comparison.

FIG. 30A and FIG. 30B include graphs and traces showing Nf1$^{+/neo}$, but not Nf1$^{+/1809}$, DRG neuron AP firing rates are elevated relative to WT DRG neurons, as measured by (FIG. 30A) multi-electrode array (WT, n=24, Nf1$^{+/neo}$, n=10; P=0.0005, Nf1$^{+/1809}$ n=10, ns), or (FIG. 30B) calcium imaging recordings (WT n=8, Nf1$^{+/neo}$ n=5, P<0.0001, Nf1$^{+/1809}$ n=14, ns). The right panels show representative (FIG. 30A) spike plots of entire multi-electrode array well recordings over 30 s, and (FIG. 30B) traces of neuronal activity over 3 min. One-way ANOVA with Dunnett's multiple comparisons test.

FIG. 31 includes a graph and traces showing amplitudes of action potentials were similar in Nf1$^{+/neo}$ (n=3) and Nf1$^{+/1809}$ (n=3) DRG neurons relative to WT controls (n=4). Right panels: representative traces of DRG neuron action potentials over 3 msec (gray). The averages of the DRG action potential traces are indicated in black. Data are represented as means±SEM, one-way ANOVA with Dunnett's post-test correction.

FIG. 32A and FIG. 32B include graphs and traces showing TTX (1 µM) and lamotrigine (LTR; 200 µM) reduce Nf1$^{+/neo}$ DRG neuron AP firing rate as measured by multi-electrode array (vehicle n=4, TTX n=7, P<0.0001; LTR n=6, P<0.0001) and calcium imaging (vehicle n=23, TTX n=9, P<0.0001, LTR n=14, P<0.0001). The right panels show representative (FIG. 32A) spike plots of entire multi-electrode array well recordings over 30 s, and (FIG. 32B) traces of neuronal activity over 3 min. FIG. 32C includes a schematic illustrating treatment of human shNF1 Schwann cells with hiPSC-sensory neuron conditioned media (CM) and bar graph showing NF1-deficient Schwann cell proliferation is increased after treatment with NF1-C383X, NF1-R681X, and NF1-E2207X mutant neuron CM (P<0.0001), but not NF1-R1809C neuron CM relative to controls (CTL). n=6 for all groups. Data are presented as the mean±SEM. One-way ANOVA with (FIG. 32A and FIG. 32B) Dunnett's, or (FIG. 32C) Tukey's multiple comparisons test.

FIG. 33A includes images showing human shNF1 Schwann cells are immunopositive for EGR2, S100β, OCT6 and SOX10 expression. Immunostaining of human Schwann cells was repeated independently 3 times with similar results. Scale bars, 50 µm. FIG. 33B and FIG. 33C include images showing NF1$^{+/-}$ hiPSC-sensory neurons are immunopositive for (FIG. 33B) neurofilament, peripherin, BRN3A, ISL-1, and CALCA1 expression by western blot, as well as for (FIG. 33C) SMI32 and Tuj-1 by immunocytochemistry, but are immunonegative for Nestin and p75NTR expression. Scale bars, 50 µm. Immunostaining of hiPSC-sensory neurons was repeated independently a minimum of 3 times with similar results. FIG. 33D is a bar graph showing shNF1 human Schwann cell proliferation following hiPSC-sensory neuron CM treatment. CTL sh #1 n=6, Arg1809Cys sh #1 n=5, ns, Cys383X sh #1 n=6, p<0.0001, Arg681X sh #1 n=6, p<0.0001. CTL sh #2 n=3, Arg1809Cys sh #2 n=3, ns, Cys383X sh #2 n=3, p<0.0001, Arg681X sh #2 n=3, p<0.0001. CTL sh #3 n=3, Arg1809Cys sh #3 n=3, ns, Cys383X sh #3 n=3, p<0.0001, Arg681X sh #3 n=3, p<0.0001. Data are represented as means±SEM, 2-tailed paired t-tests or One-way ANOVA with Bonferroni post-test correction.

FIG. 34 includes images and a table showing analytical comparison of 2D gel electrophoresis (top-to-bottom: decreasing molecular weight; left-to-right: decreasing acidity) of NF1-R681X (left) and NF1-R1809C (right) CM relative to CTL hiPSC-sensory neuron CM. Red dots indicate proteins with increased expression, green dots indicate proteins with decreased expression, and yellow dots indicate unaltered proteins in NF1-mutant sensory neuron CM relative to CTL neuron CM. The six proteins uniquely increased more than 1.5-fold in NF1-R681X hiPSC-sensory neuron CM relative to CTL, but not in NF1-R1809C CM, relative to CTL are circled in blue and are listed in the lower panel. Representative CM from CTL, NF1-R1809C, and NF1-R681X sensory neurons was analyzed by 2D gel electrophoresis (n=1).

FIG. 35A and FIG. 35B include images showing (FIG. 35A) 2D gels of control (CTL), NF1-R681X (R681X) and NF1-R1809C (1809) human sensory neuron conditioned media and (FIG. 35B) annotation of increased (green) and decreased (red) proteins in CM of R681X (left) or R1809C (right) NF1-mutant relative to control sensory neurons.

FIG. 36A and FIG. 36B are bar graphs showing COL1A2 levels are increased in (FIG. 36A) NF1-C383X, NF1-R681X, and NF1-E2207X mutant neuron CM (P<0.0001), but not in NF1-R1809C neuron CM (n=4 for all groups), as well as in (FIG. 36B) Nf1$^{+/neo}$ mouse DRG neuron CM (P<0.0001), but not in Nf1$^{+/1809}$ mouse DRG neuron CM (n=6 for all groups). Data are presented as the mean±SEM. One-way ANOVA with Dunnett's multiple comparisons test.

FIG. 37A-FIG. 37E are bar graphs showing COL2A1, lactotransferrin, C7, albumin and ANXA2 expression in independently-generated hiPSC-sensory neuron CM were not uniquely elevated in NF1-C383X- and NF1-

R681X-mutant neurons relative to controls and NF1R1809C-mutant neurons. FIG. 37A, n=4 all groups. FIG. 37B, n=3 all groups, C383X p<0.0001. FIG. 37C, n=4 all groups. FIG. 37D, n=4 all groups, R681X p<00001. FIG. 37E, n=3 all groups, R681X p=0.0008 Data are represented as means±SEM, one-way ANOVA with Dunnett's post-test correction.

FIG. 38 is a bar graph showing Nf1-deficient DRG-NSC proliferation is increased after treatment with Nf1$^{+/neo}$ DRG neuron CM (P<0.0001), but not Nf1$^{+/1809}$ DRG neuron CM, relative to WT controls. n=6 for all groups. Data are presented as the mean±SEM, one-way ANOVA with Dunnett's multiple comparisons test.

FIG. 39A is a bar graph showing increased proliferation (% Ki67$^+$ cells) of mouse Nf1$^{-/-}$ DRG-NSCs following treatment with human NF1-R681X-, but not CTL- and NF1-R1809C-mutant, hiPSC-sensory neuron CM. n=6 all groups, p<0.0001. FIG. 39B is a bar graph showing Col1a2 expression is increased in mouse Nf1$^{+/neo}$ DRG neurons, but not in mouse Nf1$^{+/neo}$ RGC neurons. n=3 all groups. Data are represented as means±SEM, one-way ANOVA with Dunnett's post-test correction.

FIG. 40A and FIG. 40B contain images and bar graphs showing (FIG. 40A) immunofluorescent staining and (FIG. 40B) corresponding quantitation of Ki67$^+$ human shNF1 Schwann cells (left) and Nf1$^{-/-}$ mouse DRG-NSCs (right) following incubation with hiPSC-sensory neuron conditioned media (CM), with (h P=0.0007; m P<0.0001) and without (P<0.0001) collagenase (n=6 for all groups), COL1A2 alone with (h P=0.0036; m P<0.0001) and without (P<0.0001) collagenase (n=6 for all groups), as well as with and without control or short hairpins against COL1A2 (n=3 for all groups, P<0.0001) or Col1a2 (vehicle n=4, control short hairpin n=7, shCol1a2-1 n=4, sh Col1a2-2 n=4, sh Col1a2-3 n=3, P<0.0001). Data are presented as the mean±SEM, one way ANOVA with Tukey's or multiple comparisons test. Scale bars, 50 µm.

FIG. 41A-FIG. 41D are bar graphs showing genetic inhibition of (FIG. 41A-FIG. 41B) human COL1A2 or (FIG. 41C-FIG. 41D) mouse Col1a2 with three independent short hairpin constructs reduces COL1A2 and Col1a2 (FIG. 41A and FIG. 41C) transcript and (FIG. 41B and FIG. 41D) protein expression relative to a control scrambled short hairpin (shCTL). FIG. 41A, n=3 all groups, p=0.0006. FIG. 41B, shCTL n=4, shCOL1A2 #1-3 n=3; p<0.0001. FIG. 41C, n=3 all groups; shCol1a2 #1 p=0.0337, shCol1a2 #2 p=0.0143, shCol1a2 #3 p=0.0246. FIG. 41D, n=4 all groups, p<0.0001.

FIG. 42A and FIG. 42B include images showing (FIG. 42A) human and (FIG. 42B) mouse cutaneous (cNF) and plexiform neurofibromas (pNF) express COL1A2. Normal brain, lymph node and normal sural (human) or normal sciatic (mouse) nerves were negative for COL1A2 expression. Neurofilament was used as positive control for normal mouse nerve tissue. These data derive from a single-tissue microarray. FIG. 42C is a bar graph showing COL1A2 RNA expression is increased in human shNF1 Schwann cells (left; P=0.0014) and mouse Nf1$^{-/-}$ DRG-NSCs (right; P=0.0012) following COL1A2 treatment. n=3 for all groups. FIG. 42D is a bar graph showing COL1A2 RNA expression is increased in human Schwann cells isolated from human cNF (P=0.0039) and pNF tumors (P=0.0022) relative to controls. Normal n=10, cNF n=11, pNF n=11. Data are presented as the mean±SEM. (FIG. 42D) One way ANOVA with Dunnett's multiple comparisons test, or (FIG. 42C) paired two-tailed Student t test. Scale bars, 50 µm.

FIG. 43A and FIG. 43B are bar graphs showing TTX (1 µM; FIG. 43A; vehicle n=6, TTX n=6; P<0.0001) and lamotrigine (LTR; 200 µM; FIG. 43B; vehicle n=9, LTR n=9; P=0.0001) reduce Nf1$^{+/neo}$ DRG neuron Col1a2 secretion by 73 and 47% relative to vehicle-treated controls. FIG. 43C is a bar graph showing ZD7288 (ZD; 30 µM) increases Col1a2 secretion in WT (n=10 in both groups; P<0.0001) and Nf1$^{+/1809}$ (n=4 in both groups; P=0.0103) DRG neurons. FIG. 43D and FIG. 43E are bar graphs showing (FIG. 43D) RAS activity is increased in both Nf1$^{+/neo}$ and Nf1$^{+/1809}$ DRG neurons relative to controls (n=5 in all groups; P<0.0001), (FIG. 43E) and is inhibited following TTX and LTR treatment (n=6 in all groups; P<0.0001). FIG. 43F and FIG. 43G include graphs and traces showing IN-1 has no effect on DRG neuronal activity, as measured by (FIG. 43F) multi-electrode array (vehicle n=6, IN-1 n=3, ns not significant), or (FIG. 43G) calcium-imaging recordings (vehicle n=18, IN-1 n=18; ns, not significant). Right: representative (FIG. 43F) spike plots of entire multi-electrode array well recordings over 30 s, and (FIG. 43G) traces of neuronal activity over 3 min. FIG. 43H is a bar graph showing IN-1 reduces Col1a2 secretion by 77.9% in Nf1$^{+/neo}$ DRG neurons. n=6 for both groups, P=0.0001. Data are represented as means±SEM (FIG. 43A-FIG. 43C and FIG. 43H) using two-tailed paired Student's t tests, (FIG. 43F and FIG. 43G) two-tailed unpaired t tests, or (FIG. 43D and FIG. 43E) one-way ANOVA with Dunnett's post-test correction.

FIG. 44A includes bar graphs showing Hcn1-4 expression is not altered in Nf1-mutant DRG neurons relative to WT controls. n=4 all groups. FIG. 44B is a bar graph showing RAS activity is increased in human NF1-R681X- and NF1-R1809C-mutant hiPSC-sensory neurons relative to controls. n=3 all groups, R681X p<0.0001, R1809C p=0.0001. FIG. 44C is a bar graph showing COL1A2 is reduced in NF1681X-mutant hiPSC-sensory neurons following IN-1 treatment. n=5 both groups, p<0.0001. Data are represented as means±SEM, (FIG. 44A and FIG. 44B) One-way ANOVA with Dunnett's post-test correction or (FIG. 44C) two-tailed paired t-test.

FIG. 45A is a bar graph showing IN-1 reduces proliferation by 50% in Nf1$^{-/-}$ DRG-NSCs. n=6 for both groups, P<0.0001. Data are represented as means±SEM using two-tailed paired Student's t tests. FIG. 45B includes images showing lamotrigine treatment decreases pNF progression in vivo. Gross images and representative immunostaining of mouse pNFs demonstrate that LTR treatment reduces pNF size, partly restores neuronal histology (H&E), reduces proliferation (Ki67+ cells), and decreases Col1a2 production. Scale bars: gross anatomy images, 1 mm; sections, 100 µm. n=5 for both groups.

FIG. 46A is a schematic showing tumor-associated NF1-mutant sensory neurons have increased baseline neuron excitability and deregulated HCN channel function, leading to elevated COL1A2 secretion. COL1A2, in turn, increases NF1$^{-/-}$ Schwann cell proliferation to stimulate pNF growth. FIG. 46B is a schematic showing tumor-associated Nf1-mutant retinal ganglion cell (RGC) activity is governed by two distinct mechanisms. First, visual experience (light)-induced activity enhances RGC production of soluble-Nlgn3 (s-Nlgn3), which drives OPG initiation and cell growth. Second, tumor-associated Nf1-mutant RGCs have increased intrinsic baseline neuronal hyperexcitability, which is controlled by HCN channel function. Increased baseline HCN channel-regulated RGC excitability triggers increased midkine production to induce a T cell (Ccl4) and microglial (Ccl5) signaling cascade that governs OPG progression and growth. PNS, peripheral nervous system, CNS, central nervous system, pNF, plexiform neurofibroma, OPG, optic pathway glioma.

FIG. 49A shows vehicle vs LTR images and ON volumes vs % Ki67+ cells. FIG. 49B shows microscope images and data comparisons for vehicle vs LTR across Ki67, Iba1 and CD3. Data are represented as means±SEM, unpaired two-tailed Student's t test.

DETAILED DESCRIPTION

Figures 1A, 1B:
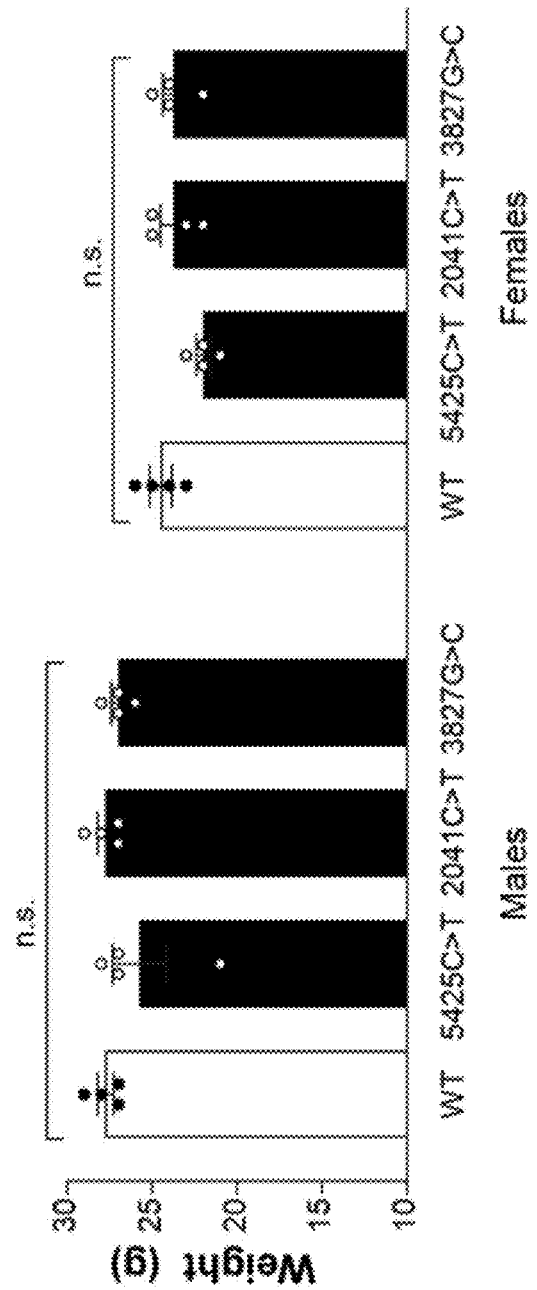
FIG. 1A-FIG. 1B shows an exemplary embodiment of characterization of the Arg1809Cys Nf1-mutant mouse strain in accordance with the present disclosure.

The present disclosure is based, at least in part, on the discovery that neuronal hyperexcitability promotes central and peripheral nervous system tumor progression in Neurofibromatosis-1 (NF1). As shown herein, drugs that inhibit neuronal hyperactivity may be repurposed to treat nervous system tumors in NF1, such as FDA-approved drugs already in use for treating children with epilepsy and related disorders.

NF1 is caused by loss of function mutation in neurofibromin, a GTPase activating protein (GAP) whose downstream target is Ras. NF1 can lead to both central (CNS) or peripheral (PNS) nervous system tumors in the glial or Schwann cells, respectively. NF1 is a debilitating disease affecting mostly children from a very young age. While KOSELUGO™ (selumetinib) has been awarded orphan drug status for treating cutaneous PNS-associated NF1 called plexiform neurofibroma, there is currently no treatment for NF1 as a whole, The methods described herein, which may be used to treat both CNS and PNS NF1, may be a major clinical breakthrough for NF1. As described herein, neurofibromin loss in NF1 has been associated with decreased HCN activity and corresponding increase in midkine (CNS) and COL1A2 (PNS) secretion. Lamotrigine reversed both of these effects, and had a measurable effect on both CNS and PNS tumor growth (see e.g., Example 1).

It was recently demonstrated that neuronal hyperexcitability drives Neurofibromatosis type 1 (NF1) optic gliomas in mice, such that light deprivation of tumor-prone mice inhibits optic glioma formation. This observation suggested that neuronal hyperexcitability conferred by NF1 mutation dictates tumor formation and progression. Demonstrated herein is that brain neurons control low-grade glioma growth by secreting midkine in an activity-dependent manner involving the hyperpolarization-activated cyclic nucleotide-gated (HCN) channel, and that peripheral sensory neurons similarly control low-grade peripheral nerve sheath tumor (neurofibroma) growth by secreting collagen-1A2 in an activity-dependent manner also involving the hyperpolarization-activated cyclic nucleotide-gated (HCN) channel. Importantly, neuronal excitability, activity-regulated mitogen production, and tumor progression are all attenuated by HCN channel activation using the anti-epileptic drug, lamotrigine (see e.g., Example 1). These findings suggest that drugs that attenuate neuronal hyperexcitability may be repurposed as anti-tumoral therapies.

Described herein is the repurposing of a class of anti-epilepsy/anti-convulsant drugs whose agonistic target is the hyperpolarization-activated, cyclic nucleotide-gated (HCN) ion channels, and that these drugs demonstrate therapeutic efficacy against NF1. The use of lamotrigine and rufinamide is tested herein (see e.g., Example 1 and Example 2), but other anti-epileptic drugs and/or HCN channel agonists may also be used.

Nervous System, Brain, or Spinal Cord Tumors

The present disclosure provides methods of treating or preventing cancer or tumor formation, proliferation, or growth in a subject in need thereof, particularly nervous system tumors associated with NF1. The nervous system tumor may be a central nervous system (CNS) or peripheral nervous system tumor (PNS) associated with NF1, such as a glioma (low- or high-grade), an optic pathway glioma (OPG), neurofibroma, peripheral nerve sheath tumor, or plexiform NF1, etc. In some embodiments, the astrocytoma is selected from grade 1 pilocytic astrocytoma, grade 2 low-grade astrocytoma, grade 3 anaplastic astrocytoma, or grade 4 glioblastoma (GBM). In some embodiments, the glioma is selected from brainstem glioma, glioma, or optic pathway glioma.

Neuronal Activity Inhibiting Agents

As described herein, neuronal activity or excitability has been implicated as a driver of central and peripheral nervous system cancers. As such, modulation of neuronal activity, such as by way of modulating HCN channel activity, can be used for the treatment of such conditions. A neuronal activity inhibiting agent can modulate neuronal activity by, for example, activating HCN channels or reducing action potential (AP) firing rates.

One aspect of the present disclosure provides for targeting neuronal activity or excitability or HCN channels. The present disclosure provides methods of treating or preventing tumor growth based on the discovery that neuronal hyperexcitability drives Neurofibromatosis type 1 (NF1)-associated nervous system cancers.

Antiepileptic Drugs (AEDs)

In some embodiments, the neuronal activity inhibiting agent is an antiepileptic drug (AED). Most antiepileptic drugs (AEDs) aim to reduce the excitability in neural tissue by reducing the excitability of individual neurons through selective ion channel blockers, enhancing inhibitory synaptic transmission, or inhibiting excitatory synaptic transmission.

For example, an AED can be VALIUM® (diazepam); TOPAMAX® (topiramate); ZONEGRAN® (zonisamide); TEGRETOL® (carbamazepine); TRILEPTAL® (oxcarbazepine); APTIOM® (eslicarbazepine); EPITOL® (carbamazepine); DEPAKOTE® (divalproex sodium); LYRICA® (pregabalin); NEURONTIN® (gabapentin); DILANTIN® (phenytoin); VIMPAT® (lacosamide); KEPPRA® (levetiracetam); LAMICTAL® (lamotrigine); GABITRIL® (tiagabine); MEBARAL® (mephobarbital); LUMINAL® (phenobarbital); DIAMOX® (acetazolamide); CARBATROL® (carbamazepine); EQUETRO® (carbamazepine); OXTELLAR XR® (oxcarbazepine); CARNEXIV® (carbamazepine); DEPAKENE® (valproic acid); STAVZOR® (valproic acid); DEPACON® (valproic acid); HORIZANT® (gabapentin enacarbil); GRALISE® (gabapentin); GABORONE® (gabapentin); SABRIL® (vigabatrin); FANATREX™ (gabapentin); DIACOMIT® (stiripentol); PHENYTEK® (phenytoin); PEGANONE® (mephenytoin); CEREBYX® (fosphenytoin); (phenytoin); MESANTOIN® FINETELPLA® (fenfluramine); EPIDIOLEX® (cannabidiol); POTIGA™ (ezogabine); TRIDIONE® (trimethadione); BRIVIACT® (brivaracetam); SPRITAM® (levetiracetam); ROWEEPRA® (levetiracetam); ZARONTIN® (ethosuximide); CELONTIN® (methsuximide); FYCOMPA® (perampanel); KLONOPIN® (clonazepam); VERSED® (midazolam); FELBATOL® (felbamate); XCOPRI® (cenobamate); MYSOLINE® (primidone); ONFI® (clobazam); ATIVAN® (lorazepam); TRANXENE-T® (clorazepate); BANZEL® (rufinamide); or TROKENDI XR® (topiramate).

In some preferred embodiments, the AED is lamotrigine. In some preferred embodiments, the AED is rufinamide.

HCN Channel Agonist

In some embodiments, the neuronal activity inhibiting agent is a hyperpolarization-activated cyclic nucleotide-gated (HCN) channel agonist. As described herein, HCN channels directly modulate neuronal excitability and HCN channel dysregulation is responsible for Nf1-mutant central and peripheral nervous system neuronal hyperexcitability and increased tumor-driving paracrine factor release. As such, HCN channel targeting was used to inhibit Nf1-OPG progression in vivo (see e.g., Example 1).

An HCN channel agonist can be any compound that activates an HCN channel or increases the activity thereof. For example, an HCN channel agonist can be lamotrigine.

Formulation

The agents and compositions described herein can be formulated by any conventional manner using one or more pharmaceutically acceptable carriers or excipients as described in, for example, Remington's Pharmaceutical Sciences (A. R. Gennaro, Ed.), 21st edition, ISBN: 0781746736 (2005), incorporated herein by reference in its entirety. Such formulations will contain a therapeutically effective amount of a biologically active agent described herein, which can be in purified form, together with a suitable amount of carrier so as to provide the form for proper administration to the subject.

The term "formulation" refers to preparing a drug in a form suitable for administration to a subject, such as a human. Thus, a "formulation" can include pharmaceutically acceptable excipients, including diluents or carriers.

The term "pharmaceutically acceptable" as used herein can describe substances or components that do not cause unacceptable losses of pharmacological activity or unacceptable adverse side effects. Examples of pharmaceutically acceptable ingredients can be those having monographs in United States Pharmacopeia (USP 29) and National Formulary (NF 24), United States Pharmacopeial Convention, Inc, Rockville, Maryland, 2005 ("USP/NF"), or a more recent edition, and the components listed in the continuously updated Inactive Ingredient Search online database of the FDA. Other useful components that are not described in the USP/NF, etc. may also be used.

The term "pharmaceutically acceptable excipient," as used herein, can include any and all solvents, dispersion media, coatings, antibacterial and antifungal agents, isotonic, or absorption delaying agents. The use of such media and agents for pharmaceutically active substances is well known in the art (see generally Remington's Pharmaceutical Sciences (A. R. Gennaro, Ed.), 21st edition, ISBN: 0781746736 (2005)). Except insofar as any conventional media or agent is incompatible with an active ingredient, its use in the therapeutic compositions is contemplated. Supplementary active ingredients can also be incorporated into the compositions.

A "stable" formulation or composition can refer to a composition having sufficient stability to allow storage at a convenient temperature, such as between about 0° C. and about 60° C., for a commercially reasonable period of time, such as at least about one day, at least about one week, at least about one month, at least about three months, at least about six months, at least about one year, or at least about two years.

The formulation should suit the mode of administration. The agents of use with the current disclosure can be formulated by known methods for administration to a subject using several routes which include, but are not limited to, parenteral, pulmonary, oral, topical, intradermal, intratumoral, intranasal, inhalation (e.g., in an aerosol), implanted, intramuscular, intraperitoneal, intravenous, intrathecal, intracranial, intracerebroventricular, subcutaneous, epidural, intrathecal, ophthalmic, transdermal, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic, or other physical forces.

Controlled-release (or sustained-release) preparations may be formulated to extend the activity of the agent(s) and reduce dosage frequency. Controlled-release preparations can also be used to affect the time of onset of action or other characteristics, such as blood levels of the agent, and consequently, affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

Agents or compositions described herein can also be used in combination with other therapeutic modalities, as described further below. Thus, in addition to the therapies described herein, one may also provide to the subject other therapies known to be efficacious for treatment of the disease, disorder, or condition.

Therapeutic Methods

Also provided is a process of treating, preventing, or reversing tumor growth or cancer, such as an NF1-associated nervous system tumor, in a subject in need of administration of a therapeutically effective amount of a neuronal activity inhibiting agent, so as to attenuate neuronal excitability, activity-regulated mitogen production, or tumor progression.

Methods described herein are generally performed on a subject in need thereof. A subject in need of the therapeutic methods described herein can be a subject having, diagnosed with, suspected of having, or at risk for developing tumors or cancer. A determination of the need for treatment will typically be assessed by a history, physical exam, or diagnostic tests consistent with the disease or condition at issue. Diagnosis of the various conditions treatable by the methods described herein is within the skill of the art. The subject can be an animal subject, including a mammal, such as horses, cows, dogs, cats, sheep, pigs, mice, rats, monkeys, hamsters, guinea pigs, and humans or chickens. For example, the subject can be a human subject.

Generally, a safe and effective amount of a neuronal activity inhibiting agent is, for example, an amount that would cause the desired therapeutic effect in a subject while minimizing undesired side effects. In various embodiments, an effective amount of a neuronal activity inhibiting agent described herein can substantially inhibit tumor growth or cancer proliferation, slow the progress of tumor growth or cancer proliferation, or limit the development of tumor growth or cancer proliferation.

According to the methods described herein, administration can be parenteral, pulmonary, oral, topical, intradermal, intramuscular, intraperitoneal, intravenous, intratumoral, intrathecal, intracranial, intracerebroventricular, subcutaneous, intranasal, epidural, ophthalmic, buccal, or rectal administration.

When used in the treatments described herein, a therapeutically effective amount of a neuronal activity inhibiting agent can be employed in pure form or, where such forms exist, in pharmaceutically acceptable salt form and with or without a pharmaceutically acceptable excipient. For example, the compounds of the present disclosure can be administered, at a reasonable benefit/risk ratio applicable to any medical treatment, in a sufficient amount to reduce or inhibit neuronal activity, activate HCN channels, substantially inhibit tumor growth or cancer proliferation, slow the progress of tumor growth or cancer proliferation, or limit the development of tumor growth or cancer proliferation.

The amount of a composition described herein that can be combined with a pharmaceutically acceptable carrier to produce a single dosage form will vary depending upon the subject or host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where larger therapeutic indices are generally understood in the art to be optimal.

The specific therapeutically effective dose level for any particular subject will depend upon a variety of factors including the disorder being treated and the severity of the disorder; the activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, $4^{th}$ ed., Lippincott Williams & Wilkins, ISBN 0781741475; Sharqel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Again, each of the states, diseases, disorders, and conditions, described herein, as well as others, can benefit from compositions and methods described herein. Generally, treating a state, disease, disorder, or condition includes preventing, reversing, or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., suppressing, arresting, or reducing the development or growth of the disease or at least one clinical or subclinical symptom thereof. For example, treating a tumor (or tumor cell) can include suppressing, arresting, or reducing progression, proliferation, or growth of the tumor (or tumor cell). Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or a physician.

Administration of a neuronal activity inhibiting agent can occur as a single event or over a time course of treatment. For example, a neuronal activity inhibiting agent can be administered daily, weekly, bi-weekly, or monthly. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

Treatment in accord with the methods described herein can be performed prior to or before, concurrent with, or after conventional treatment modalities for cancer or anti-tumor therapy.

A neuronal activity inhibiting agent can be administered simultaneously or sequentially with another agent, such as an antibiotic, an anti-inflammatory, or another agent. For example, a neuronal activity inhibiting agent can be administered simultaneously with another agent, such as an antibiotic or an anti-inflammatory. Simultaneous administration can occur through administration of separate compositions, each containing one or more of a neuronal activity inhibiting agent, an antibiotic, an anti-inflammatory, or another agent. Simultaneous administration can occur through administration of one composition containing two or more of a neuronal activity inhibiting agent, an antibiotic, an anti-inflammatory, or another agent. A neuronal activity inhibiting agent can be administered sequentially with an antibiotic, an anti-inflammatory, or another agent. For example, a neuronal activity inhibiting agent can be administered before or after administration of an antibiotic, an anti-inflammatory, or another agent.

Active compounds are administered at a therapeutically effective dosage sufficient to treat a condition associated with a condition in a patient. For example, the efficacy of a compound can be evaluated in an animal model system that may be predictive of efficacy in treating the disease in a human or another animal, such as the model systems shown in the examples and drawings.

An effective dose range of a therapeutic can be extrapolated from effective doses determined in animal studies for a variety of different animals. In general, a human equivalent dose (HED) in mg/kg can be calculated in accordance with the following formula (see e.g., Reagan-Shaw et al., *FASEB J.*, 22(3):659-661, 2008, which is incorporated herein by reference):

$$\text{HED (mg/kg)} = \text{Animal dose (mg/kg)} \times (\text{Animal } K_m / \text{Human } K_m)$$

Use of the $K_m$ factors in conversion results in more accurate HED values, which are based on body surface area (BSA) rather than only on body mass. $K_m$ values for humans and various animals are well known. For example, the $K_m$ for an average 60 kg human (with a BSA of 1.6 m$^2$) is 37, whereas a 20 kg child (BSA 0.8 m$^2$) would have a $K_m$ of 25. $K_m$ for some relevant animal models are also well known, including: mice $K_m$ of 3 (given a weight of 0.02 kg and BSA of 0.007); hamster $K_m$ of 5 (given a weight of 0.08 kg and BSA of 0.02); rat $K_m$ of 6 (given a weight of 0.15 kg and BSA of 0.025) and monkey $K_m$ of 12 (given a weight of 3 kg and BSA of 0.24).

Precise amounts of the therapeutic composition depend on the judgment of the practitioner and are peculiar to each individual. Nonetheless, a calculated HED dose provides a general guide. Other factors affecting the dose include the physical and clinical state of the patient, the route of administration, the intended goal of treatment, and the potency, stability, and toxicity of the particular therapeutic formulation.

The actual dosage amount of a compound of the present disclosure or composition comprising a compound of the present disclosure administered to a subject may be determined by physical and physiological factors such as type of animal treated, age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject. The dosage may be adjusted by the individual physician in the event of any complication.

In some embodiments, the neuronal activity inhibiting agent may be administered in an amount from about 1 mg to about 300 mg. For example, the neuronal activity inhibiting agent can be administered in a dose of about 2 mg, 5 mg, 25 mg, 100 mg, 150 mg, 200 mg, 250 mg, or 300 mg.

In some embodiments, the neuronal activity inhibiting agent may be administered in an amount from about 1 mg/kg to about 100 mg/kg, or about 1 mg/kg to about 50 mg/kg, or about 1 mg/kg to about 25 mg/kg, or about 1 mg/kg to about 15 mg/kg, or about 1 mg/kg to about 10 mg/kg, or about 1 mg/kg to about 5 mg/kg, or about 3 mg/kg. In some embodiments, a neuronal activity inhibiting agent may be administered in a range of about 1 mg/kg to about 200 mg/kg, or about 50 mg/kg to about 200 mg/kg, or about 50 mg/kg to about 100 mg/kg, or about 75 mg/kg to about 100 mg/kg, or about 100 mg/kg.

The effective amount may be less than 1 mg/kg/day, less than 500 mg/kg/day, less than 250 mg/kg/day, less than 100 mg/kg/day, less than 50 mg/kg/day, less than 25 mg/kg/day or less than 10 mg/kg/day. It may alternatively be in the range of 1 mg/kg/day to 200 mg/kg/day.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

Administration

Agents and compositions described herein can be administered according to methods described herein in a variety of means known to the art. The agents and composition can be used therapeutically either as exogenous materials or as endogenous materials. Exogenous agents are those produced or manufactured outside of the body and administered to the body. Endogenous agents are those produced or manufactured inside the body by some type of device (biologic or other) for delivery within or to other organs in the body.

As discussed above, administration can be parenteral, pulmonary, oral, topical, intradermal, intratumoral, intranasal, inhalation (e.g., in an aerosol), implanted, intramuscular, intraperitoneal, intravenous, intrathecal, intracranial, intracerebroventricular, subcutaneous, intranasal, epidural, intrathecal, ophthalmic, transdermal, buccal, and rectal.

Agents and compositions described herein can be administered in a variety of methods well known in the arts. Administration can include, for example, methods involving oral ingestion, direct injection (e.g., systemic or stereotactic), implantation of cells engineered to secrete the factor of interest, drug-releasing biomaterials, polymer matrices, gels, permeable membranes, osmotic systems, multilayer coatings, microparticles, implantable matrix devices, mini-osmotic pumps, implantable pumps, injectable gels and hydrogels, liposomes, micelles (e.g., up to 30 μm), nanospheres (e.g., less than 1 μm), microspheres (e.g., 1-100 μm), reservoir devices, a combination of any of the above, or other suitable delivery vehicles to provide the desired release profile in varying proportions. Other methods of controlled-release delivery of agents or compositions will be known to the skilled artisan and are within the scope of the present disclosure.

Delivery systems may include, for example, an infusion pump which may be used to administer the agent or composition in a manner similar to that used for delivering insulin or chemotherapy to specific organs or tumors. Typically, using such a system, an agent or composition can be administered in combination with a biodegradable, biocompatible polymeric implant that releases the agent over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

Agents can be encapsulated and administered in a variety of carrier delivery systems. Examples of carrier delivery systems include microspheres, hydrogels, polymeric implants, smart polymeric carriers, and liposomes (see generally, Uchegbu and Schatzlein, eds. (2006) Polymers in Drug Delivery, CRC, ISBN-10:0849325331). Carrier-based systems for molecular or biomolecular agent delivery can: provide for intracellular delivery; tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to nontarget tissues; decrease irritation caused by the agent; decrease toxicity due to high initial doses of the agent; alter the immunogenicity of the agent; decrease dosage frequency; improve taste of the product; or improve shelf life of the product.

Screening

Also provided are screening methods.

The subject methods find use in the screening of a variety of different candidate molecules (e.g., potentially therapeutic candidate molecules). Candidate substances for screening according to the methods described herein include, but are not limited to, fractions of tissues or cells, nucleic acids, polypeptides, siRNAs, antisense molecules, aptamers, ribozymes, triple helix compounds, antibodies, and small (e.g., less than about 2000 MW, or less than about 1000 MW, or less than about 800 MW) organic molecules or inorganic molecules including but not limited to salts or metals.

Candidate molecules encompass numerous chemical classes, for example, organic molecules, such as small organic compounds having a molecular weight of more than 50 and less than about 2,500 Daltons. Candidate molecules can comprise functional groups necessary for structural interaction with proteins, particularly hydrogen bonding, and typically include at least an amine, carbonyl, hydroxyl, or carboxyl group, and usually at least two of the functional chemical groups. The candidate molecules can comprise cyclical carbon or heterocyclic structures and/or aromatic or polyaromatic structures substituted with one or more of the above functional groups.

A candidate molecule can be a compound in a library database of compounds. One of skill in the art will be generally familiar with, for example, numerous databases for commercially available compounds for screening (see e.g., ZINC database, UCSF, with 2.7 million compounds over 12 distinct subsets of molecules; Irwin and Shoichet (2005) J Chem Inf Model 45, 177-182). One of skill in the art will also be familiar with a variety of search engines to identify commercial sources or desirable compounds and classes of compounds for further testing (see e.g., ZINC database; eMolecules; and electronic libraries of commercial compounds provided by vendors, for example, ChemBridge, Princeton BioMolecular, Ambinter SARL, Enamine, ASDI, Life Chemicals, etc.).

Candidate molecules for screening according to the methods described herein include both lead-like compounds and drug-like compounds. A lead-like compound is generally understood to have a relatively smaller scaffold-like structure (e.g., molecular weight of about 150 to about 350 kD) with relatively fewer features (e.g., less than about 3 hydrogen donors and/or less than about 6 hydrogen acceptors; hydrophobicity character x log P of about −2 to about 4) (see e.g., Angewante (1999) Chemie Int. ed. Engl. 24, 3943-3948). In contrast, a drug-like compound is generally understood to have a relatively larger scaffold (e.g., molecular weight of about 150 to about 500 kD) with relatively more numerous features (e.g., less than about 10 hydrogen acceptors and/or less than about 8 rotatable bonds; hydrophobicity character x log P of less than about 5) (see e.g., Lipinski (2000) J. Pharm. Tox. Methods 44, 235-249). Initial screening can be performed with lead-like compounds.

When designing a lead from spatial orientation data, it can be useful to understand that certain molecular structures are characterized as being "drug-like". Such characterization can be based on a set of empirically recognized qualities derived by comparing similarities across the breadth of known drugs within the pharmacopoeia. While it is not required for drugs to meet all, or even any, of these characterizations, it is far more likely for a drug candidate to meet with clinical success if it is drug-like.

Several of these "drug-like" characteristics have been summarized into the four rules of Lipinski (generally known as the "rules of fives" because of the prevalence of the number 5 among them). While these rules generally relate to oral absorption and are used to predict the bioavailability of a compound during lead optimization, they can serve as effective guidelines for constructing a lead molecule during rational drug design efforts such as may be accomplished by using the methods of the present disclosure.

The four "rules of five" state that a candidate drug-like compound should have at least three of the following characteristics: (i) a weight less than 500 Daltons; (ii) a log of P less than 5; (iii) no more than 5 hydrogen bond donors (expressed as the sum of OH and NH groups); and (iv) no more than 10 hydrogen bond acceptors (the sum of N and O atoms). Also, drug-like molecules typically have a span (breadth) of between about 8 Å to about 15 Å.

Kits

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components include, but are not limited to neuronal activity inhibiting agents. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline each of which has been packaged under a neutral non-reacting gas, such as nitrogen. Ampules may consist of any suitable material, such as glass, organic polymers, such as polycarbonate, polystyrene, ceramic, metal, or any other material typically employed to hold reagents. Other examples of suitable containers include bottles that may be fabricated from similar substances as ampules and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or another substrate, and/or may be supplied as an electronic-readable medium or video. Detailed instructions may not be physically associated with the kit; instead, a user may be directed to an Internet web site specified by the manufacturer or distributor of the kit.

A control sample or a reference sample as described herein can be a sample from a healthy subject or sample, a wild-type subject or sample, or from populations thereof. A reference value can be used in place of a control or reference sample, which was previously obtained from a healthy subject or a group of healthy subjects or a wild-type subject or sample. A control sample or a reference sample can also be a sample with a known amount of a detectable compound or a spiked sample.

Compositions and methods described herein utilizing molecular biology protocols can be according to a variety of standard techniques known to the art (see e.g., Sambrook and Russel (2006) Condensed Protocols from Molecular Cloning: A Laboratory Manual, Cold Spring Harbor Laboratory Press, ISBN-10:0879697717; Ausubel et al. (2002) Short Protocols in Molecular Biology, 5th ed., Current Protocols, ISBN-10:0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41 (1), 207-234; Gellissen, ed. (2005) Production of Recombinant Proteins: Novel Microbial and Eukaryotic Expression Systems, Wiley-VCH, ISBN-10:3527310363; Baneyx (2004) Protein Expression Technologies, Taylor & Francis, ISBN-10:0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein. The recitation of discrete values is understood to include ranges between each value.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application, or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1: Neuronal Hyperexcitability Drives Central and Peripheral Nervous System Tumor Progression in Neurofibromatosis-1

This example describes methods of treating both central and peripheral nervous system neurofibromatosis type I (NF1).

Abstract

Neuronal activity is emerging as a driver of central and peripheral nervous system cancers. Herein, neuronal physiology was examined in mouse models of the tumor predisposition syndrome Neurofibromatosis-1 (NF1), with different propensities to develop nervous system cancers. As shown herein, central and peripheral nervous system neurons from mice with tumor-causing Nf1 gene mutations exhibit hyperexcitability and increased secretion of activity-dependent tumor-promoting paracrine factors. A neurofibroma mitogen (COL1A2) produced by peripheral neurons in an activity-regulated manner was discovered, which increases NF1-deficient Schwann cell proliferation, establishing that neurofibromas are regulated by neuronal activity. In contrast, mice with the Arg1809Cys Nf1 mutation, found in NF1 patients lacking neurofibromas or optic gliomas, do not exhibit neuronal hyperexcitability or develop these NF1-associated tumors. The hyperexcitability of tumor-prone Nf1-mutant neurons results from reduced NF1-regulated hyperpolarization-activated cyclic nucleotide-gated (HCN) channel function, such that neuronal excitability, activity-regulated paracrine factor production, and tumor progression are attenuated by HCN channel activation. Collectively, these findings reveal that NF1 mutations act at the level of neurons to modify tumor predisposition by increasing neuronal excitability and activity-regulated paracrine factor production.

INTRODUCTION

While the acquisition of genetic or epigenetic aberrations in preneoplastic cells is an obligate event in tumor formation and progression, cancer growth is also dictated by paracrine factors produced by non-neoplastic cells in the local tumor microenvironment. These tumor-stroma interactions are nicely illustrated in the setting of the neurofibromatosis type 1 (NF1) genetic cancer predisposition syndrome. Patients with NF1, born with a germline mutation in the NF1 tumor suppressor gene, are prone to developing various tumors, including central and peripheral nervous system tumors, as well as malignancies of the adrenal glands, muscle, blood, and breast. In NF1 nervous system tumors, paracrine factors from T cells, monocytes (macrophages, microglia), and mast cells generate a supportive tumor microenvironment necessary for continued peripheral (neurofibromas) and central (gliomas) nervous system tumor expansion. As such, plexiform neurofibroma (pNF) formation and growth is controlled by the interplay of mast cells, macrophages, leukocytes, and fibroblasts through paracrine factor elaboration, whereas T cells and microglia influence glioma growth through cytokine (Ccl4, Ccl5) signaling.

In addition to the critical contributions from immune system cells, it was recently shown that NF1 mutation in neurons synergizes with light-induced retinal ganglion cell activity to regulate neuroligin-3 (NLGN3) shedding and Nf1-optic pathway glioma (Nf1-OPG) initiation and growth. This finding builds upon prior reports establishing that neurons and neuronal activity increase high-grade glioma growth through the secretion of paracrine factors, like NLGN3 and brain-derived neurotrophic factor (BDNF), in an activity-dependent manner or by forming bona fide AMPA receptor-dependent neuron-to-glioma synapses. Moreover, these effects of neuronal activity on high-grade glioma growth are amplified by glioma-induced hyperexcitability of neurons.

To further elucidate the contribution of neuronal activity to central and peripheral nervous system tumor development, NF1 was studied herein, where affected individuals are prone to developing tumors intimately associated with nerves, including OPGs and pNFs. Using these preclinical models, it was previously demonstrated that different germline Nf1 mutations have dramatically different effects on plexiform neurofibroma and OPG formation in mice, suggesting that the specific NF1 germline mutation may regulate tumorigenesis at the level of non-neoplastic cells.

In this study, a common, naturally occurring NF1 missense mutation (c.5425C>T; p.Arg1809Cys) found in patients with NF1 who do not develop OPGs or neurofibromas was leveraged. Exploiting this unique mutation, a combination of human-induced pluripotent stem cell (hiPSC) and Nf1-mutant mouse lines were employed to demonstrate that central (retinal ganglion cells; RGCs) and peripheral (sensory neurons and dorsal root ganglion cells; DRGs) nervous system neurons support tumor growth by secreting paracrine factors necessary for tumor progression in an Nf1 mutation- and neuronal activity-dependent manner. In contrast to mice with other NF1 patient germline NF1 gene mutations, mice with the Arg1809Cys mutation, like NF1 patients with this mutation, do not form pNFs or OPGs and their DRGs and RGCs, respectively, do not exhibit the RAS-independent neuronal hyperexcitability seen in tumor-forming Nf1-mutant central and peripheral nervous system neurons. Based on prior studies revealing that the NF1 protein, neurofibromin, binds to and regulates hyperpolarization-activated cyclic nucleotide-gated (HCN) channels and that HCN channels directly modulate neuronal excitability, shown herein is that HCN channel dysregulation is responsible for Nf1-mutant central and peripheral nervous system neuronal hyperexcitability and consequently increased tumor-driving paracrine factor release, such that HCN channel targeting (using the anti-seizure medication lamotrigine) blocked Nf1-OPG progression in vivo. Moreover, demonstrated herein is that tumor-causing Nf1 mutations in neurons regulate neuronal production of paracrine factors through both visual experience (light)-evoked neuronal activity, as well as HCN channel dysregulation-mediated baseline neuronal hyperexcitability, highlighting the essential role of neuronal activity in NF1-associated nervous system tumor progression.

Results

Arg1809Cys Nf1-conditional mutant mice do not develop optic pathway gliomas.

The NF1 patient c.5425C>T p.Arg1809Cys NF1 mutation was engineered in mice on a C57Bl/6J background by CRISPR/Cas9 targeting and confirmed by direct sequencing. Wild-type (WT) and heterozygous Arg1809Cys Nf1-mutant mice (Nf1$^{+/1809}$) were born from heterozygous Nf1$^{+/1809}$ parents with the expected Mendelian ratios (see e.g., FIG. 1A). However, no homozygous Nf11809/1809 mice were born, suggesting embryonic lethality, as seen with conventional Nf1 knockout mice. Heterozygous mice had similar weights as WT littermate controls and two genetically engineered mouse (GEM) strains harboring different patient-derived germline Nf1 gene mutations (c.2041C>T, p.R681X35,36; c.3827G>C, p.R1276P43) (see e.g., FIG. 1B).

Figures 2A, 2B:
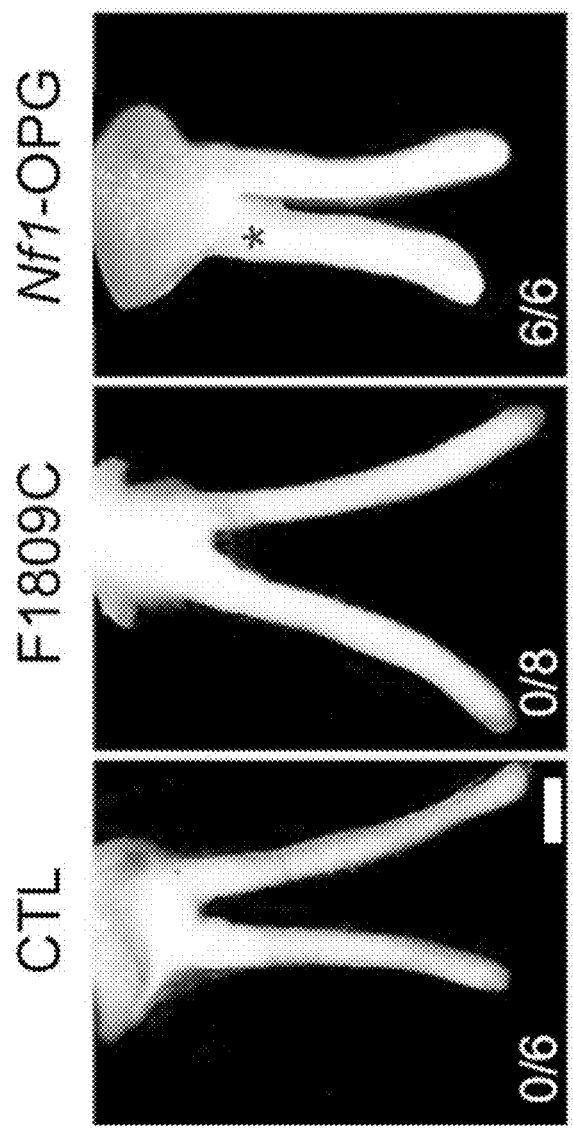
FIG. 2A-FIG. 2D shows an exemplary embodiment of Arg1809Cys Nf1-mutant mice do not develop optic gliomas following somatic Nf1 inactivation in accordance with the present disclosure.
Figure 2C:
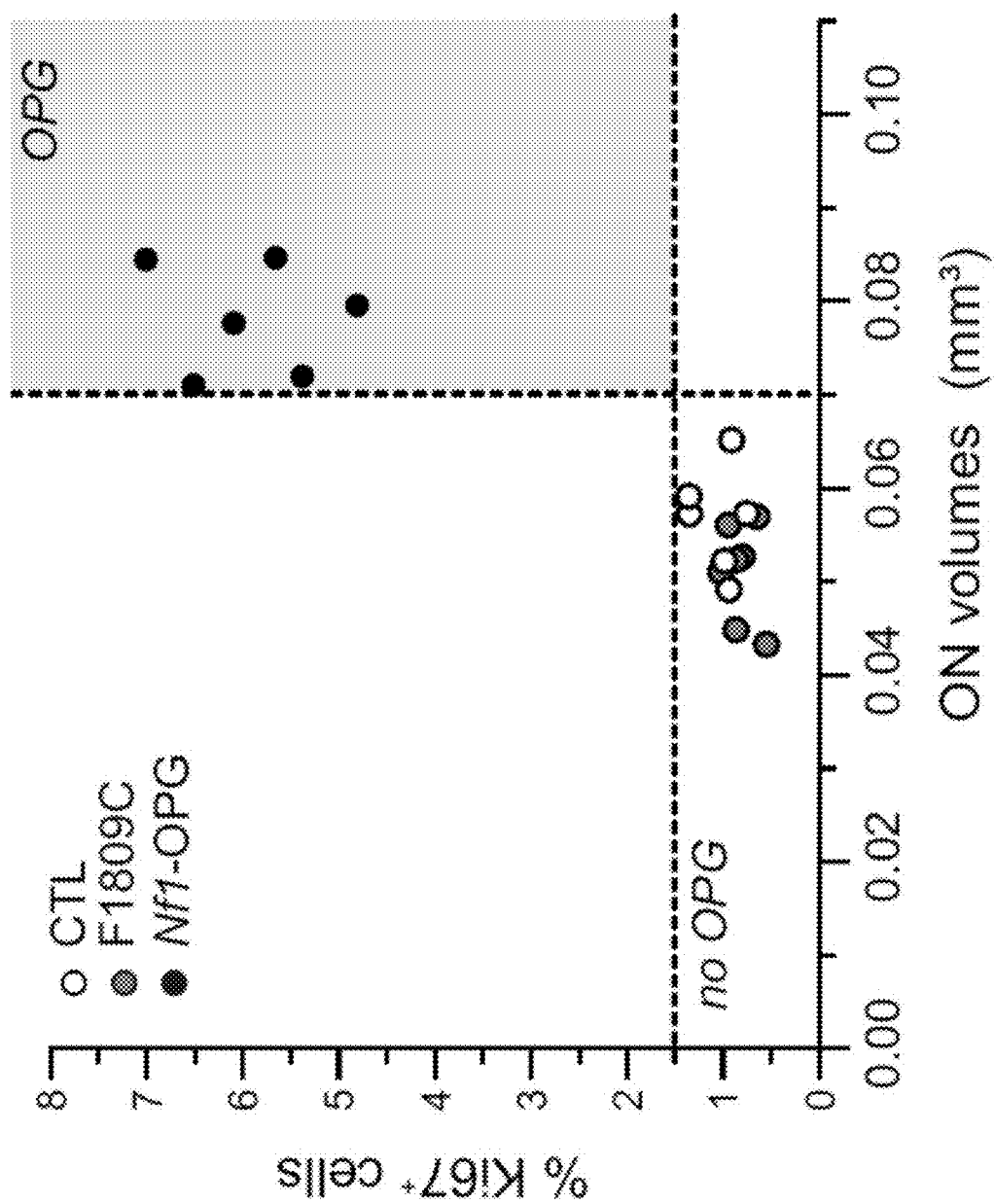
Figure 2D:
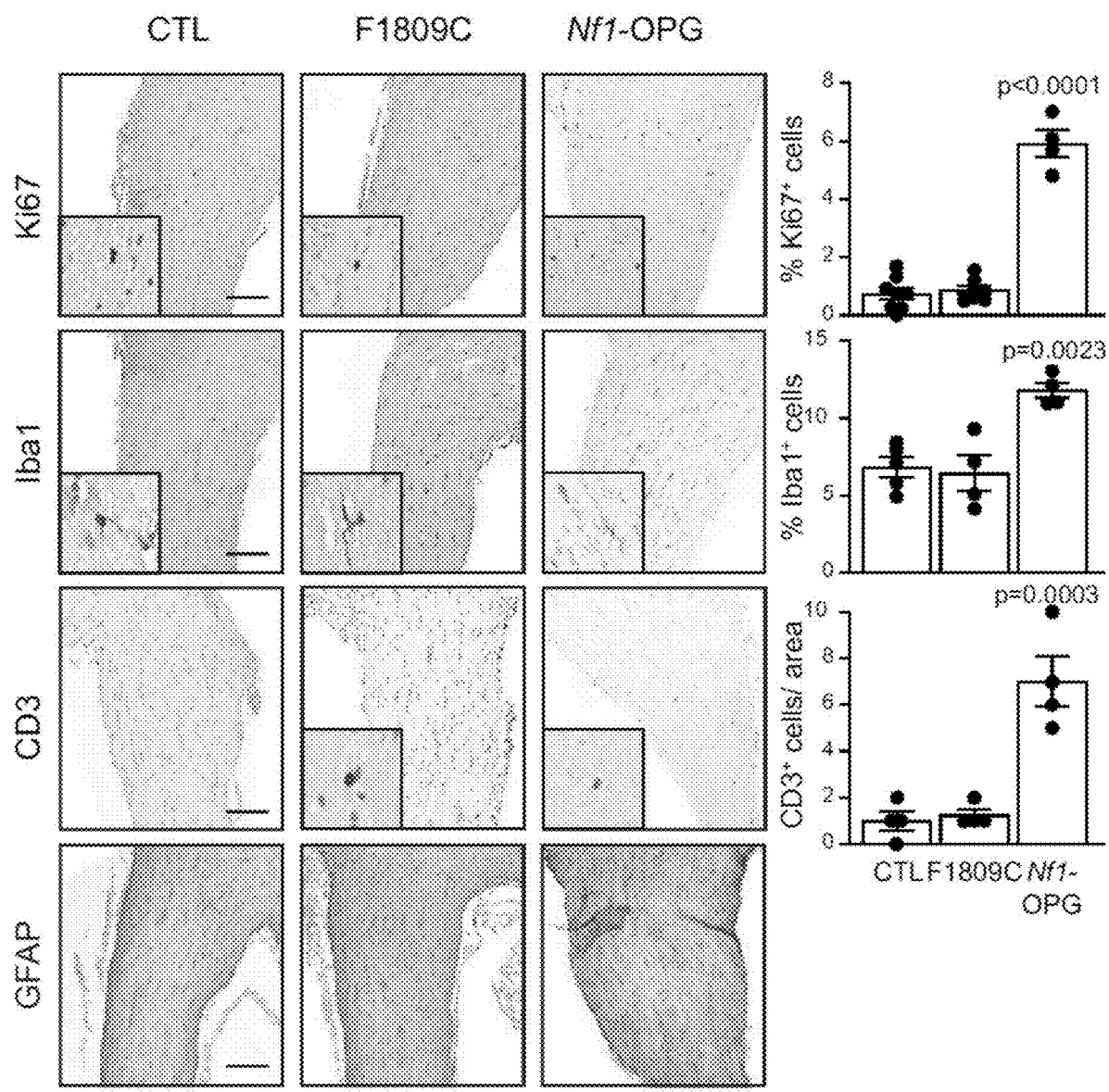

Like patients with the R1809C germline NF1 gene mutation who lack OPGs (see e.g., FIG. 2A), mice harboring a germline Nf1$^{R1809C}$ mutation with somatic loss of Nf1 in neuroglial progenitor cells, the optic glioma initiating cells (Nf1$^{f/1809}$; hGFAP-Cre mice (F1809C)), did not develop OPGs at 3 months of age (0/8; see e.g., FIG. 2B). In contrast, all Nf1$^{f/neo}$; hGFAP-Cre mice (Nf1-OPG), where the germline Nf1 inactivation results from the insertion of a neomycin cassette into exon 31 of the Nf1 gene, developed OPGs (6/6) with increased optic nerve volumes (0.079 mm$^3$; see e.g., FIG. 2C), proliferative indices (5.9% Ki67$^+$ cells), microglia (11.8% Iba1$^+$ cells), T cells (7 CD3$^+$ cells) and GFAP+ cells, as previously reported (see e.g., FIG. 2D). Importantly, optic nerves from Nf1$^{f/1809}$; hGFAP-Cre mice were indistinguishable from Nf1$^{f/f}$ controls (CTL) with respect to optic nerve volume (Nf1$^{f/1809}$; hGFAP-Cre, 0.05 mm$^3$ CTL, 0.057 mm$^3$), proliferative index (Nf1$^{f/1809}$; hGFAP-Cre, 0.8%; CTL, 1.03 Ki67$^+$ cells), microglia content (Nf1$^{f/1809}$; hGFAP-Cre, 6.4%; CTL, 6.8% Iba1$^+$ cells), T-cell content (Nf1$^{f/1809}$; hGFAP-Cre, 1.2; CTL, 1 CD3$^+$ cells) and GFAP immunoreactivity (see e.g., FIG. 2C-FIG. 2D). Taken together, these findings demonstrate that mice with the Arg1809Cys germline Nf1 mutation, like their human counterparts, do not develop OPGs.

OPG-Associated Nf1-Mutant CNS Neurons are Hyperexcitable.

Figure 3A:
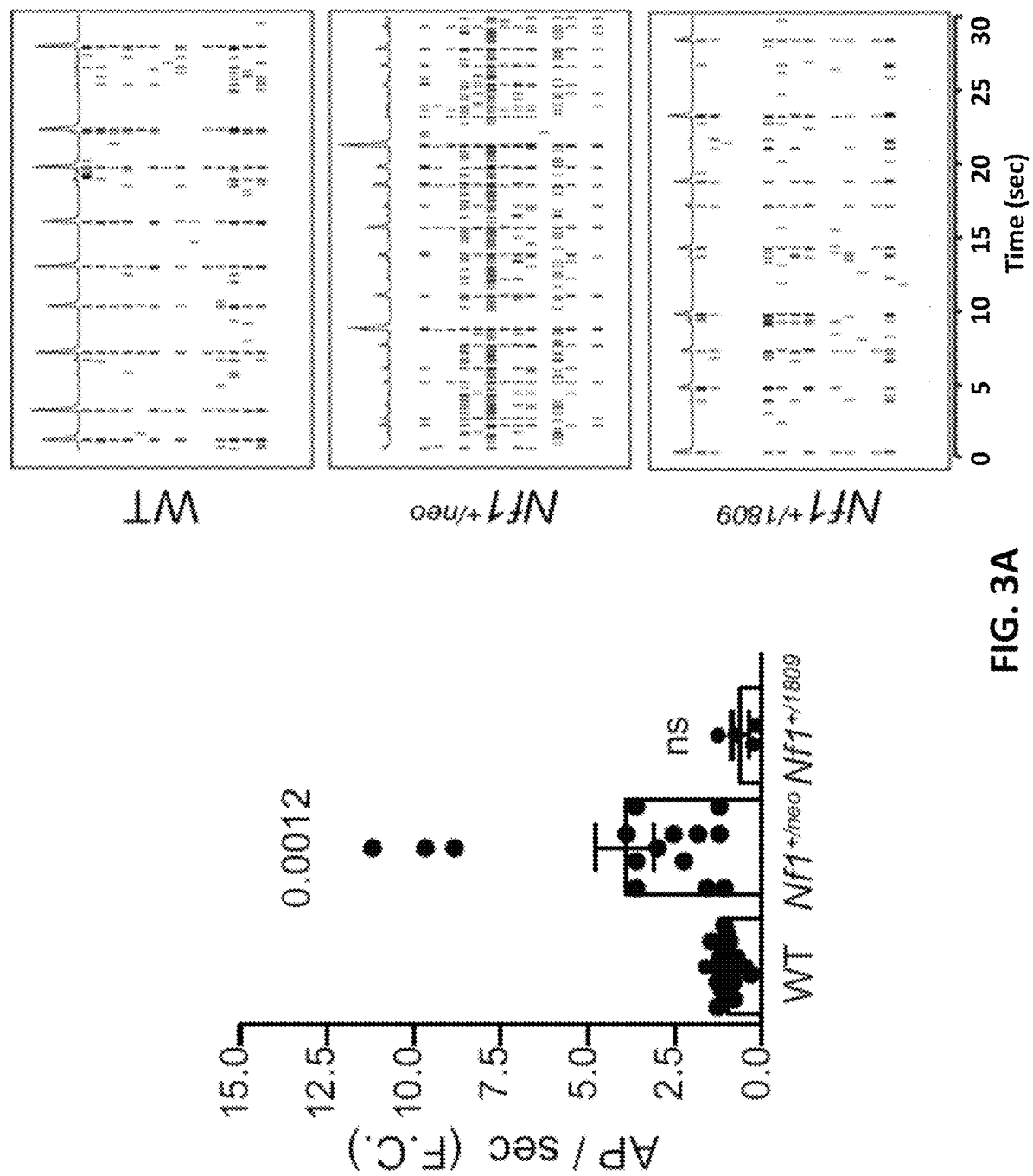
FIG. 3A-FIG. 3C shows an exemplary embodiment of OPG-associated Nf1-mutant neurons have increased activity and OPG-promoting factor production in accordance with the present disclosure.
Figures 3B, 3C:
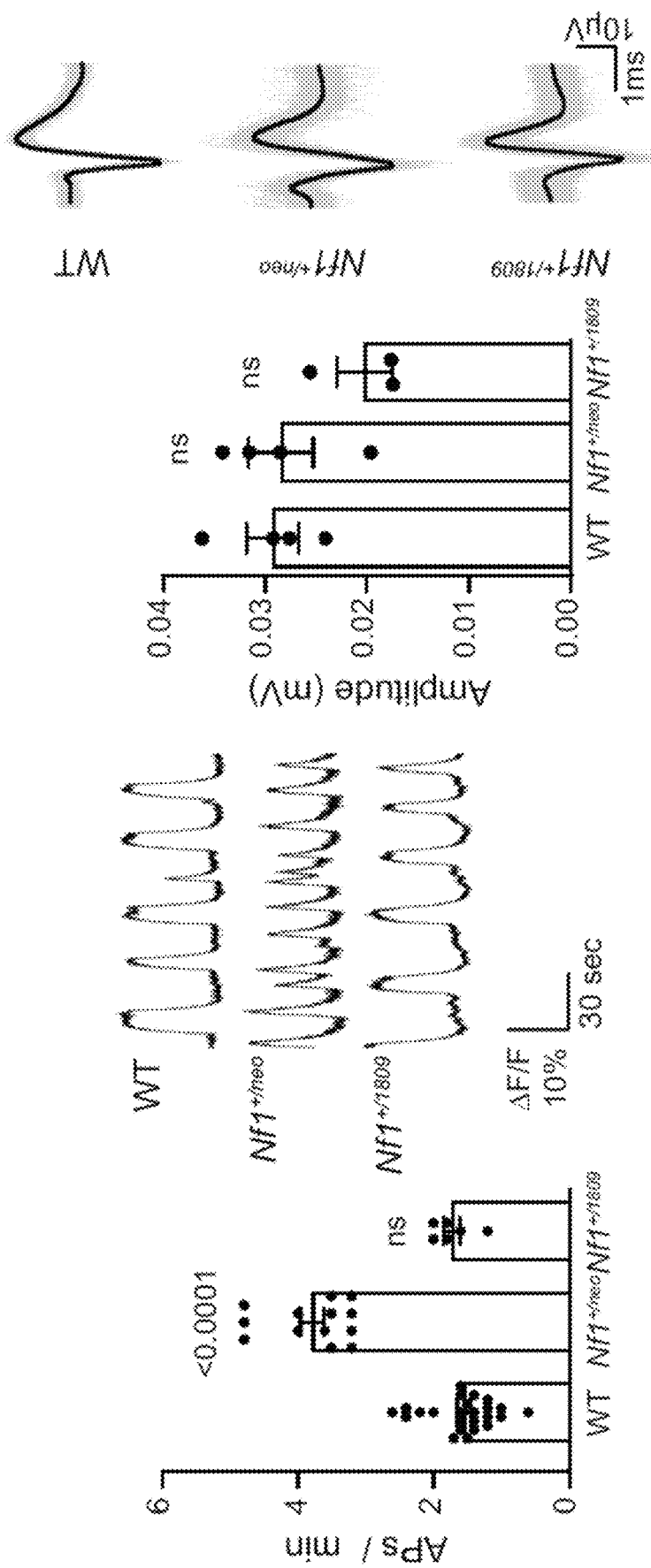

Prior studies have shown that OPG growth in Nf1-mutant mice (Nf1$^{f/neo}$; hGFAP-Cre) is initiated by neuronal activity-dependent paracrine signaling. In these mice, neuroligin-3 (Nlgn3) is shed in the Nf1-mutant (Nf1$^{+/neo}$) optic nerve in an activity-dependent manner, such that genetic or pharmacological blockade of Nlgn3 shedding inhibits glioma initiation and progression. Based on these findings, the neuronal activity of primary WT, Nf1$^{+/neo}$, and Nf1$^{+/1809}$ RGCs was first examined using multi-electrode arrays (see e.g., FIG. 3A) or calcium imaging (see e.g., FIG. 3B) after 10 days in vitro. The Nf1$^{+/neo}$, but not the Nf1$^{+/1809}$, neurons had increased activity relative to WT RGCs, as measured by action potential (AP) firing rates (2.5-3.9-fold increase relative to WT control; see e.g., FIG. 3A-FIG. 3B). No change in neuronal action potential amplitudes were noted in Nf1$^{+/neo}$ or Nf1$^{+/1809}$ neurons relative to WT controls (see e.g., FIG. 3C). This suggests that Nf1 mutations associated with tumor formation cause RGC neurons to be hyperexcitable.

OPG-Associated Nf1-Mutant CNS Neurons Secrete Tumor-Promoting Factors in an Activity-Dependent Manner.

Figure 4:
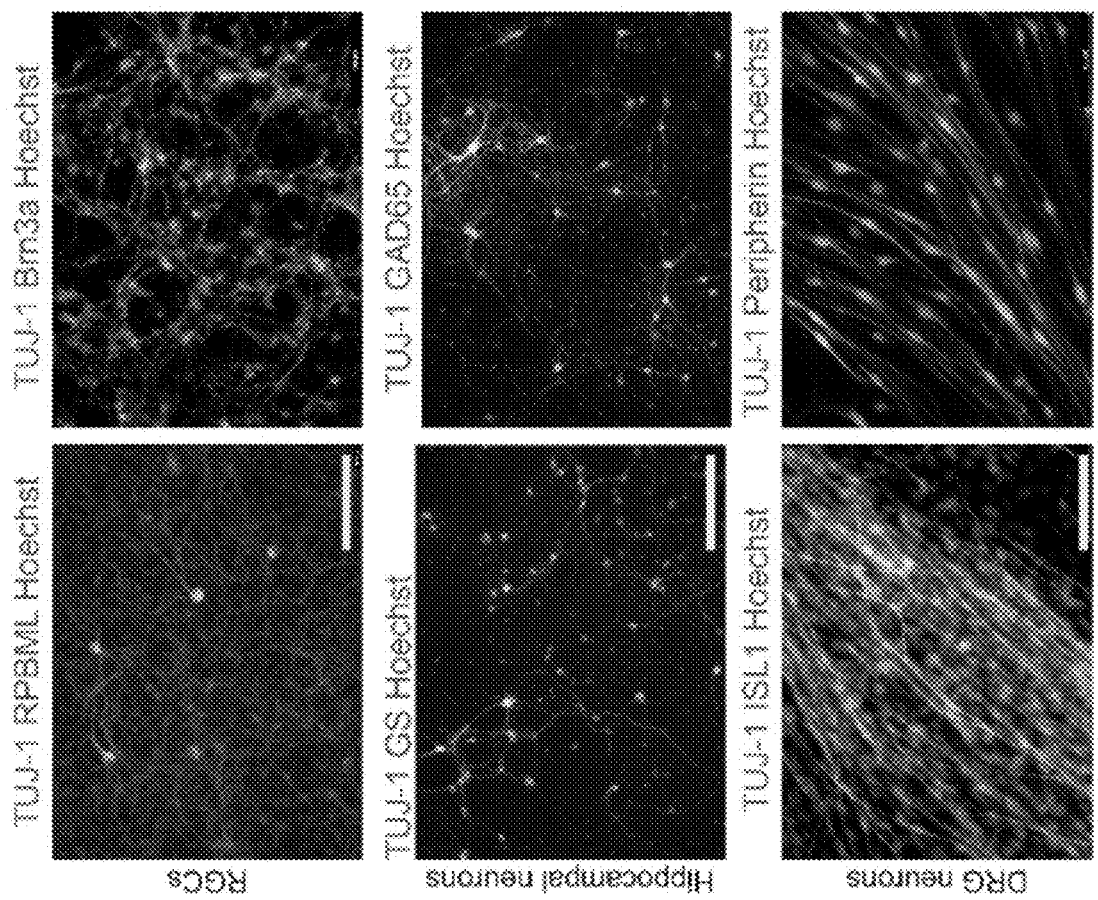
FIG. 4 shows an exemplary embodiment of analysis of Arg1809Cys Nf1-mutant neuron signaling in accordance with the present disclosure.
Figure 5A:
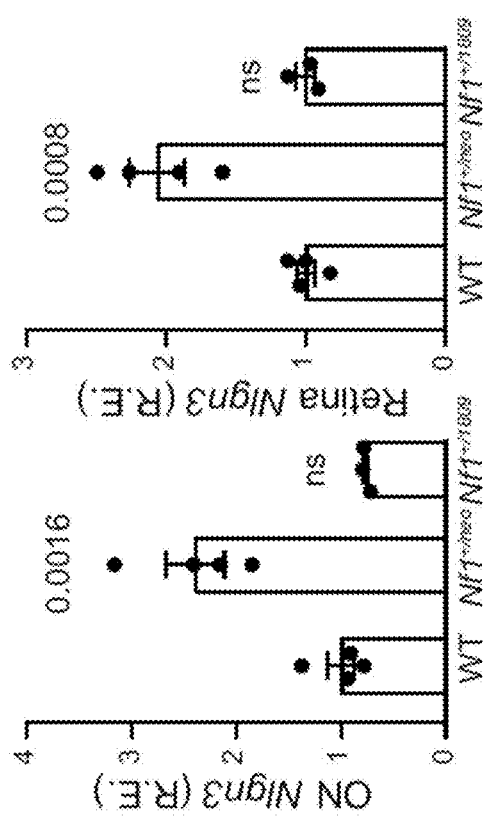
FIG. 5A-FIG. 5F shows an exemplary embodiment of OPG-associated Nf1-mutant neurons have increased activity and OPG-promoting factor production in accordance with the present disclosure.
Figure 5B:
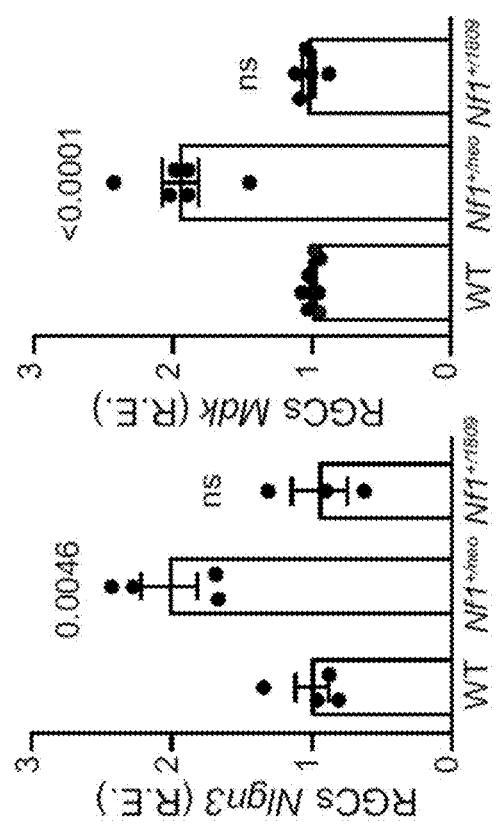
Figure 5C:
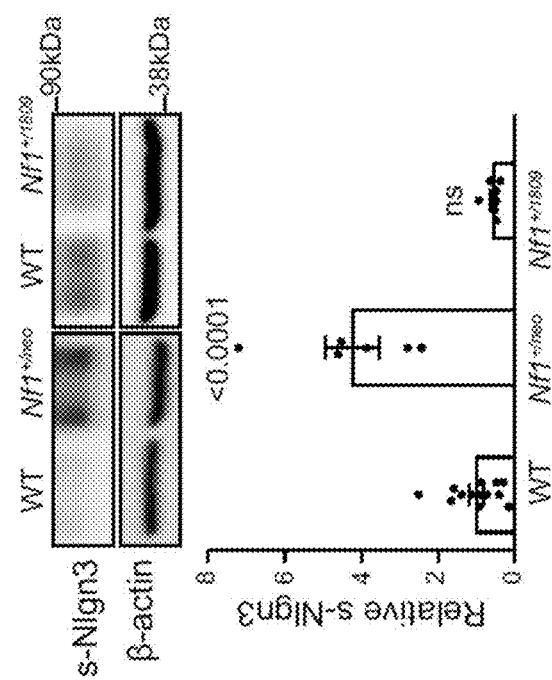
Figure 5D:
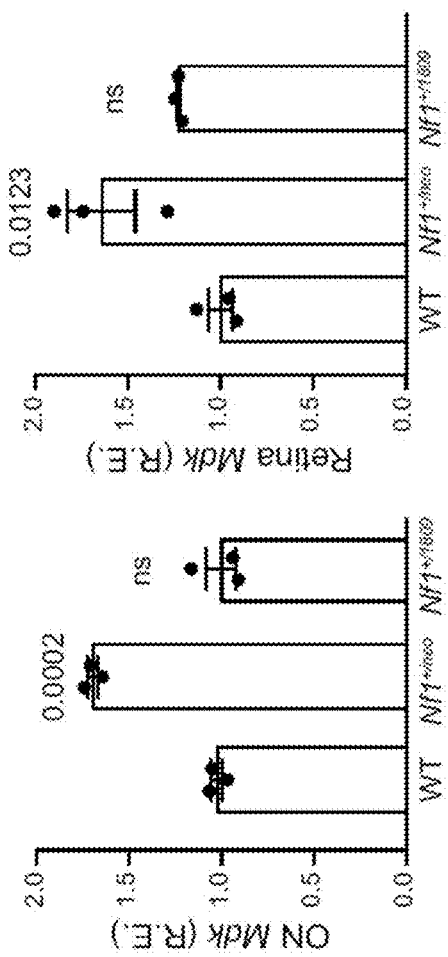
Figure 5E:
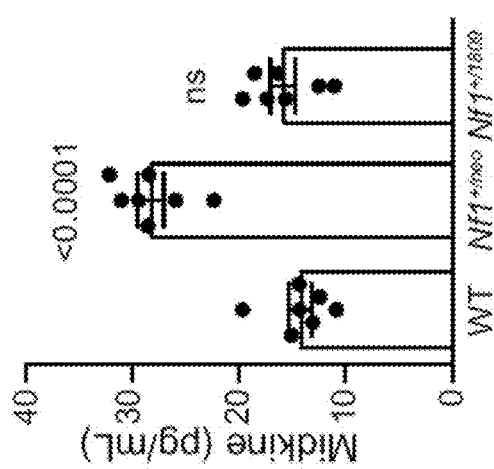
Figure 5F:
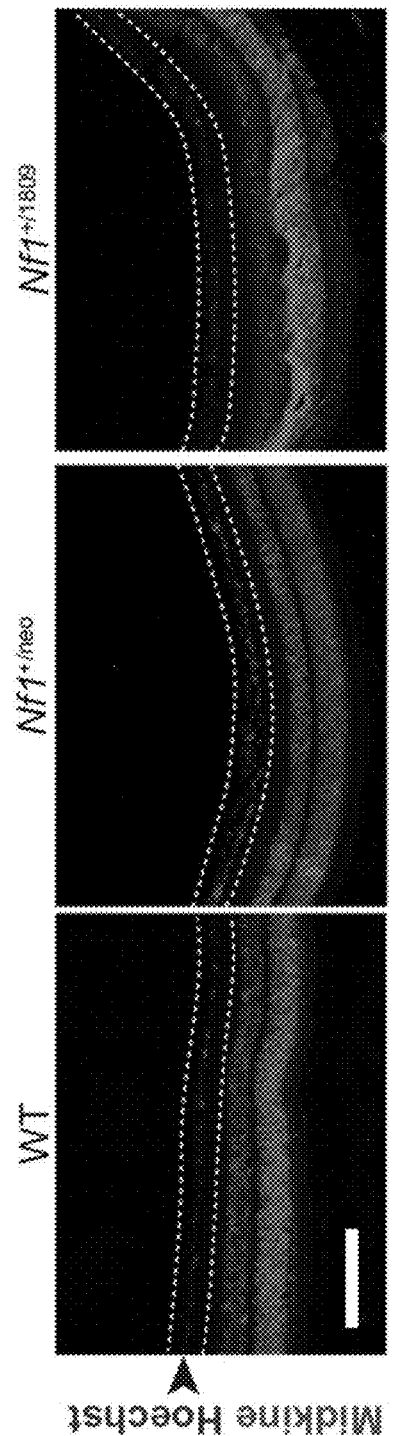
Figure 6:
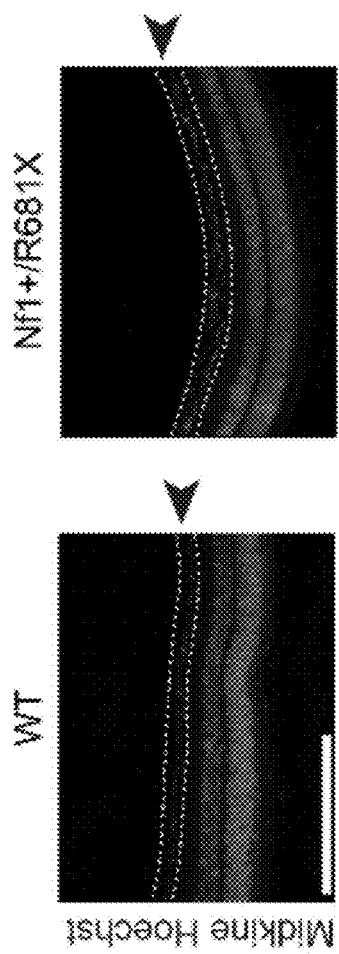
FIG. 6 shows an exemplary embodiment of analysis of Arg1809Cys Nf1-mutant neuron signaling in accordance with the present disclosure.
Figure 7A:
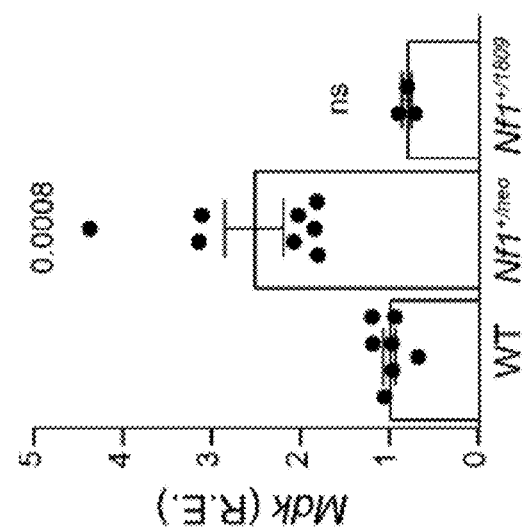
FIG. 7A-FIG. 7C shows an exemplary embodiment of Nf1-mutant hippocampal neuron Midkine secretion is dependent on neuronal hyperexcitability in accordance with the present disclosure.
Figure 7C:
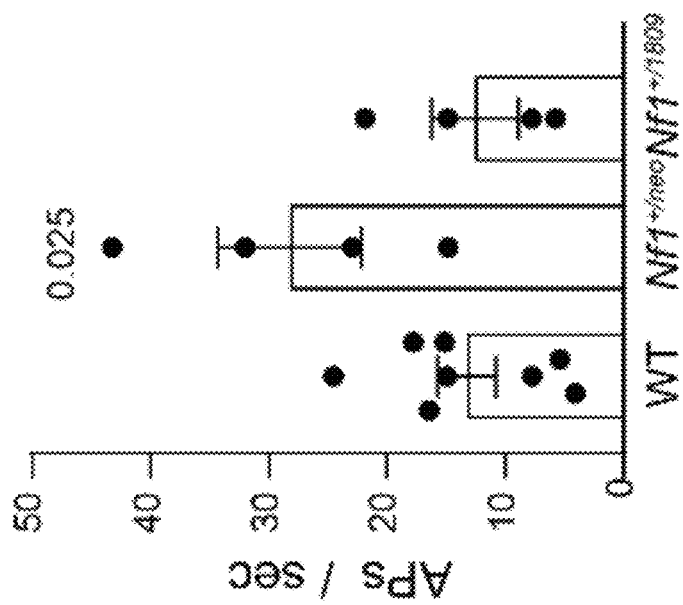
Figure 7B:
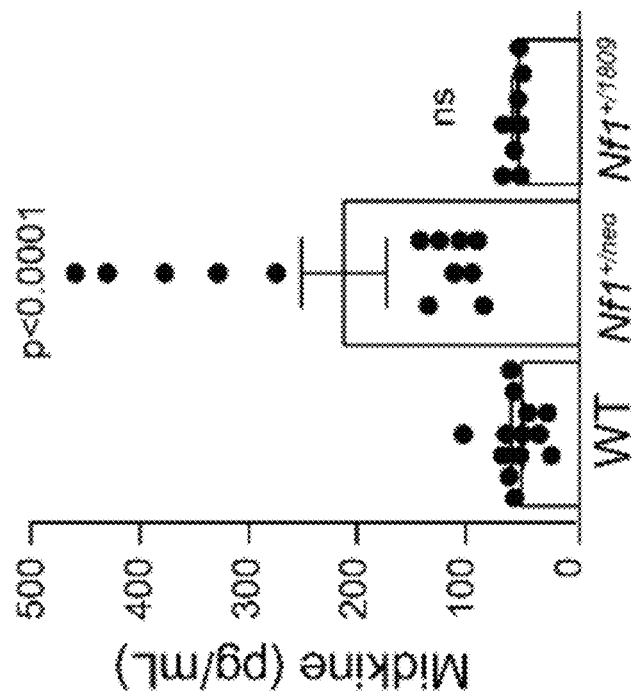

To determine whether increased RGC activity triggers the secretion of the two known neuronal OPG-promoting factors, Nlgn3 and midkine, their transcript and protein expression levels were assessed both in vitro and in vivo. Optic nerves (ONs), RGCs (see e.g., FIG. 4), and RGCs within the intact retinae from Nf1$^{+/neo}$, but not Nf1$^{+/1809}$, mice had increased expression of Nlgn3 RNA (2.0-2.3-fold increase; see e.g., FIG. 5A-FIG. 5B), soluble cleaved Nlgn3 protein (s-Nlgn3; see e.g., FIG. 5C), Mdk RNA (1.6-fold increase; see e.g., FIG. 5D) and midkine protein (2.2-fold increase; see e.g., FIG. 5E-FIG. 5F) expression relative to WT controls. Increased midkine expression was also detected in RGCs from Nf1$^{+/R681X}$-mutant mice (see e.g., FIG. 6), another mouse strain that develops optic gliomas following somatic Nf1 inactivation in neuroglial progenitors, as well as in Nf1$^{+/neo}$, but not Nf1$^{+/1809}$, mouse primary hippocampal neurons (see e.g., FIG. 4 and FIG. 7A-FIG. 7B). In addition, hippocampal neurons from Nf1$^{+/neo}$ mice similarly exhibited hyperexcitability (see e.g., FIG. 7C).

Figure 9:
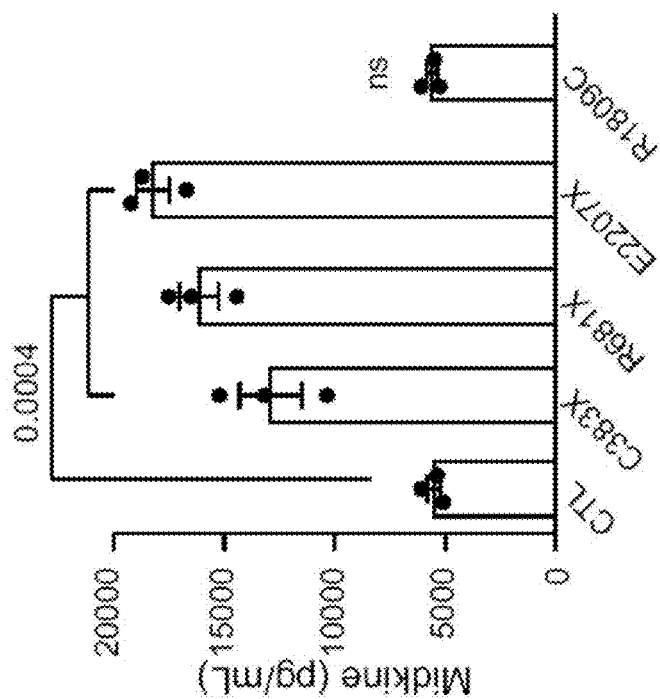
FIG. 9 shows an exemplary embodiment of OPG-associated Nf1-mutant neurons have increased activity and OPG-promoting factor production in accordance with the present disclosure.
Figure 8:
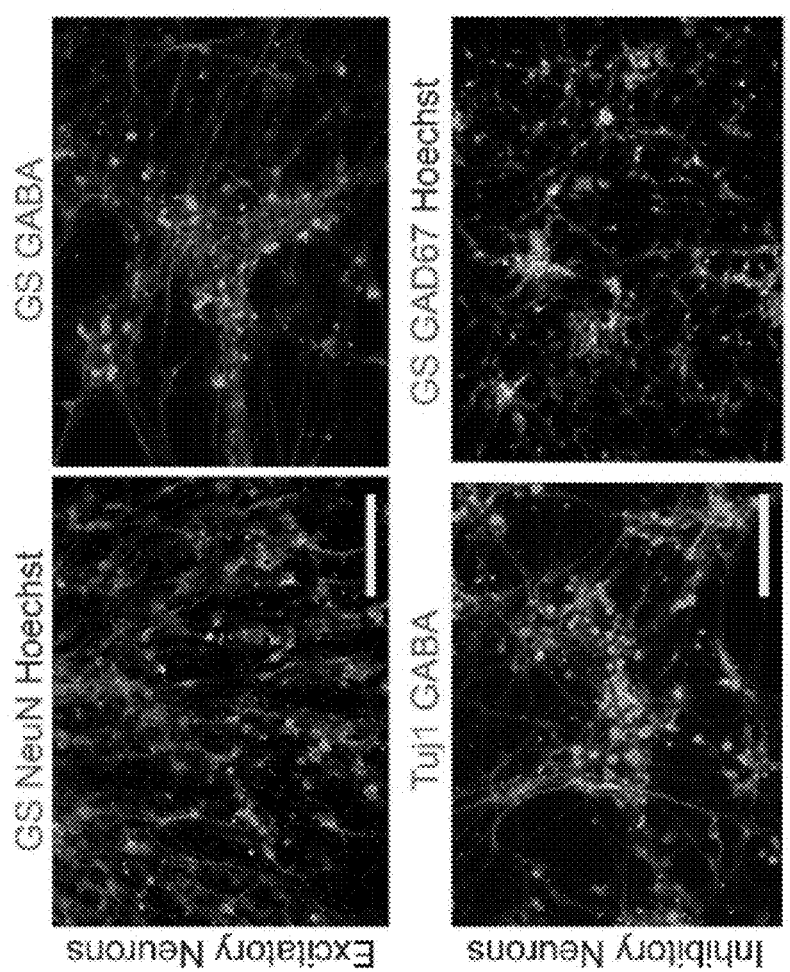
FIG. 8 shows an exemplary embodiment of analysis of Arg1809Cys Nf1-mutant neuron signaling in accordance with the present disclosure.
Figure 11A:
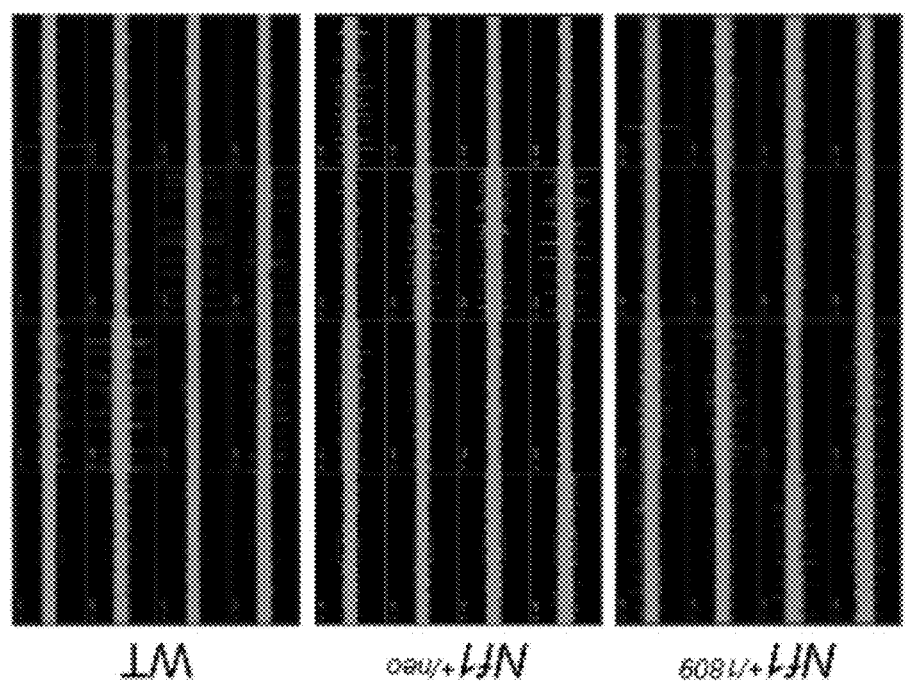
FIG. 11A-FIG. 11I shows an exemplary embodiment of analysis of Arg1809Cys Nf1-mutant neuron signaling in accordance with the present disclosure.
Figure 10:
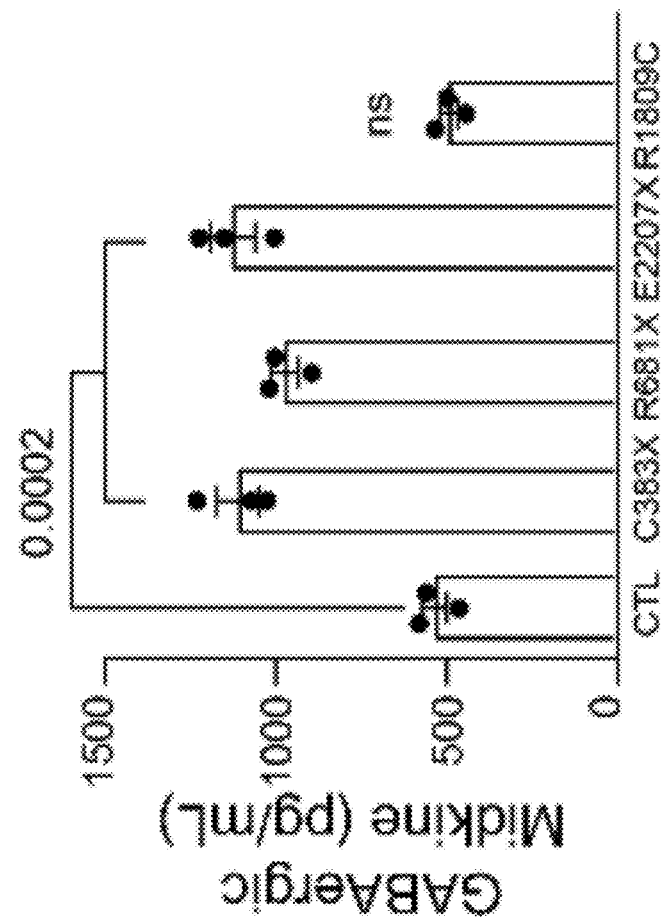
FIG. 10 shows an exemplary embodiment of analysis of Arg1809Cys Nf1-mutant neuron signaling in accordance with the present disclosure.
Figures 11B, 11C, 11D:
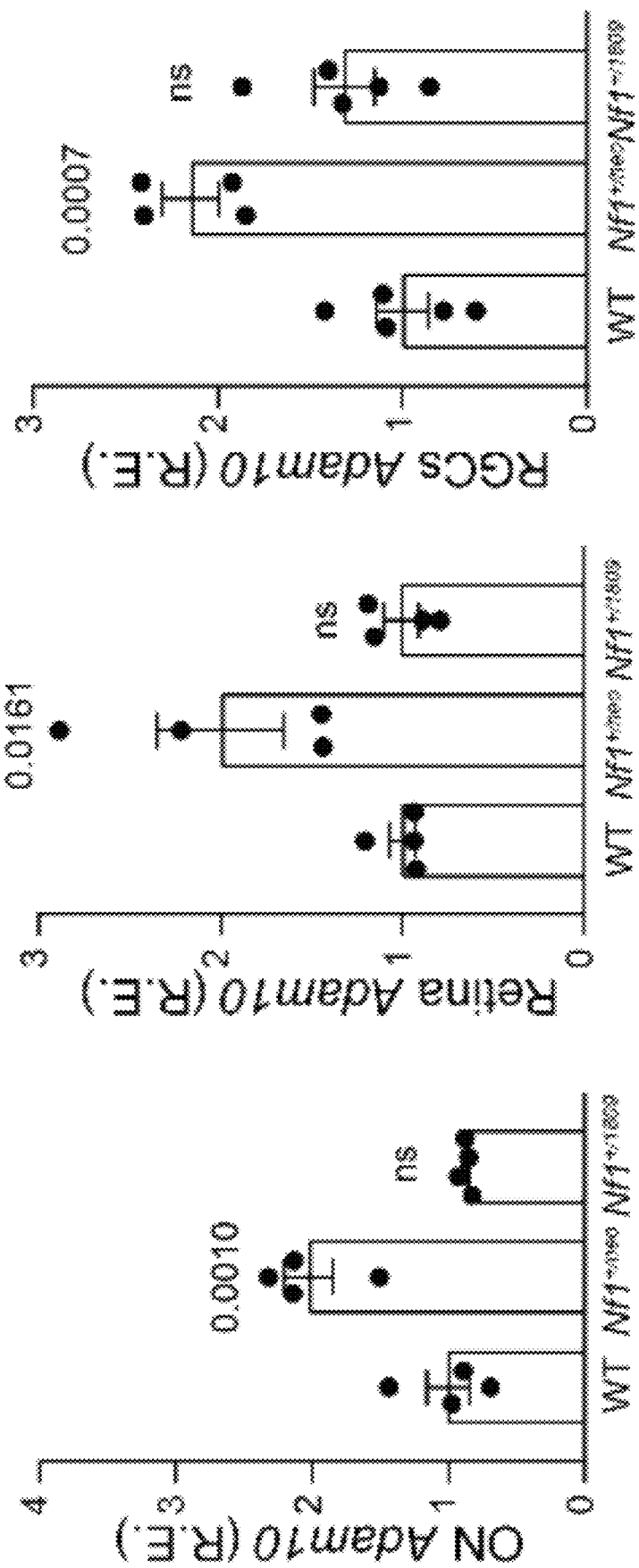
Figure 11G:
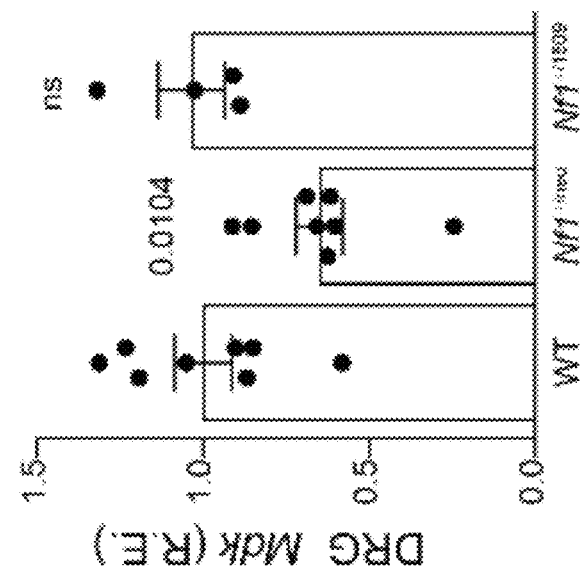
Figure 11F:
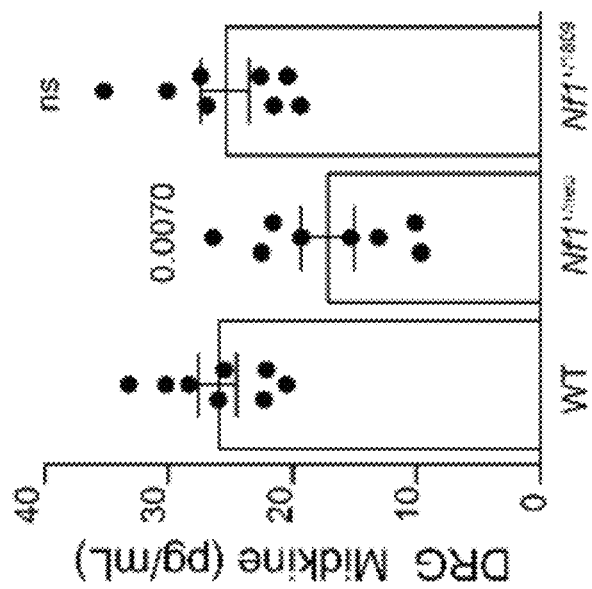
Figure 11E:
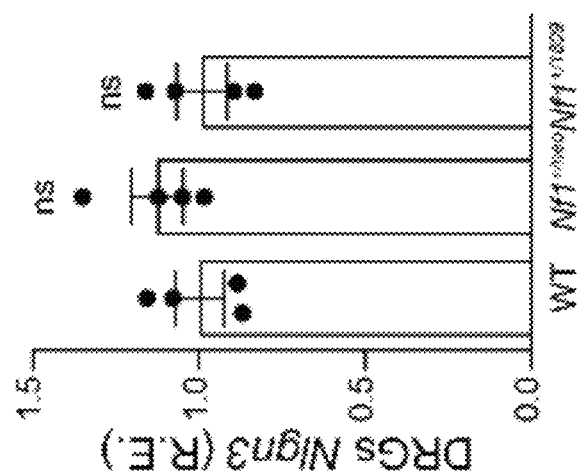

The correlation between neuronal midkine production and tumor risk is reinforced in human iPSC-derived central nervous system neurons (see e.g., FIG. 8). Midkine expression is increased both in excitatory (see e.g., FIG. 9) and inhibitory (see e.g., FIG. 10) neurons harboring NF1 mutations that are found in NF1 patients that develop OPGs (c.1149 C>A, p.Cys381X; c.2041 C>T, pArg681X; c.6619 C>T, p.Gln2207X), but not in NF1$^{+/R1809C}$ neurons, relative to controls (CTL). Similarly, Adam10 transcript expression was only increased in Nf1$^{+/neo}$, but not in Nf1$^{+/1809}$, mouse retinae, ONs, and RGCs (see e.g., FIG. 11A-FIG. 11D). In contrast, neither Nf1$^{+/neo}$ nor Nf1$^{+/1809}$ PNS (DRG) sensory neurons had increased Nlgn3 (see e.g., FIG. 11E) or midkine (see e.g., FIG. 11F-FIG. 11G) expression relative to WT controls, highlighting the selective upregulation of Nlgn3 and midkine in CNS, rather than in PNS, neurons.

Figures 11H, 11I:
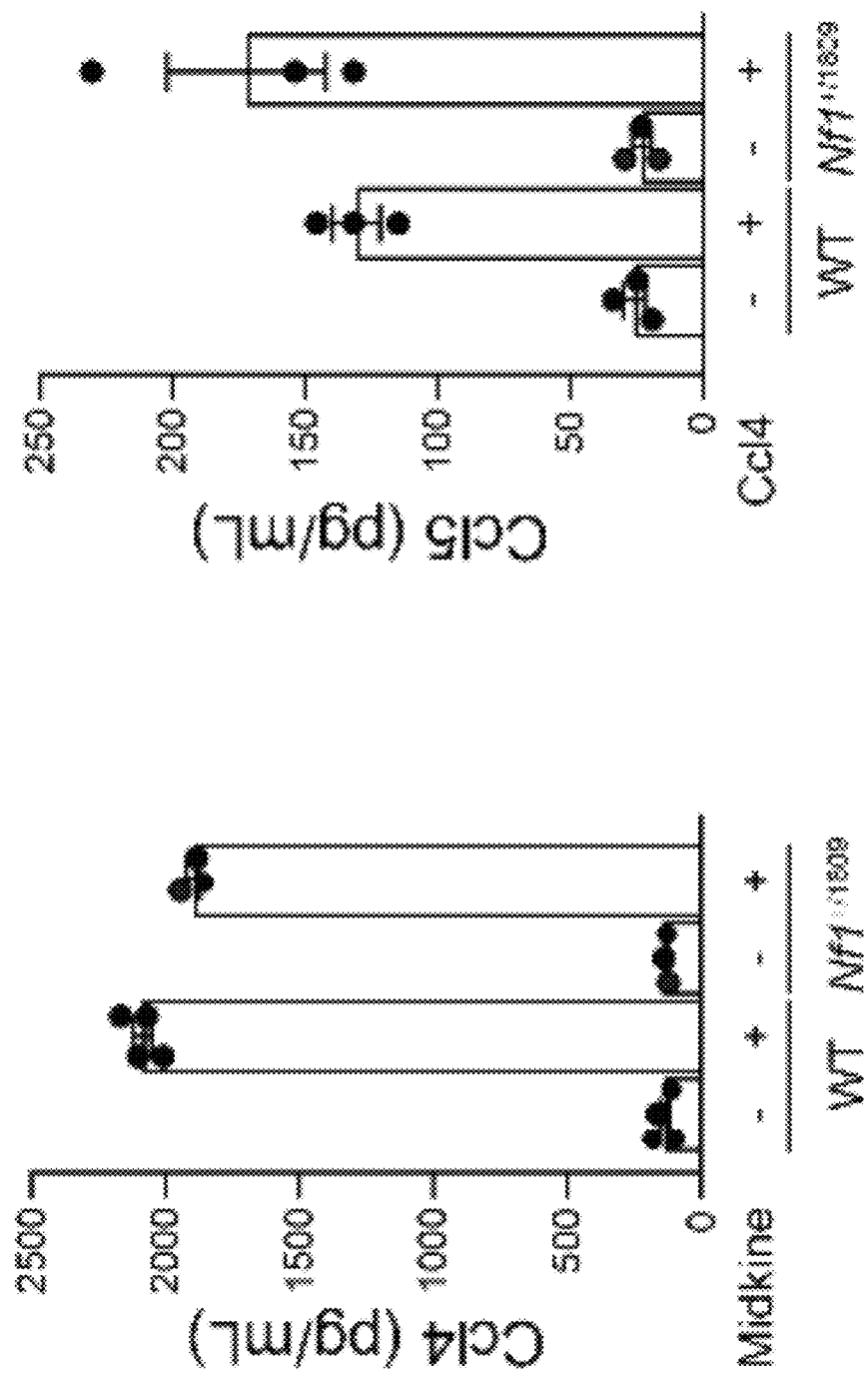
Figure 12A:
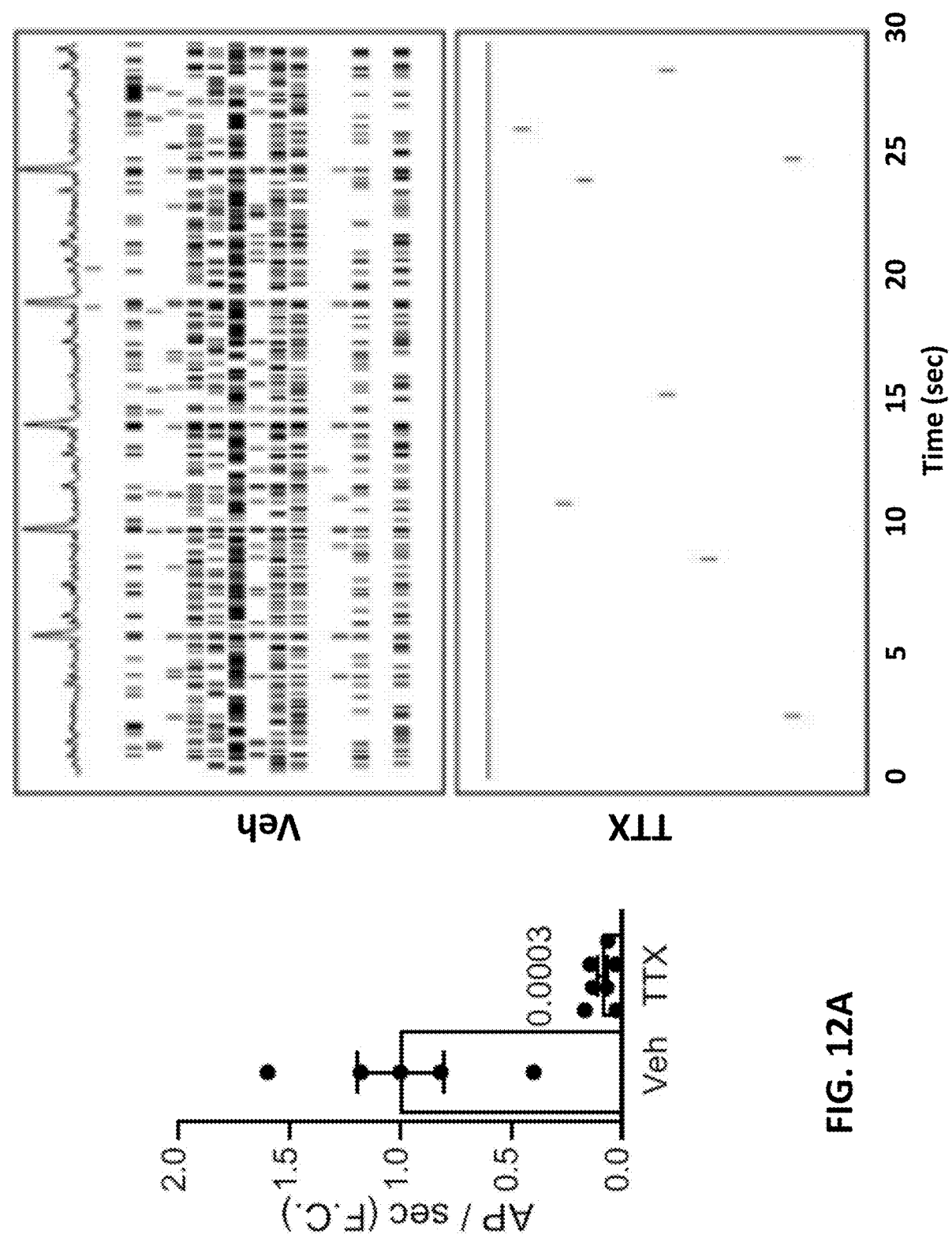
FIG. 12A-FIG. 12C shows an exemplary embodiment of OPG-associated Nf1-mutant neurons have increased activity and OPG-promoting factor production in accordance with the present disclosure.
Figure 12B:
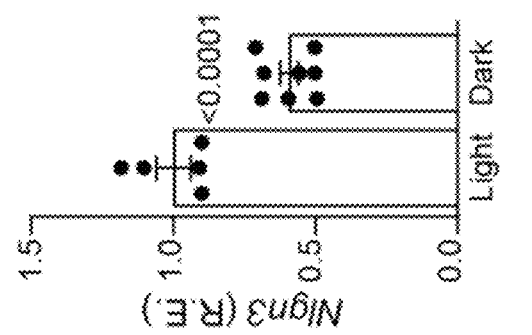
Figure 12C:
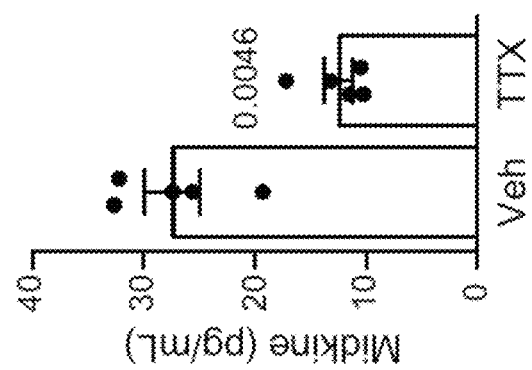

As part of a neuron-immune-cancer cell axis in Nf1-OPG, Nf1-mutant neurons secrete midkine to induce T-cell Ccl4 expression, which in turn, results in microglial elaboration of Ccl5, an obligate OPG growth factor. To ascertain whether this molecular circuitry is intact in mice harboring the Nf1$^{+/1809}$ mutation, and to exclude defects in other stromal cells (T cells and microglia) that might be additionally responsible for the observed lack of optic gliomas in Nfl$^{f/1809}$; hGFAP-Cre mice, the ability of Nfl$^{+/1809}$ T cells and microglia to secrete Ccl4 in response to midkine and Ccl5 in response to Ccl4 was examined, respectively (see e.g., FIG. 11H-FIG. 11I). Both Nfl$^{+/1809}$ T cells and microglia responded to midkine and Ccl4, respectively, similar to their Nfl$^{+/neo}$ counterparts. Therefore, the lack of OPG formation likely reflects the failure of Nfl$^{+/1809}$ neurons to produce glioma-promoting trophic factors. Importantly, blockade of Nfl$^{+/neo}$ neuronal activity with 1 µM tetrodotoxin (TTX) (>80-fold decrease; see e.g., FIG. 12A-FIG. 12B) reduced midkine levels (1.9-fold decrease; see e.g., FIG. 12C), similar to TTX effects on Nlgn3, confirming that both Nlgn3 and midkine secretion are neuronal activity-dependent and reversible by pharmacological treatment.

HCN Channel Activity Regulates Midkine Production in OPG-Associated Nfl RGCs.

Figure 13A:
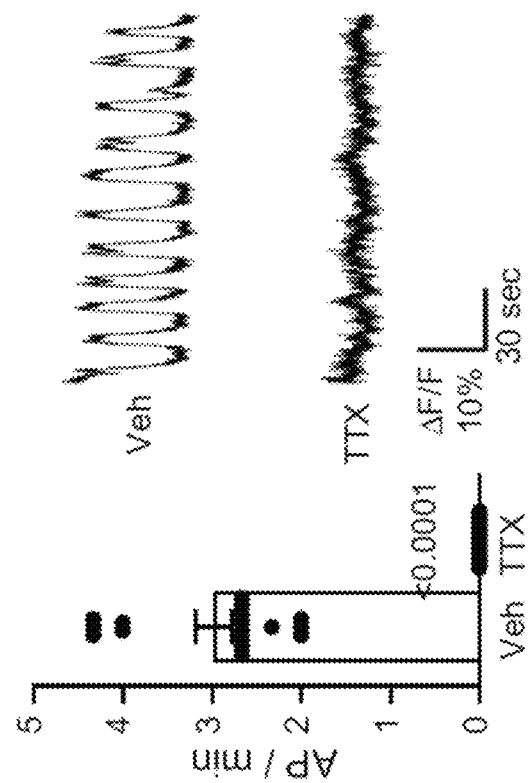
FIG. 13A-FIG. 13C shows an exemplary embodiment of OPG-associated Nf1-mutant neuronal hyperexcitability is HCN channel-dependent in accordance with the present disclosure.
Figure 13C:
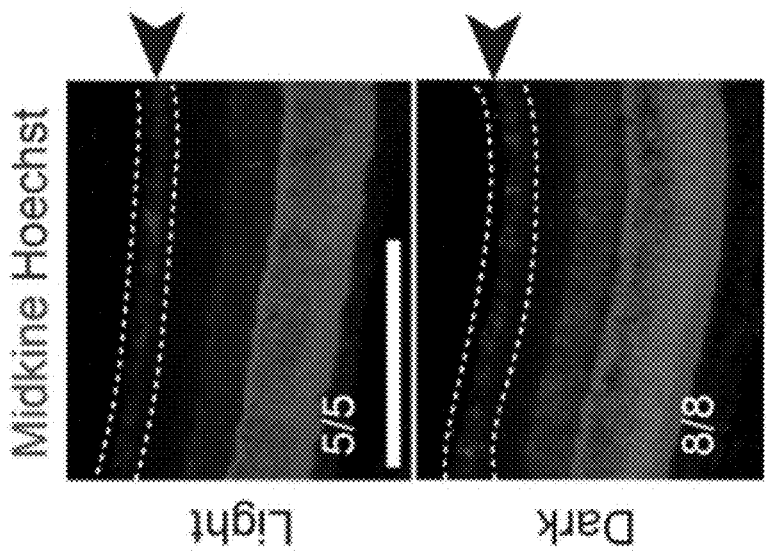
Figure 13B:
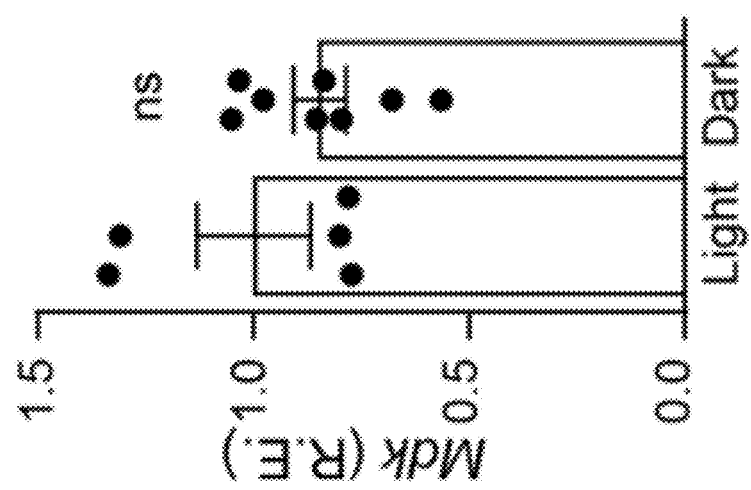
Figure 14:
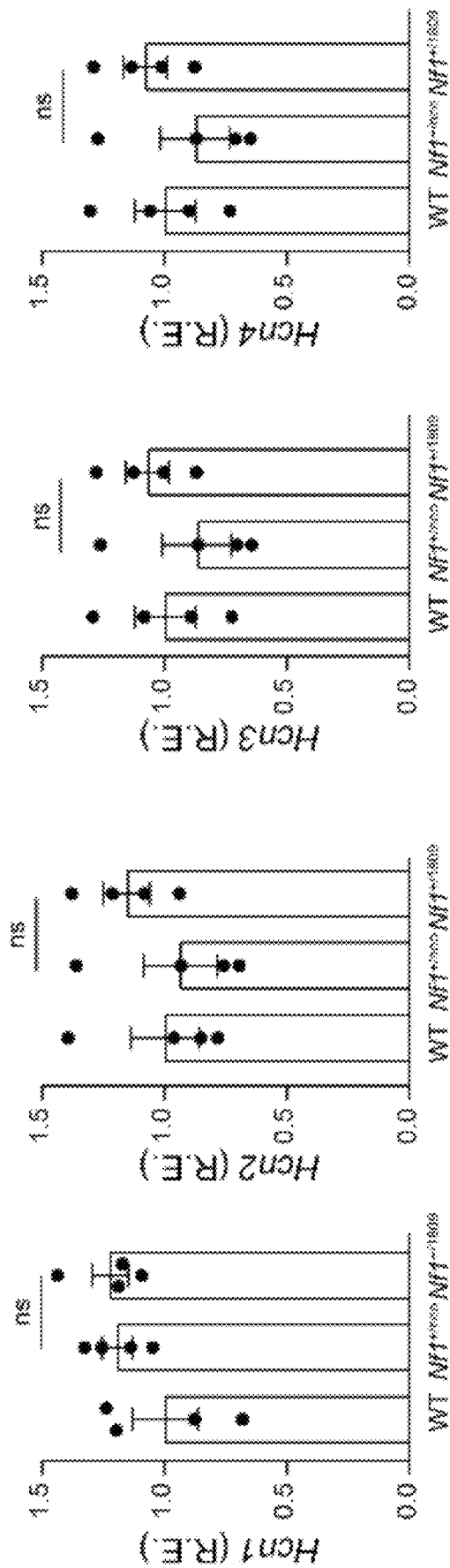
FIG. 14 shows an exemplary embodiment of analysis of Arg1809Cys Nf1-mutant neuron signaling in accordance with the present disclosure.
Figure 15A:
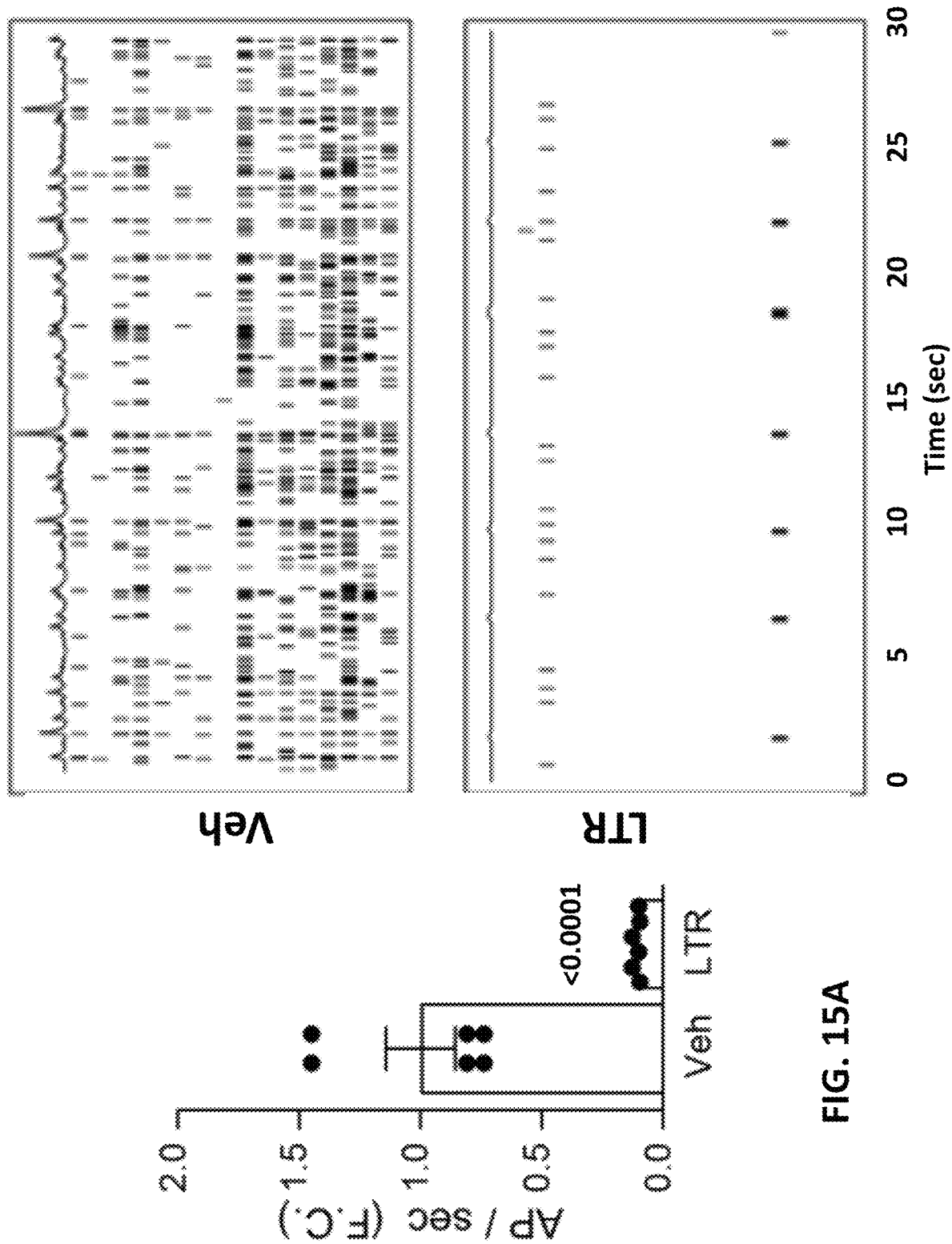
FIG. 15A-FIG. 15C shows an exemplary embodiment of OPG-associated Nf1-mutant neuronal hyperexcitability is HCN channel-dependent in accordance with the present disclosure.
Figure 15B:
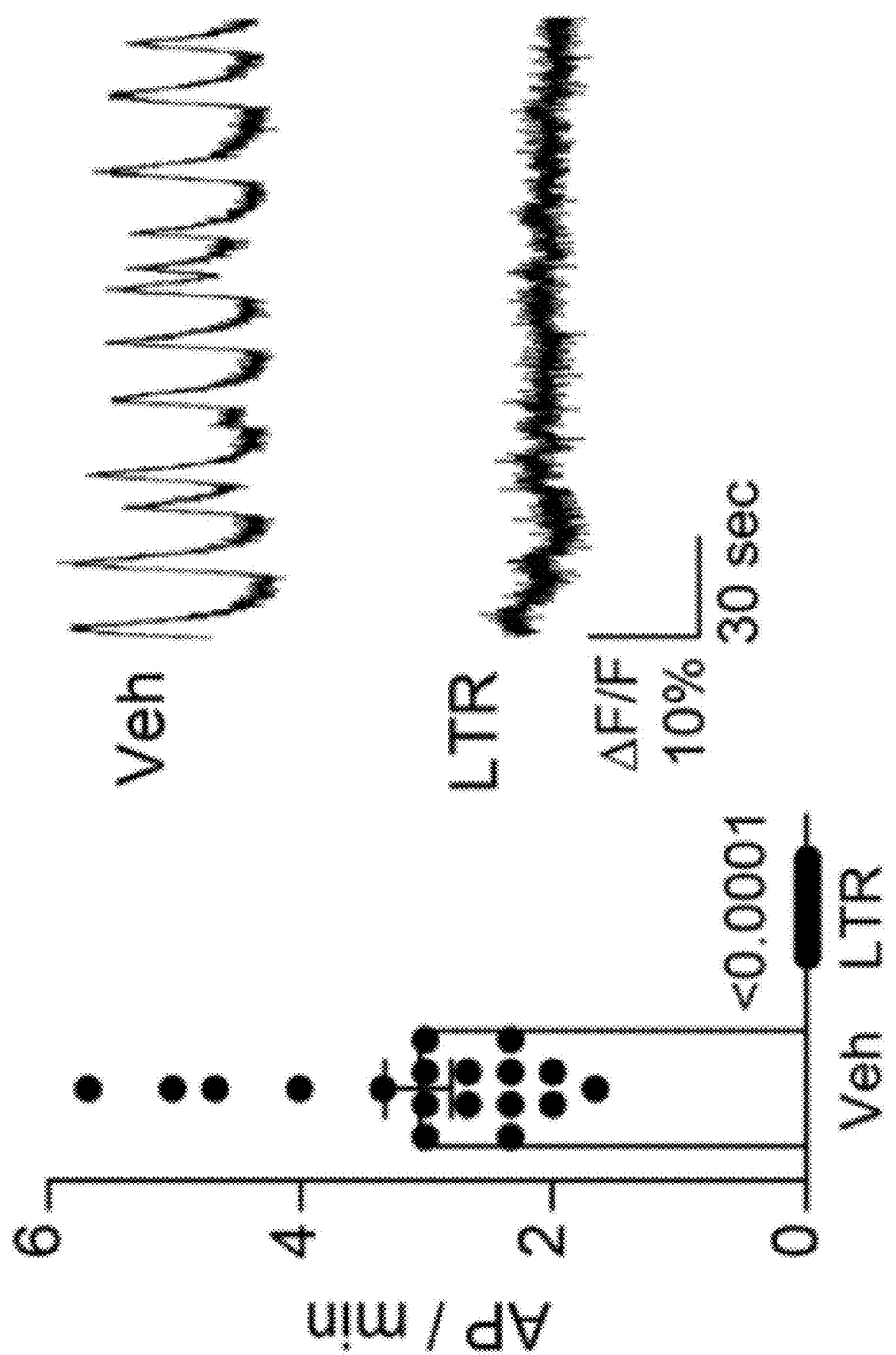
Figures 15C, 16A:
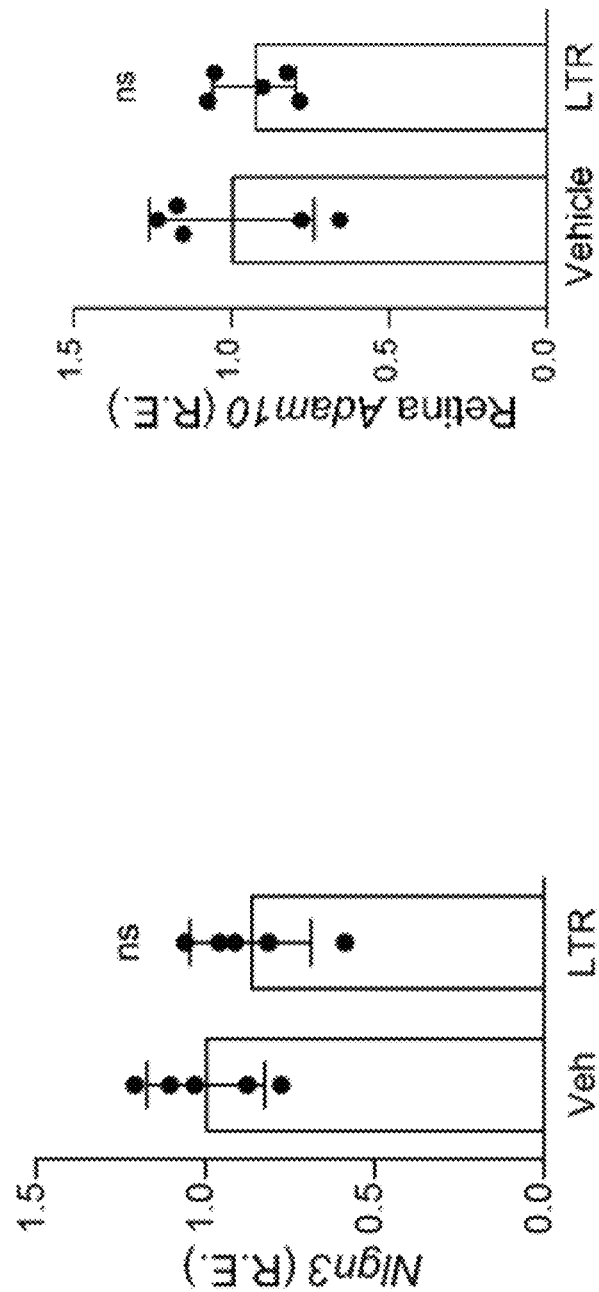
FIG. 16A-FIG. 16D shows an exemplary embodiment of analysis of Arg1809Cys Nf1-mutant neuron signaling in accordance with the present disclosure.
Figure 16B:
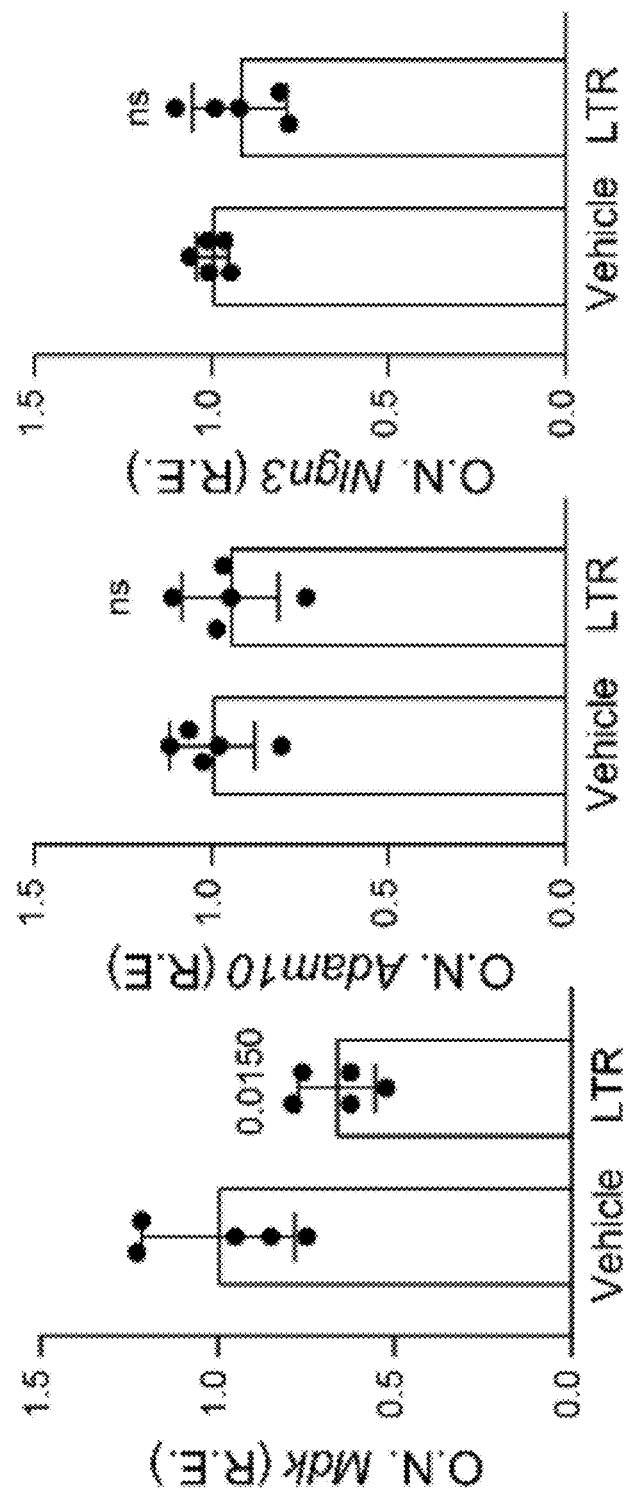
Figure 16C:
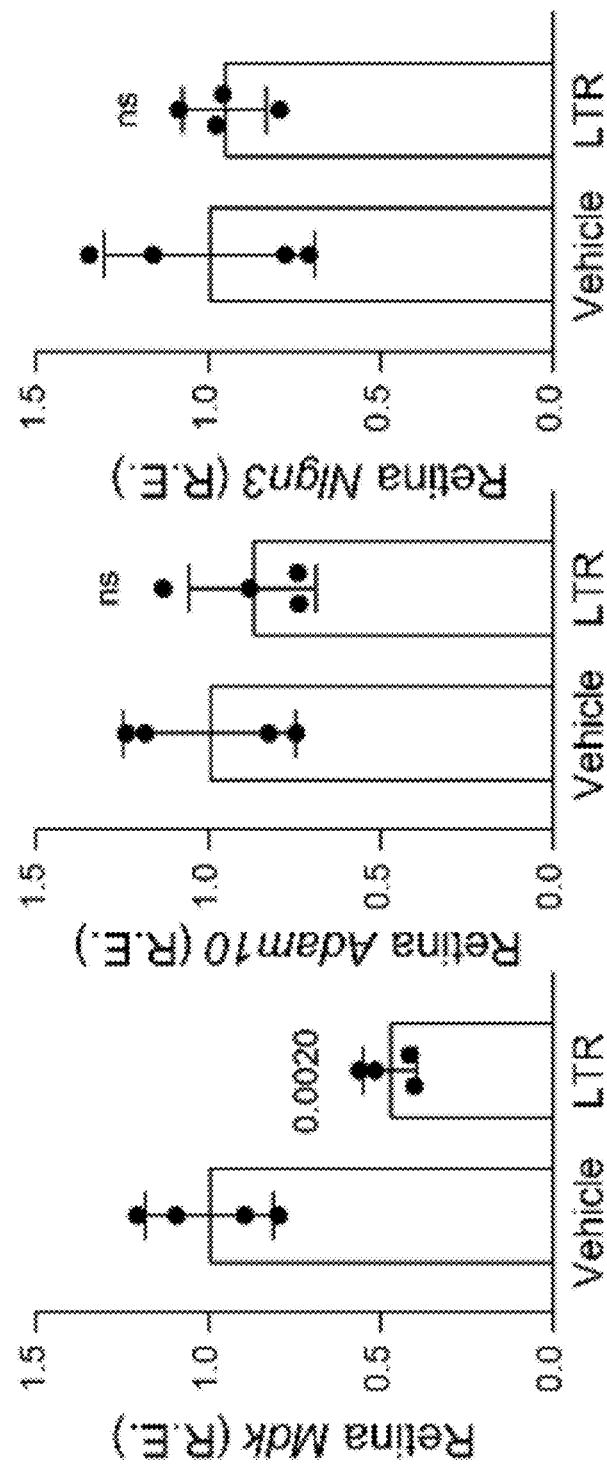
Figure 16D:
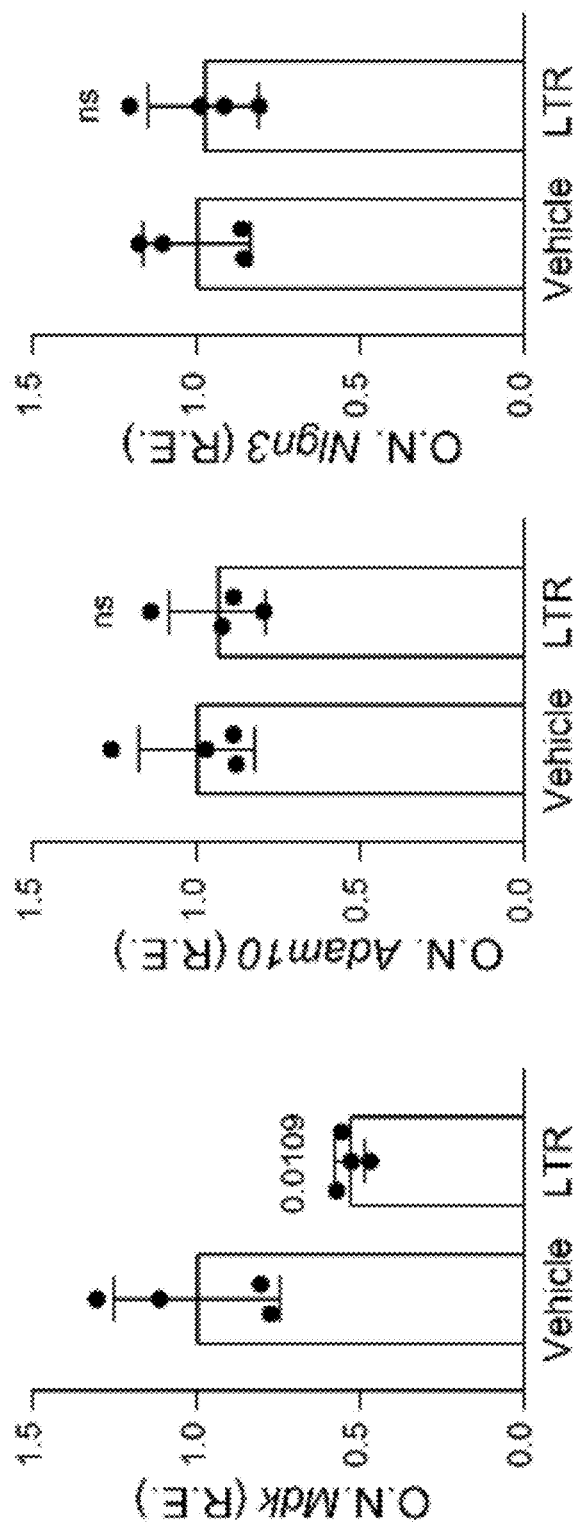
Figure 17C:
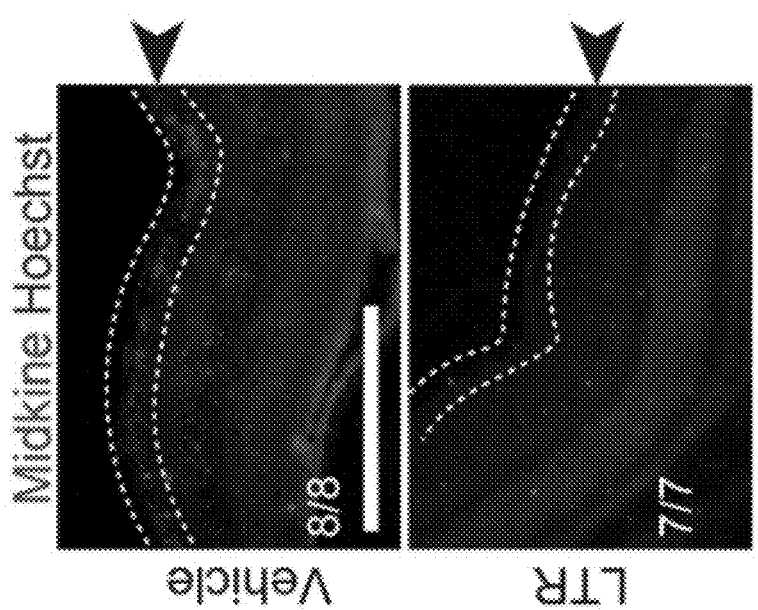
FIG. 17A-FIG. 17E shows an exemplary embodiment of OPG-associated Nf1-mutant neuronal hyperexcitability is HCN channel-dependent in accordance with the present disclosure.
Figure 17B:
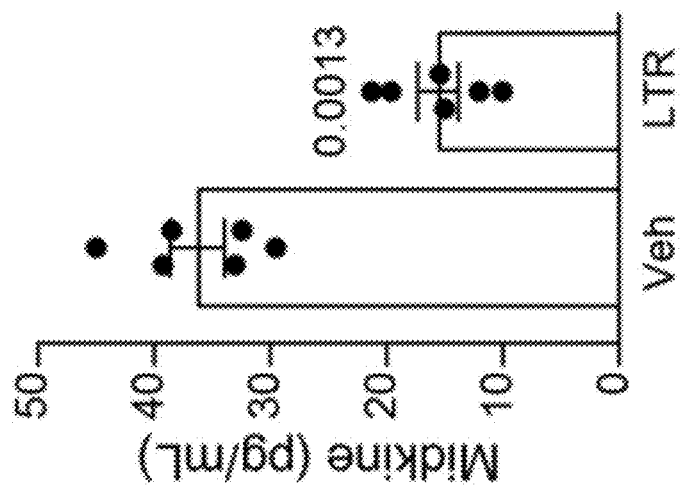
Figure 17A:
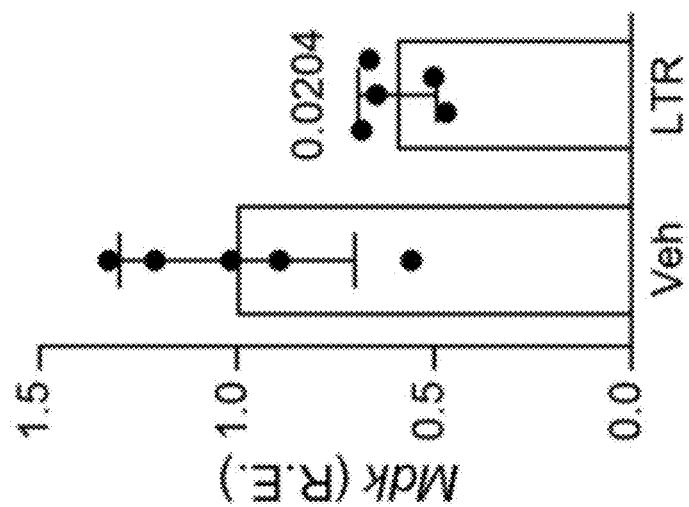
Figures 17D, 17E:
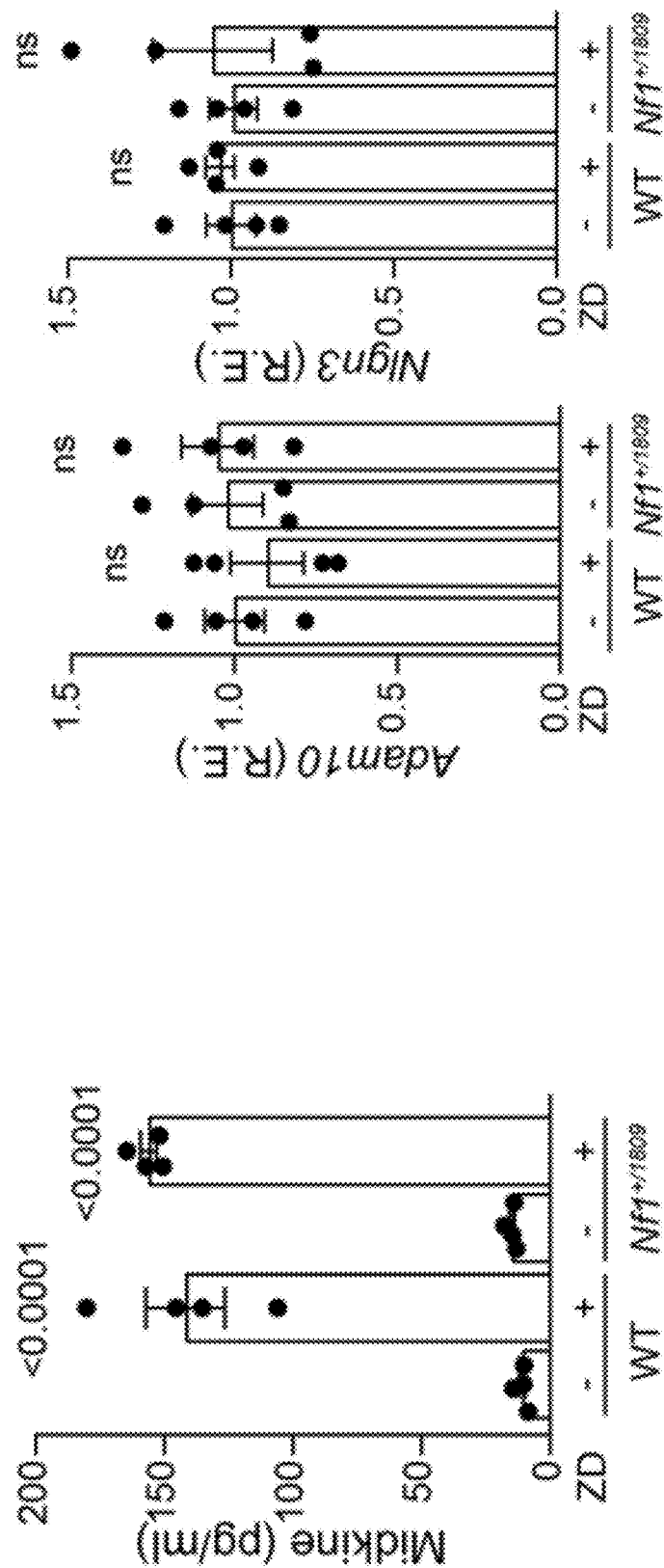
Figure 18C:
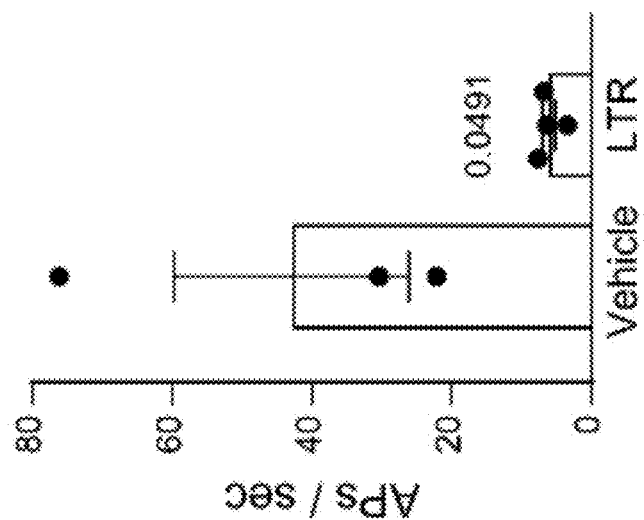
FIG. 18A-FIG. 18E shows an exemplary embodiment of Nf1-mutant hippocampal neuron midkine secretion is dependent on neuronal hyperexcitability in accordance with the present disclosure.
Figure 18B:
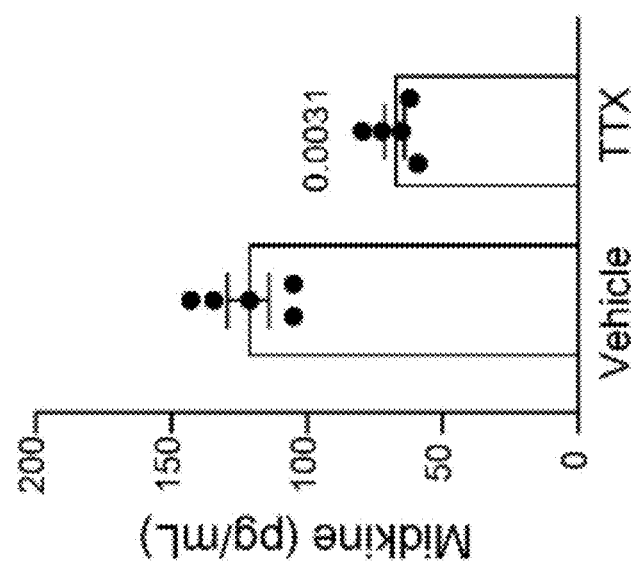
Figure 18A:
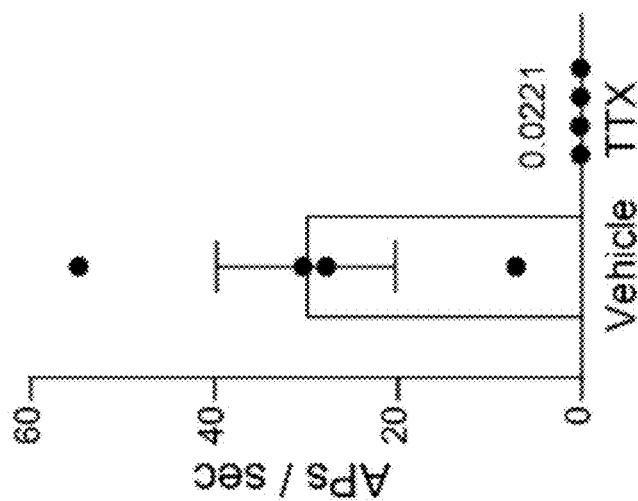
Figures 18D, 18E:
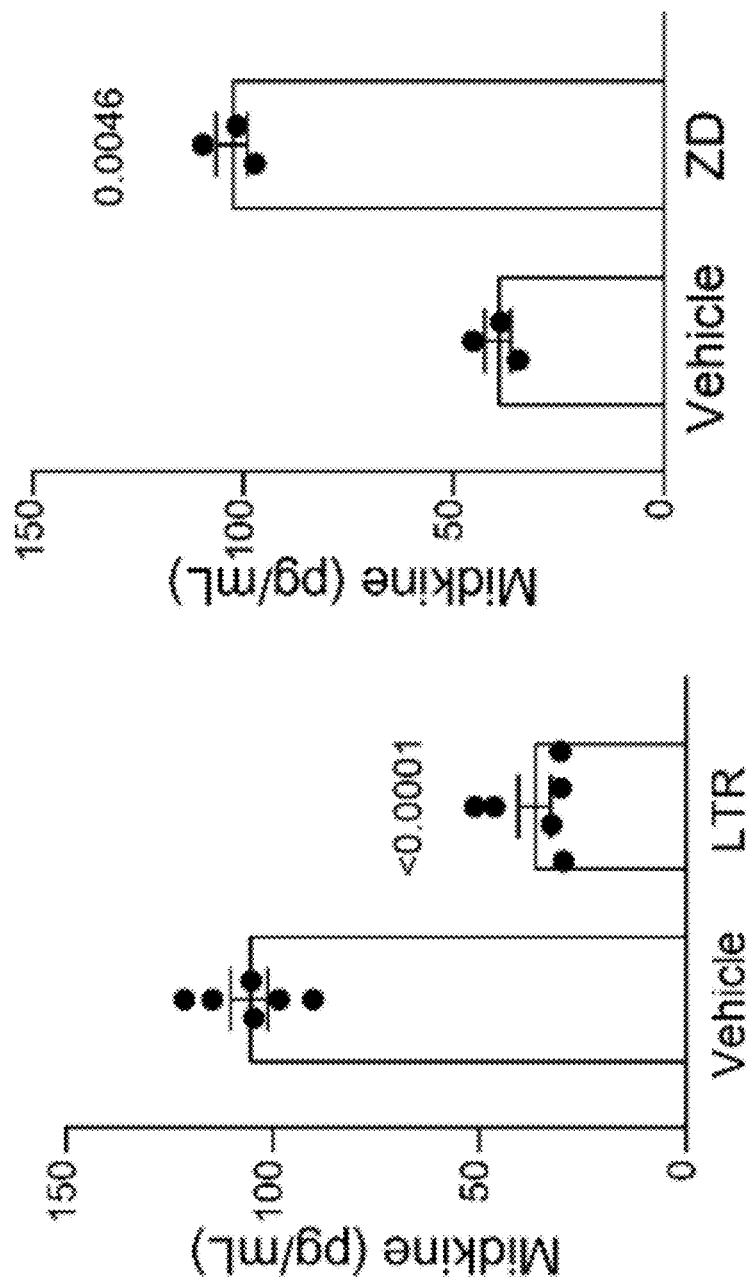
Figure 19A:
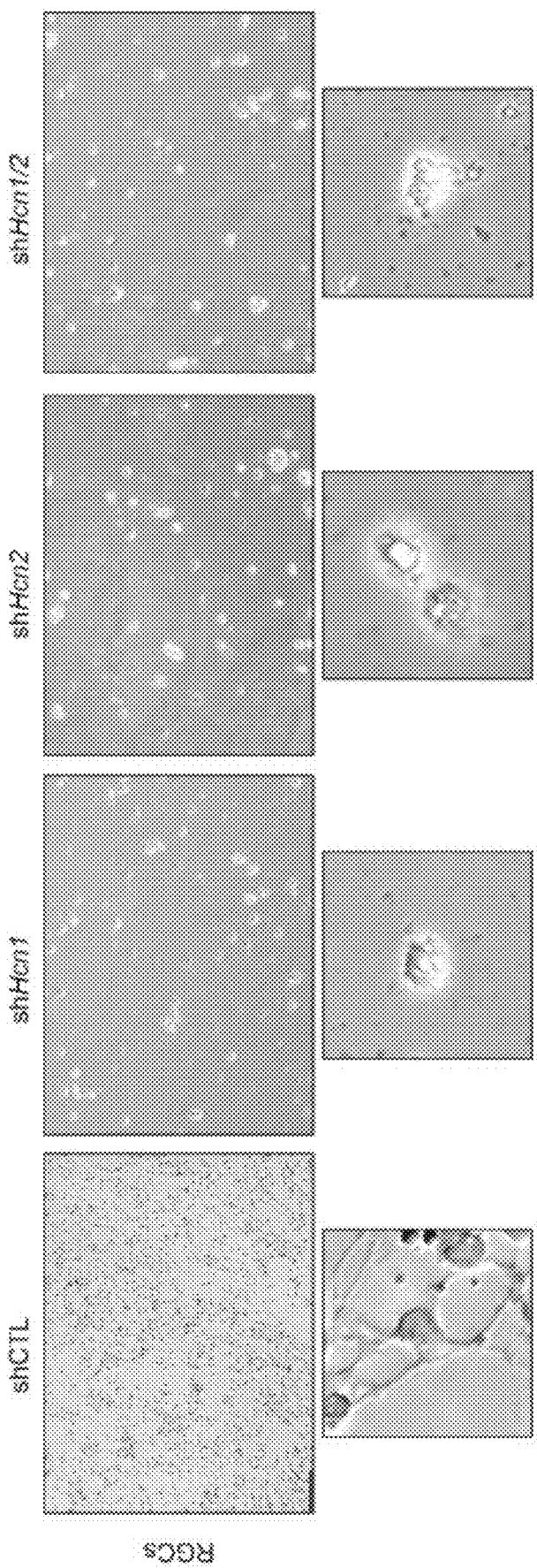
FIG. 19A-FIG. 19C shows an exemplary embodiment of genetic silencing of Hcn1 and Hcn2 results in neuronal death in accordance with the present disclosure.
Figure 19B:
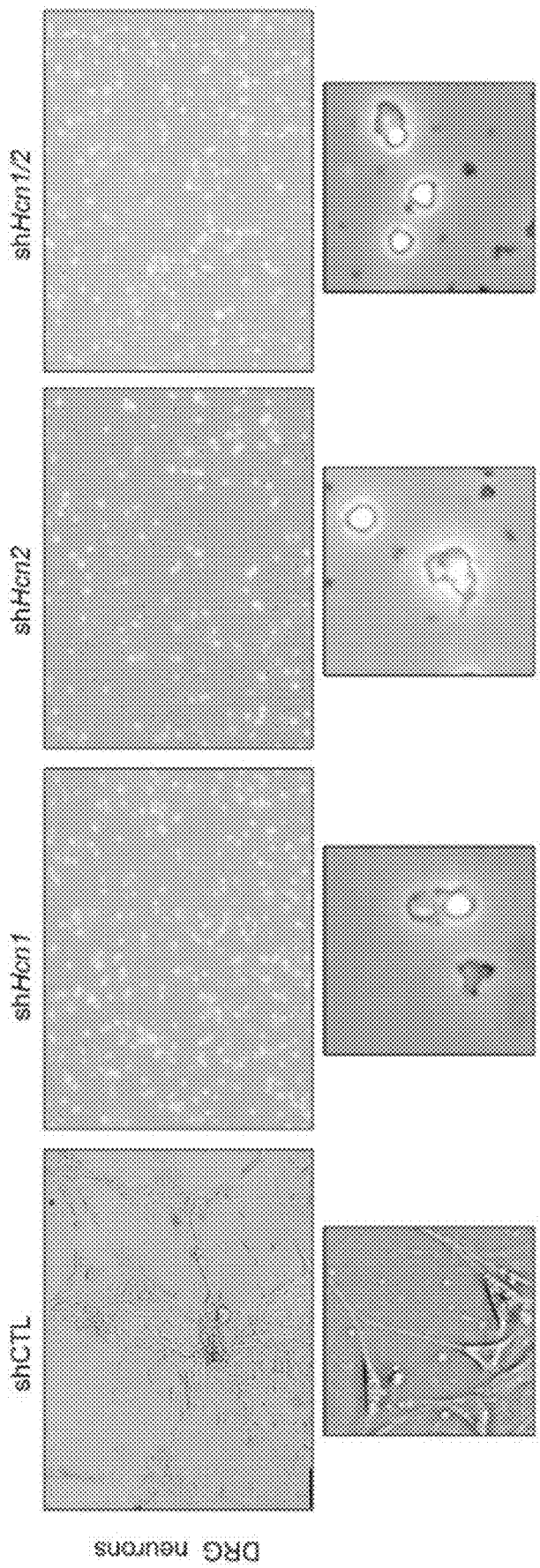
Figure 19C:
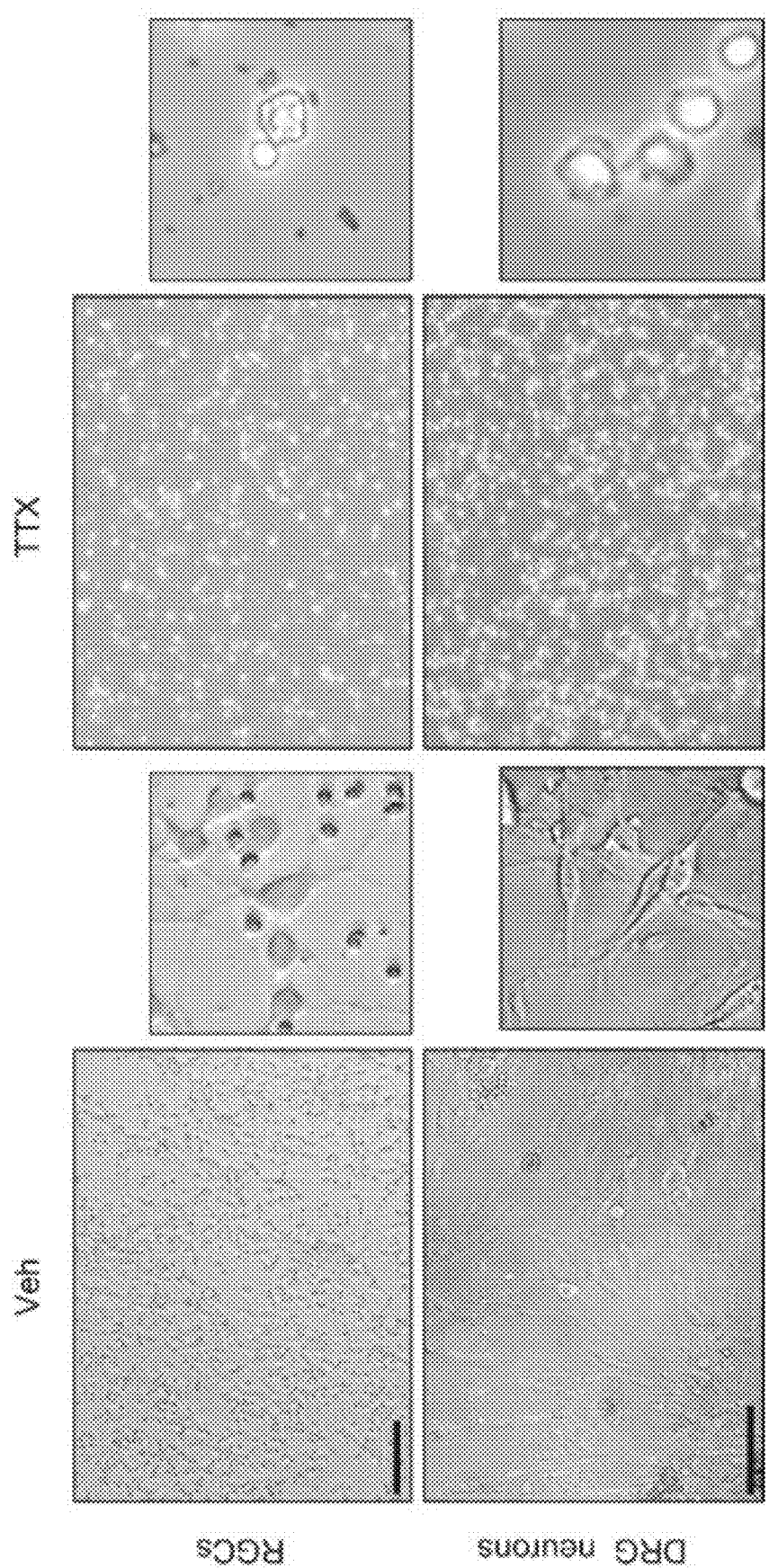

To determine whether light-induced retinal ganglion cell neuronal activity regulates midkine secretion in the optic nerve, Nfl$^{+/neo}$ mice were reared either in 12 h light/dark cycles or completely in the dark for 4 weeks starting at 4 weeks of age. The retinae of dark-reared animals had decreased levels of Nlgn3 (48% decrease; see e.g., FIG. 13A) relative to light/dark-reared controls. In stark contrast, retinal Mdk RNA and protein expression were not affected by the decrease in visual experience (see e.g., FIG. 13B-FIG. 13C), suggesting an alternative mechanism for neuronal activity-dependent midkine production. Based on prior experiments demonstrating that HCN channels control neuronal hyperexcitability and that the Nfl mutation regulates HCN channel function, the effect of Nfl mutation on HCN channel function and neuronal excitability was examined. Hcn1 and Hcn2 account for the majority of retinal Hon channel expression; however, Nfl mutation (Nfl$^{+/neo}$) does not alter Hon levels (see e.g., FIG. 14). To ascertain whether HCN channel function was responsible for the increased neuronal activity and Nlgn3/midkine production, Nfl$^{+/neo}$ RGC neurons were treated with 200 µM lamotrigine (LTR), an HCN channel agonist, and neuron activity was assayed for 3 min (see e.g., FIG. 15A-FIG. 15B). Lamotrigine reduced the firing rates in Nfl$^{+/neo}$ RGC neurons (>80% decrease; see e.g., FIG. 15A-FIG. 15B). In striking contrast, while lamotrigine treatment of either heterozygous Nfl$^{+/neo}$ or OPG-bearing Nfl$^{f/neo}$; hGFAP-Cre mice in vivo did not change Nlgn3 or Adam10 RNA expression (see e.g., FIG. 15C and FIG. 16A-FIG. 16D), Mdk RNA (see e.g., FIG. 17A) and protein levels were reduced in Nfl$^{+/neo}$ retinae (1.9-2.3-fold decrease; see e.g., FIG. 17B-FIG. 17C and FIG. 16C), optic nerves (1.7-2-fold decrease; see e.g., FIG. 16B and FIG. 16D) and RGCs (2.2-fold decrease; see e.g., FIG. 17B) relative to vehicle-treated controls. Conversely, treatment of WT and Nfl$^{+/1809}$ neurons with 30 µM of the HCN channel antagonist ZD7288 (ZD) resulted in a 14-15-fold increase in RGC neuron midkine production (see e.g., FIG. 17D) but did not alter Nlgn3 or Adam10 RNA expression (see e.g., FIG. 17E). Identical results were obtained using hippocampal neurons (see e.g., FIG. 7A-FIG. 7C and FIG. 18A-FIG. 18E), supporting the idea that baseline neuronal hyperexcitability mediated by HCN function is a shared feature of Nfl-mutant CNS neurons. As a complementary genetic approach, wild-type neurons were infected using three separate short hairpins against Hcn1 and Hcn2. Both alone and in combination, infection of RGC and DRG neurons with the shHcn1/2 constructs resulted in rapid neuronal death within 6 hours (see e.g., FIG. 19A-FIG. 19B), demonstrating that Hcn1 and Hcn2 presence is required for neuronal survival. Similarly, incubation of neurons with TTX, a drug that abolishes neuronal activity, also induces neuronal death within 6 hours (see e.g., FIG. 19C). Together, these data reveal the existence of an HCN channel-dependent mechanism for Nfl-mutant CNS tumor-associated neuronal midkine production.

Increased Nfl-Mutant Neuron Activity is not RAS-Dependent.

Figures 20, 21, 22A:
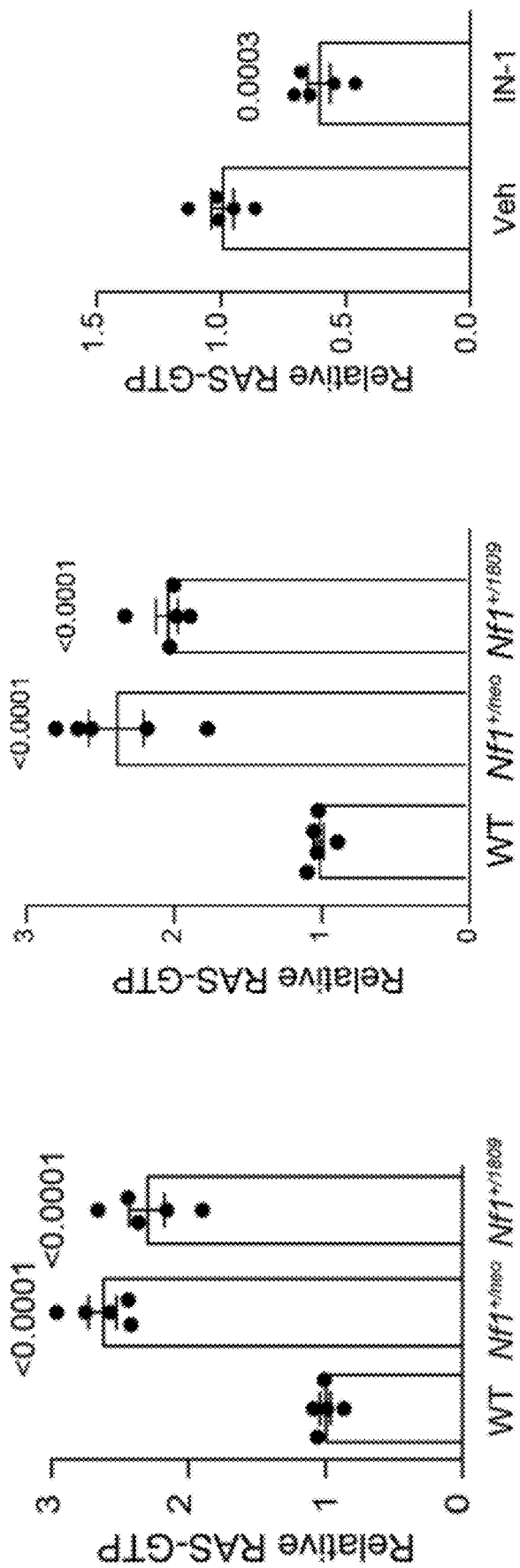
FIG. 20 shows an exemplary embodiment of OPG-associated Nf1-mutant neuronal hyperexcitability is HCN channel-dependent in accordance with the present disclosure.
FIG. 21 shows an exemplary embodiment of Nf1-mutant hippocampal neuron midkine secretion is dependent on neuronal hyperexcitability in accordance with the present disclosure.
FIG. 22A-FIG. 22B shows an exemplary embodiment of OPG-associated Nf1-mutant neuronal hyperexcitability is HCN channel-dependent in accordance with the present disclosure.
Figures 22B, 23, 24A:
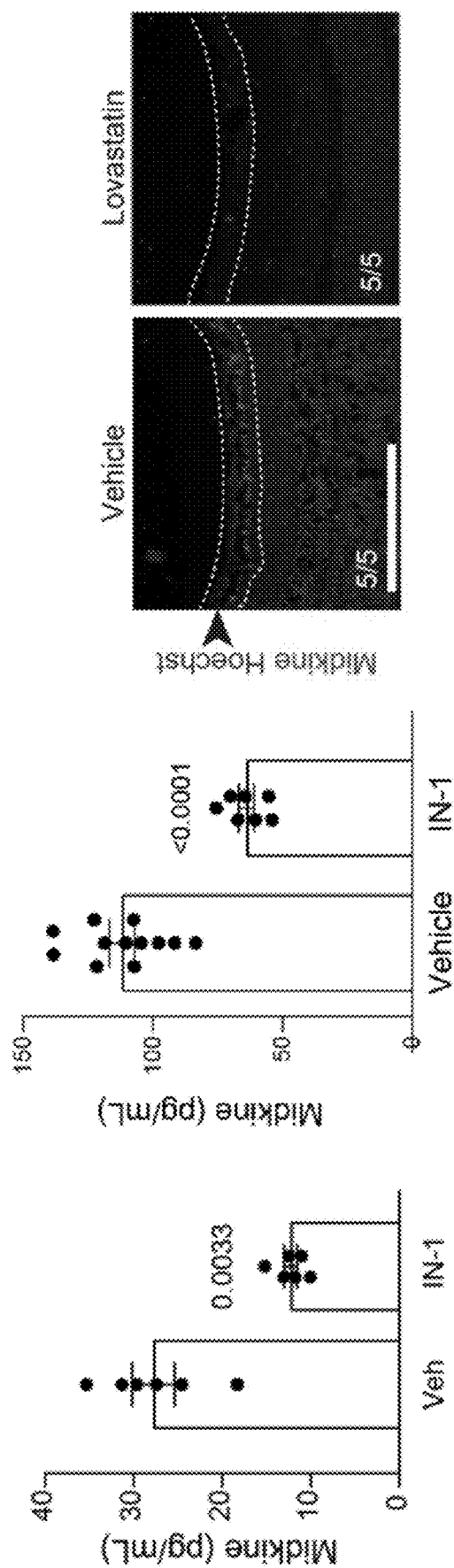
FIG. 23 shows an exemplary embodiment of Nf1-mutant hippocampal neuron midkine secretion is dependent on neuronal hyperexcitability in accordance with the present disclosure.
FIG. 24A-FIG. 24B shows an exemplary embodiment of OPG-associated Nf1-mutant neuronal hyperexcitability is HCN channel-dependent in accordance with the present disclosure.
Figure 24B:
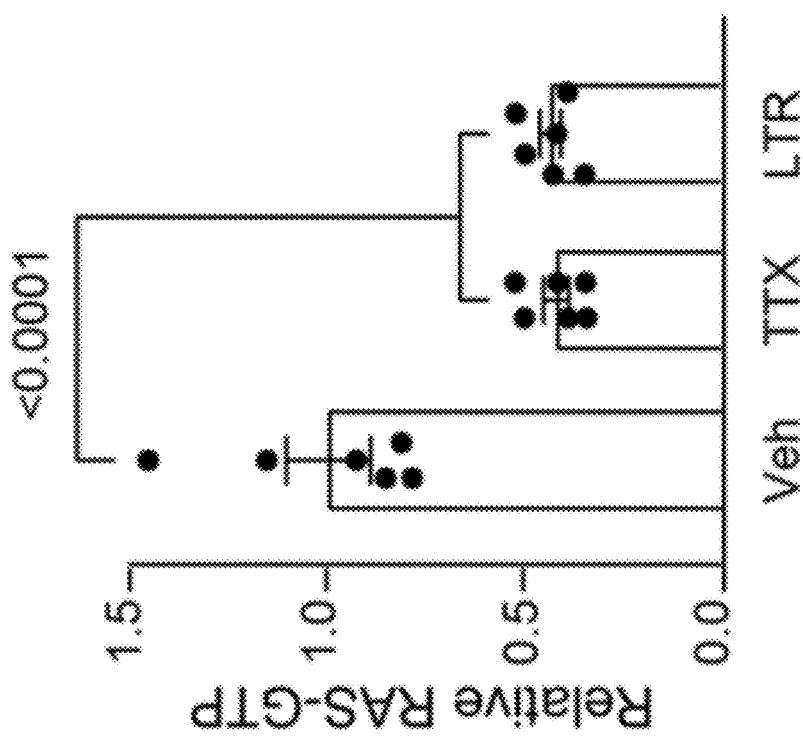
Figure 25:
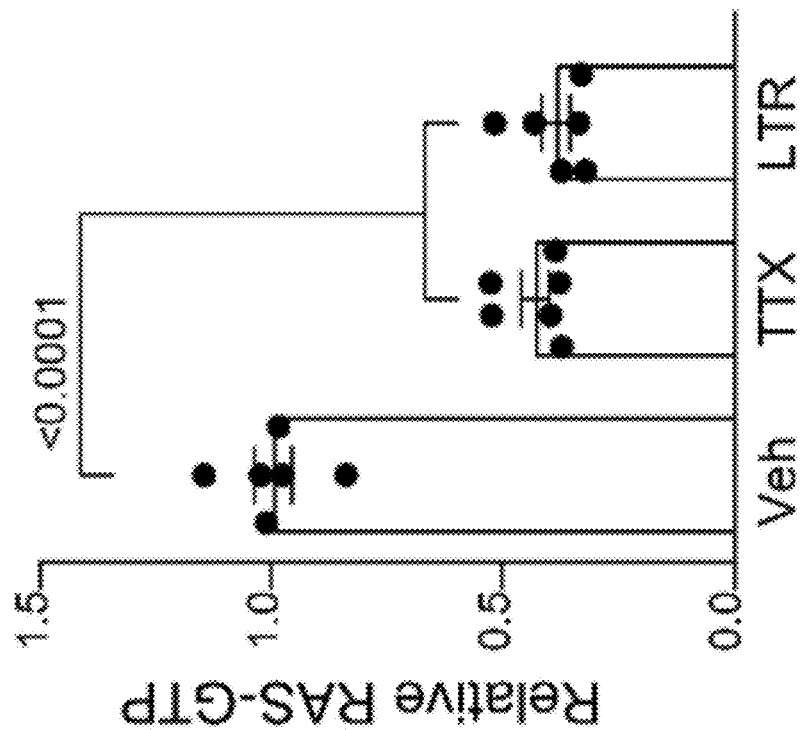
FIG. 25 shows an exemplary embodiment of Nf1-mutant hippocampal neuron midkine secretion is dependent on neuronal hyperexcitability in accordance with the present disclosure.
Figure 26A:
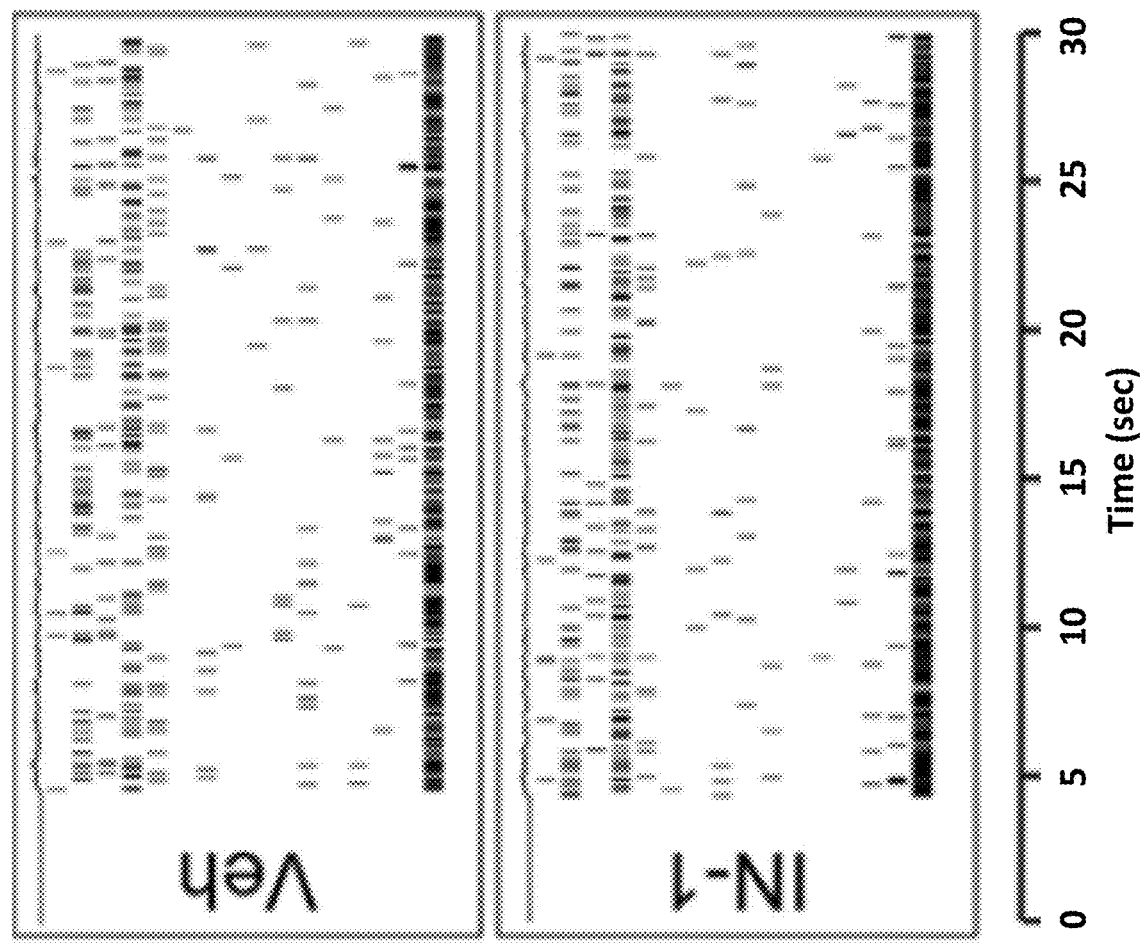
FIG. 26A-FIG. 26B shows an exemplary embodiment of OPG-associated Nf1-mutant neuronal hyperexcitability is HCN channel-dependent in accordance with the present disclosure.
Figure 27:
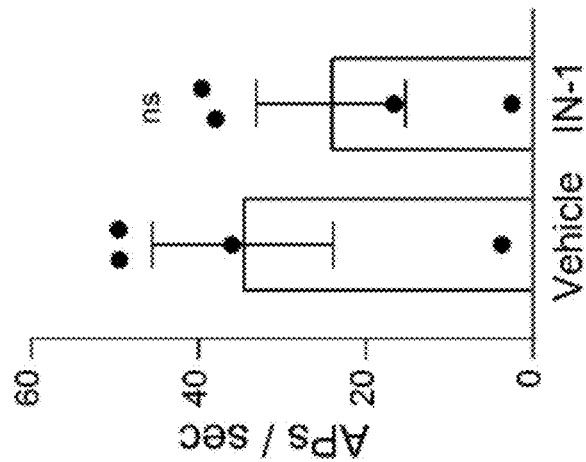
FIG. 27 shows an exemplary embodiment of Nf1-mutant hippocampal neuron midkine secretion is dependent on neuronal hyperexcitability in accordance with the present disclosure.
Figure 26B:
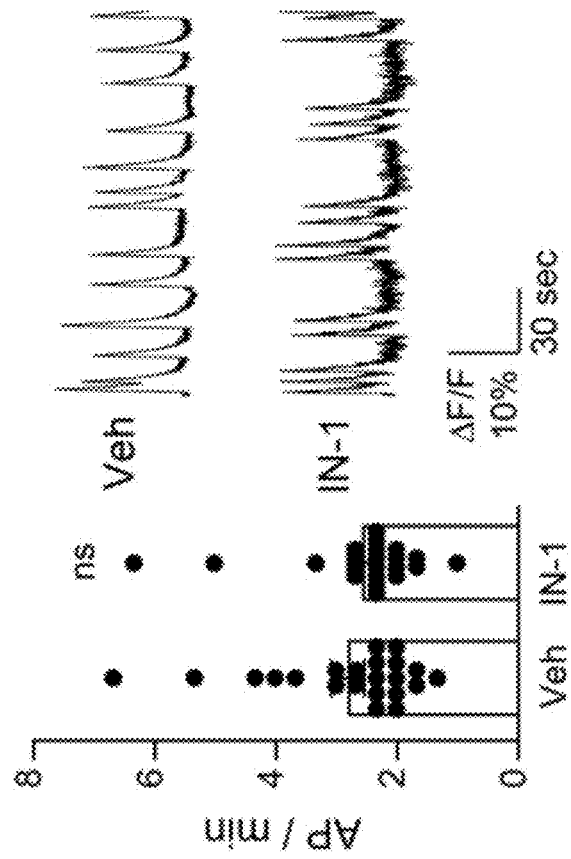

As the NF1 protein (neurofibromin) functions a negative regulator of RAS activity (RAS-GTPase-activating protein), RAS-GTP levels were increased by 2.3-2.7-fold in Nfl$^{+/1809}$ RGC and hippocampal neurons relative to WT controls, similar to Nfl$^{+/neo}$ neurons (see e.g., FIG. 20 and FIG. 21) and other mouse strains harboring NF1 patient-specific Nfl germline mutations. The finding of similarly increased RAS-GTP in Nfl$^{+/1809}$ CNS neurons suggests that RAS deregulation is not responsible for the failure of Nfl$^{f/1809}$; hGFAP-Cre mice to form tumors. However, it does not exclude RAS as a potential signaling effector downstream of HCN channel activity. In this respect, treatment of Nfl$^{+/neo}$ neurons with the pan-RAS inhibitor, IN-1, reduced RAS-GTP levels (see e.g., FIG. 22A and FIG. 21), as well as midkine expression (see e.g., FIG. 22B and FIG. 23). In addition, systemic treatment of Nfl$^{+/neo}$; hGFAP-Cre mice with the RAS inhibitor lovastatin decreased RGC midkine expression in vivo (see e.g., FIG. 24A), indicating that RAS operates to control midkine expression. Conversely, whereas inhibition of Nfl$^{+/neo}$ neuronal activity by TTX and lamotrigine reduced RAS hyperactivation (see e.g., FIG. 24B and FIG. 25), RAS (IN-1) inhibition had no effect on neuronal activity (see e.g., FIG. 26A-FIG. 26B and FIG. 27). Taken together, these results position RAS-mediated neuron midkine production downstream of HCN channel activity, and demonstrate that increased baseline excitability of tumor-associated Nfl-mutant neurons is RAS-independent.

Increased HCN Channel Activity Prevents OPG Progression In Vivo.

Figure 28A:
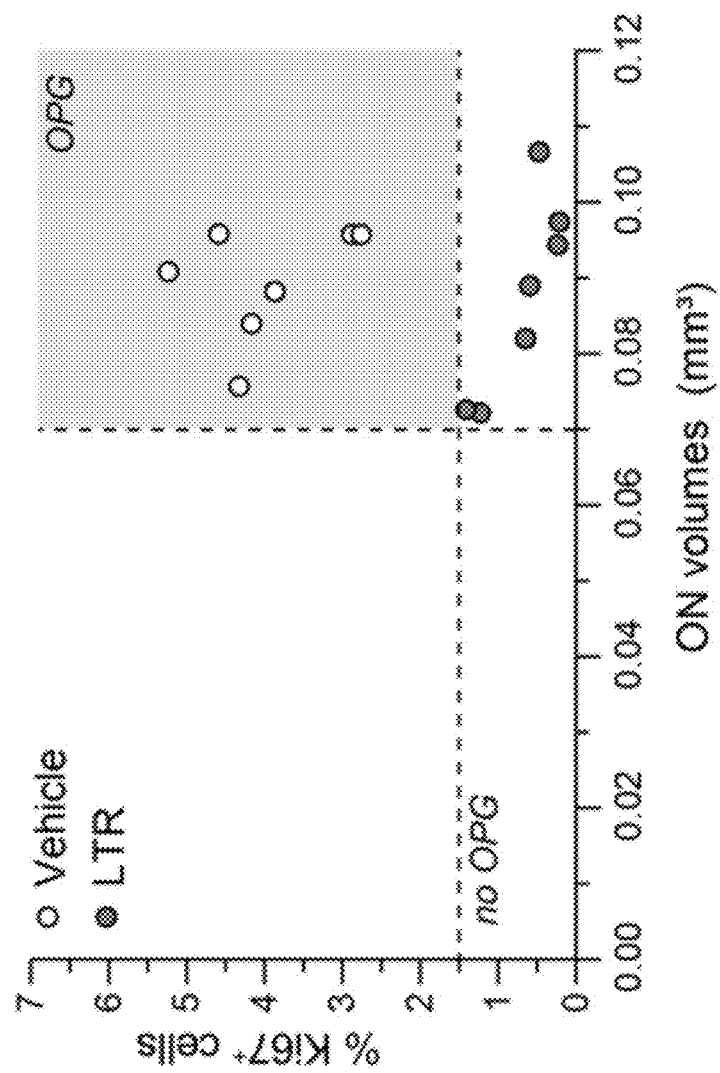
FIG. 28A-FIG. 28B shows an exemplary embodiment of OPG-associated Nf1-mutant neuronal hyperexcitability is HCN channel-dependent in accordance with the present disclosure.
Figure 28B:
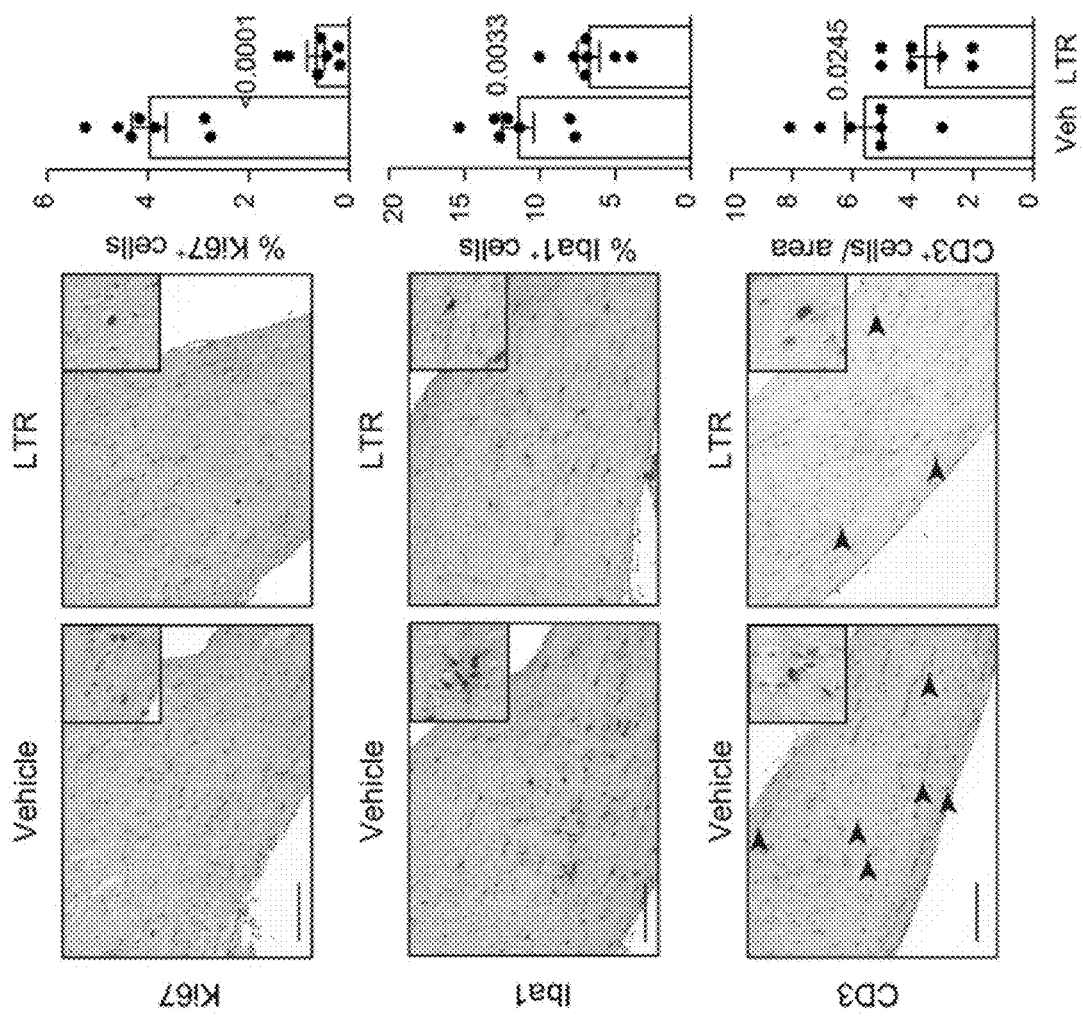

To determine whether HCN channel function is critical for OPG formation, Nfl$^{f/neo}$; hGFAP-Cre (Nfl-OPG) mice received intraperitoneal injections of lamotrigine from 6 to 8 weeks of age, at the time of early tumor evolution. Consistent with neuronal activity mediating Nfl-OPG progression, HCN activation by lamotrigine reduced OPG development at 3 months of age. Lamotrigine treatment did not decrease optic nerve volumes (1.5-fold increased volumes relative to WT controls; see e.g., FIG. 28A), unlike dark-reared Nfl-OPG mice or those genetically lacking Ngln3, where tumor initiation was completely prohibited. However, lamotrigine treatment resulted in reduced optic nerve proliferation (% Ki67$^+$ cells; 5.7-fold decrease), as well as microglia (% Iba1$^+$ cells; 1.7-fold decrease) and T-cell (CD3$^+$ cells; 1.6-fold decrease) content, relative to vehicle-treated Nfl-OPG mice, comparable to WT mouse optic nerves (see e.g., FIG. 28A-FIG. 28B). These results indicate that HCN channel-regulated midkine production is necessary for tumor progression, rather than initiation, but establish HCN channel activity as a targetable regulator of neuronal activity-dependent tumor progression.

Arg1809Cys Nfl-Conditional Mutant Mice do not Develop Plexiform Neurofibromas.

Figures 29A, 29B:
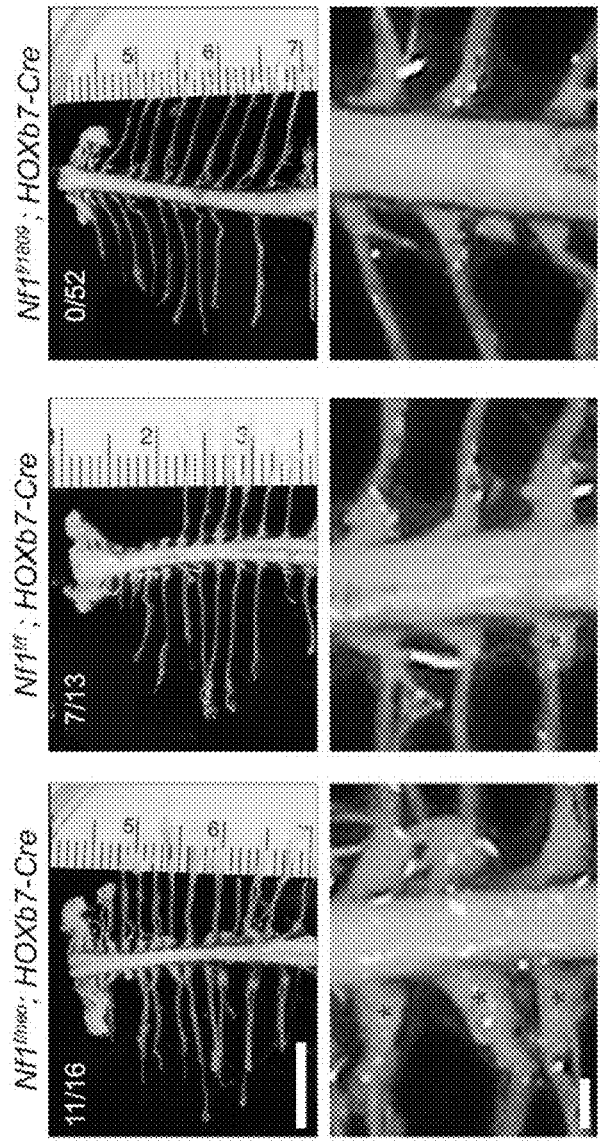
FIG. 29A-FIG. 29G shows an exemplary embodiment of Arg1809Cys Nf1-mutant mice do not develop neurofibromas following somatic Nf1 inactivation in accordance with the present disclosure.
Figure 29C:
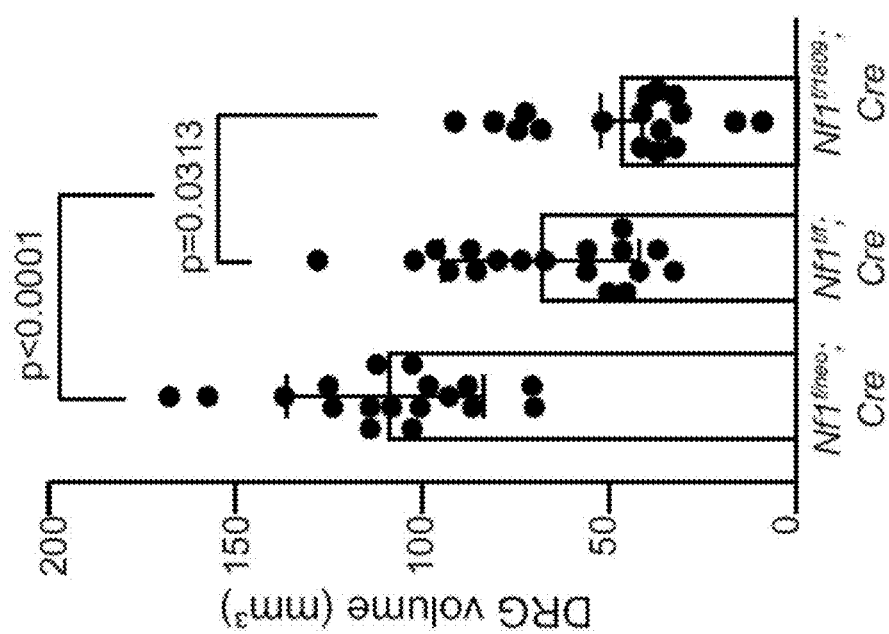
Figure 29D:
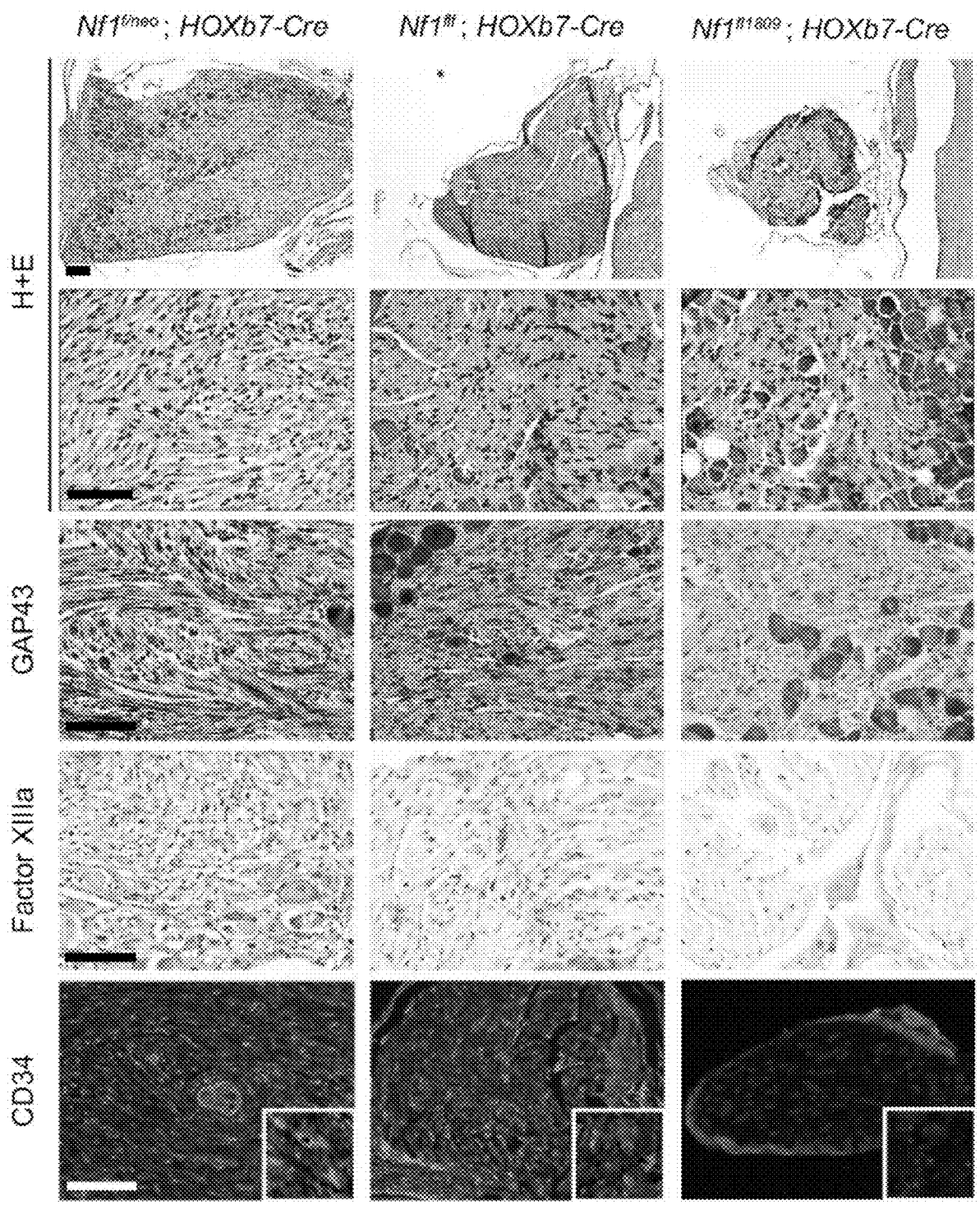
Figure 29E:
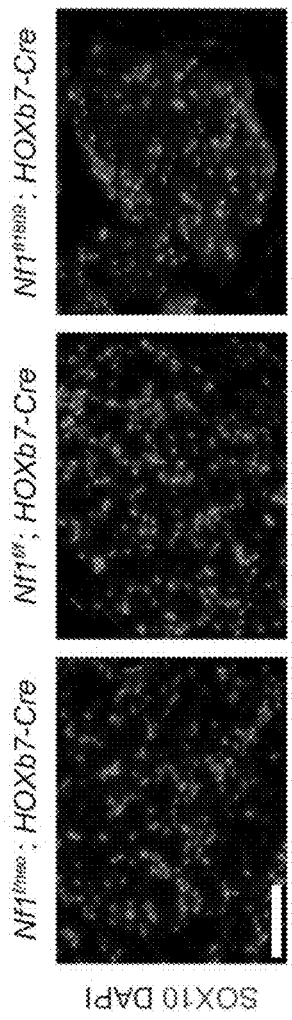
Figure 29F:
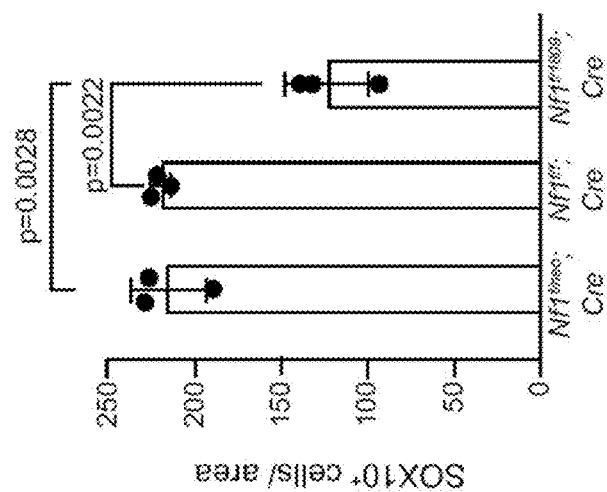
Figure 29G:
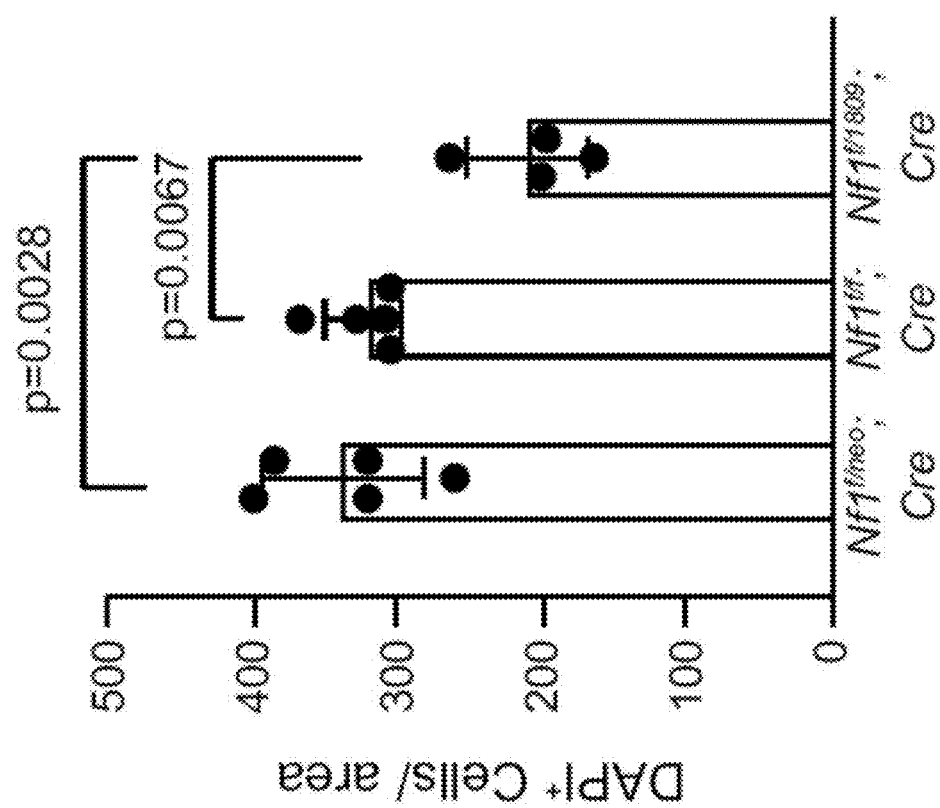

Since patients with the R1809C germline NF1 gene mutation also do not develop plexiform neurofibromas (pNFs) (see e.g., FIG. 29A), Nfl$^{+/1809}$ mice were engineered with somatic loss of the conditional Nfl allele (Nfl$^{flox}$) in Schwann cell progenitors, the cells of origin of pNFs. The resulting Nfl$^{f/1809}$; Hoxb7-Cre mice were analyzed and compared to conventional Nfl-mutant (Nfl$^{f/neo}$; Hoxb7-Cre) mice that develop pNFs. Unlike Nfl$^{f/neo}$; Hoxb7-Cre mice (11/16), and Nfl$^{f/f}$; Hoxb7-Cre mice (7/13), Nfl$^{f/1809}$;

Hoxb7-Cre mice did not develop pNFs at 6 months of age (0/52; see e.g., FIG. 29B). Moreover, Nfl$^{fl1809}$; Hoxb7-Cre mice exhibited neither enlarged DRGs (see e.g., FIG. 29C) nor histological features of pNFs (see e.g., FIG. 29D-FIG. 29E), and their DRGs contained fewer total cells, as well as fewer SOX10$^+$ Schwann cell precursors, the cell of origin for these pNF tumors (see e.g., FIG. 29F-FIG. 29G), demonstrating that mice harboring the Nf1 R1809C mutation fail to develop pNFs.

Tumor-Associated NF1-Mutant, but not NF1$^{+/R1089C}$, Sensory Neurons Produce COL1A2 in an Activity-Dependent Manner.

Figure 30A:
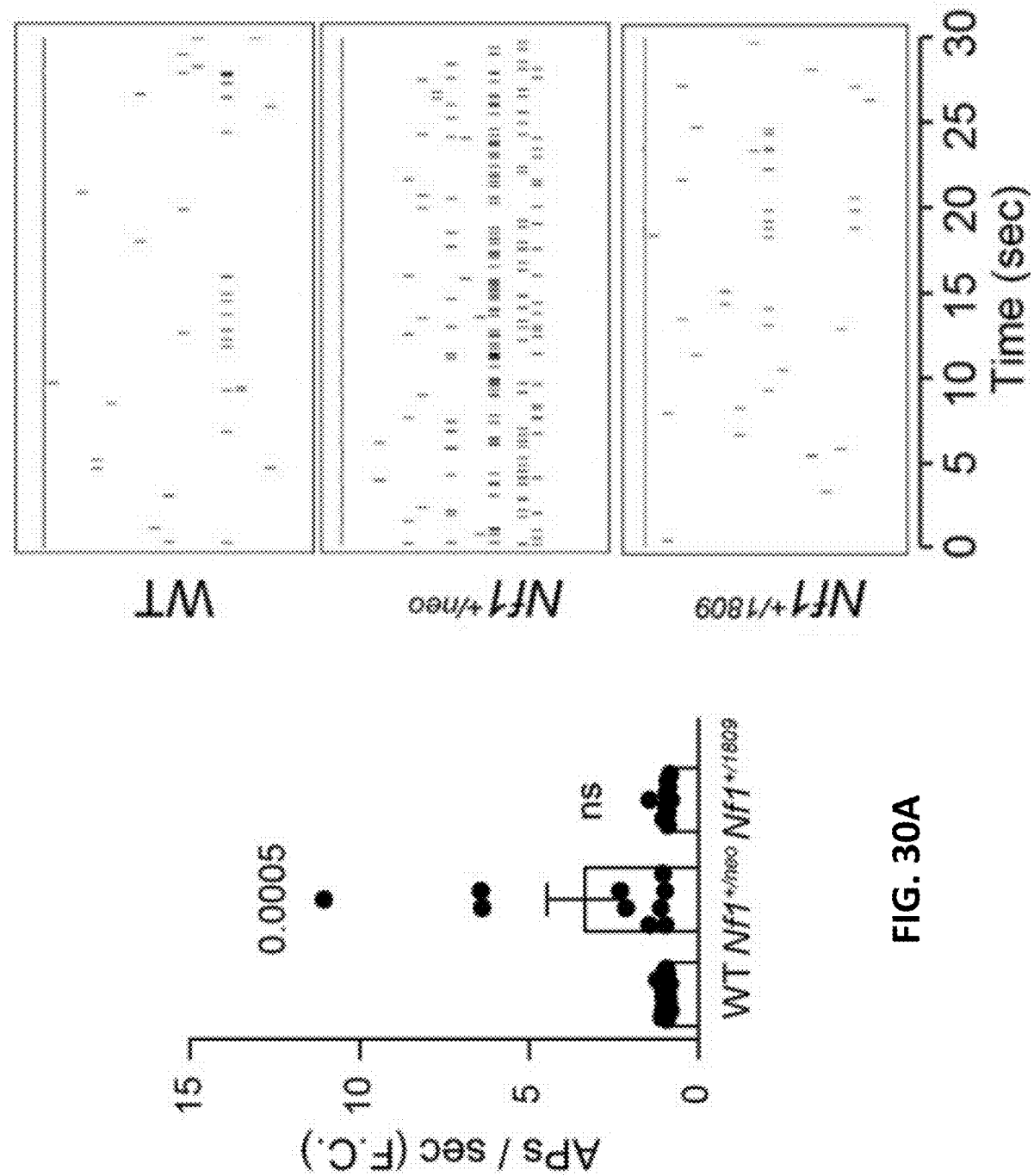
FIG. 30A-FIG. 30B is an exemplary embodiment showing pNF-associated NF1-mutant PNS neurons exhibit increased activity and COL1A2-dependent preneoplastic NF1$^{-/-}$ Schwann cell growth.
Figure 30B:
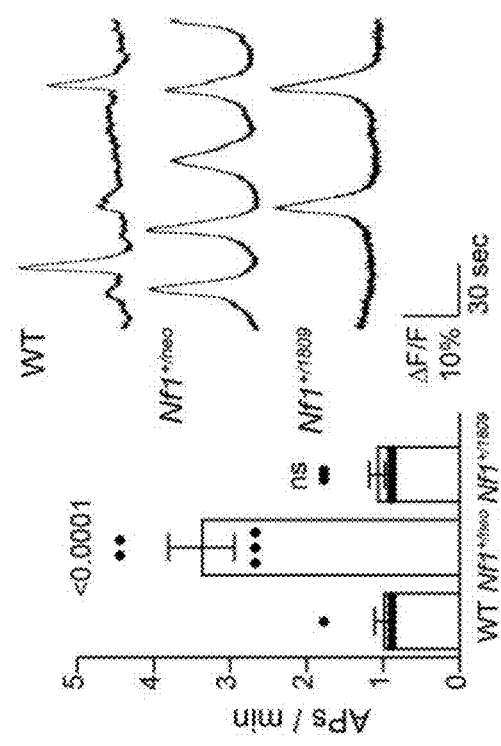
Figure 31:
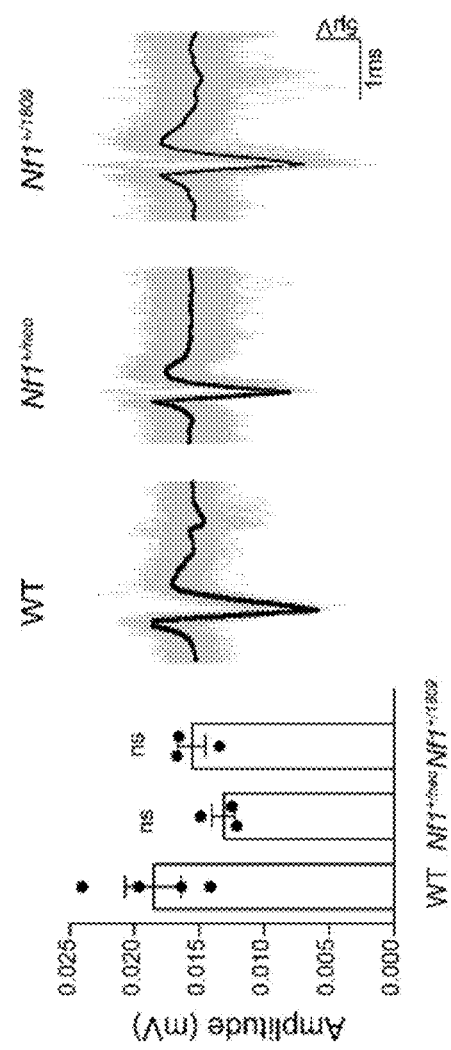
FIG. 31 shows an exemplary embodiment of COL1A2 is uniquely expressed by NF1-mutant peripheral nervous system neurons in accordance with the present disclosure.
Figure 32A:
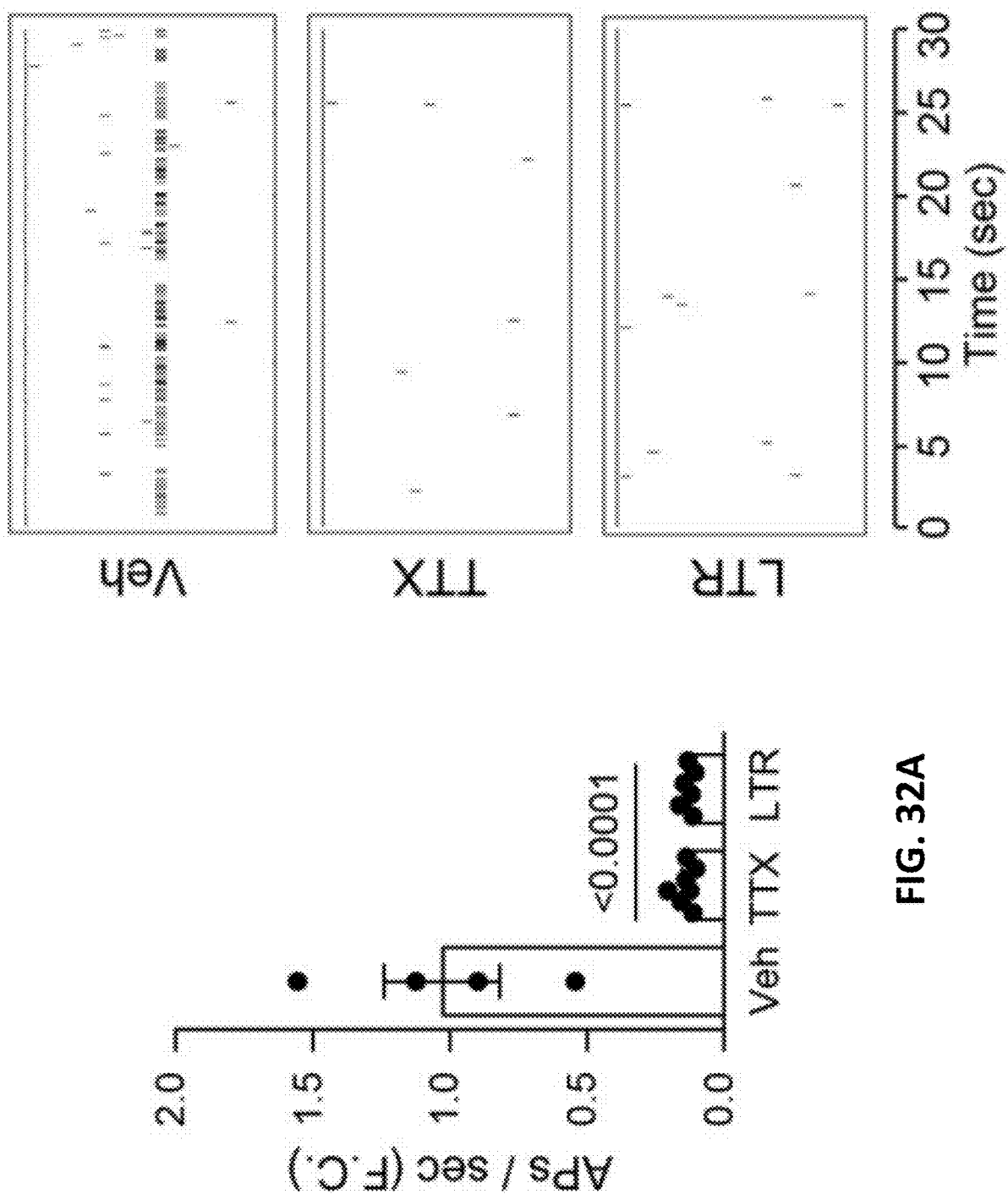
FIG. 32A-FIG. 32C is an exemplary embodiment showing pNF-associated NF1-mutant PNS neurons exhibit increased activity and COL1A2-dependent preneoplastic NF1$^{-/-}$ Schwann cell growth.
Figure 32B:
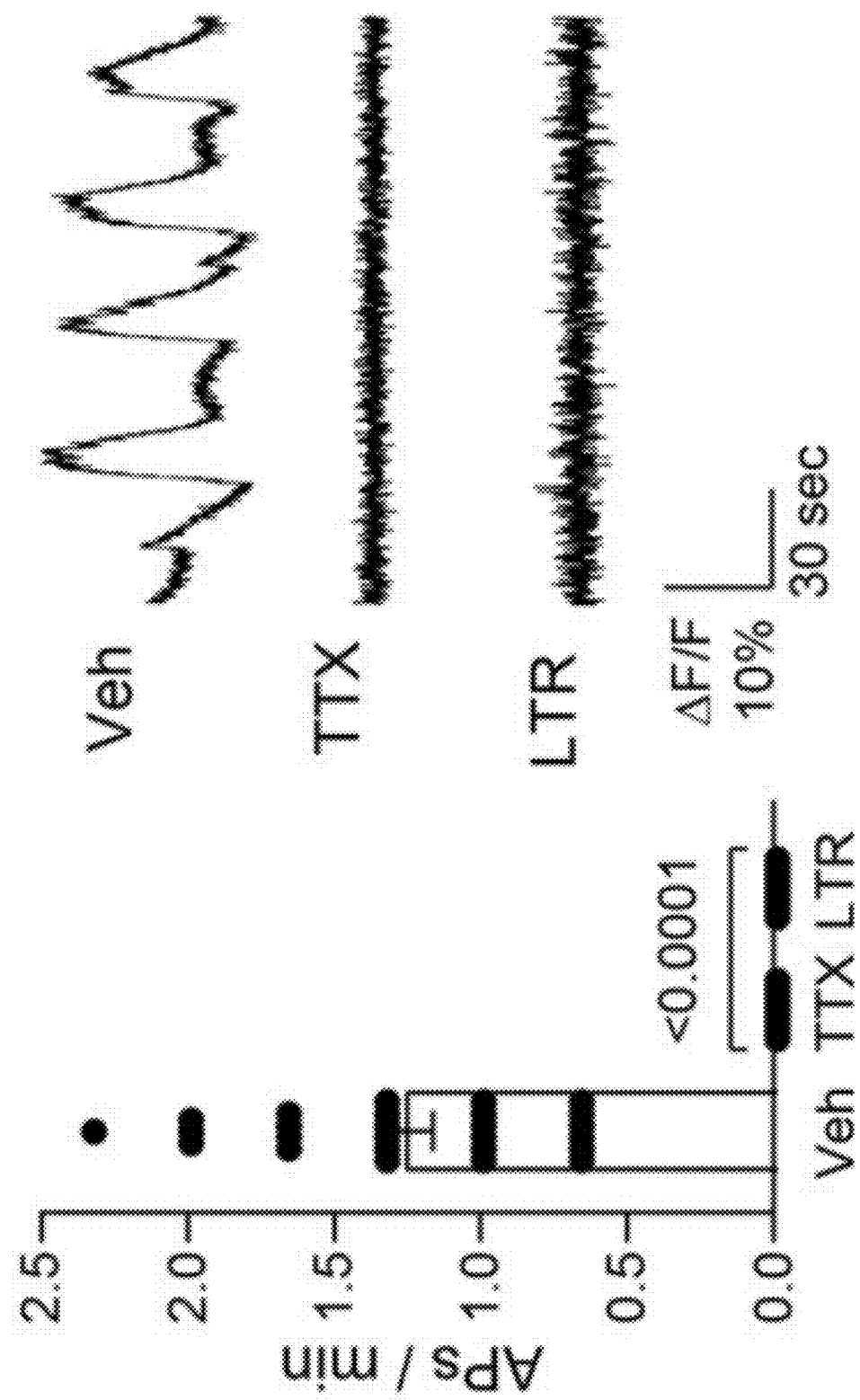

Next, it was investigated whether Nf1-mutant peripheral sensory neurons similarly exhibit increased activity. As such, action potential firing rates of WT, Nf1$^{+/neo}$, and Nf1$^{+/1809}$ DRG neurons were analyzed using multi-electrode array and calcium-imaging recordings (see e.g., FIG. 30A-FIG. 30B). As observed in Nf1$^{+/neo}$ CNS neurons, Nf1$^{+/neo}$, but not Nf1$^{+/1809}$, DRG neurons exhibited 3.4-fold increased action potential firing rates relative to WT controls (see e.g., FIG. 30A-FIG. 30B and FIG. 31). Moreover, both TTX and lamotrigine reduced neuronal hyperexcitability (>85% reduction in action potential firing rate; see e.g., FIG. 32A-FIG. 32B) relative to vehicle-treated controls. These results establish that Nf1 mutation confers HCN channel activity-regulated sensory neuron hyperexcitability.

Figure 32C:
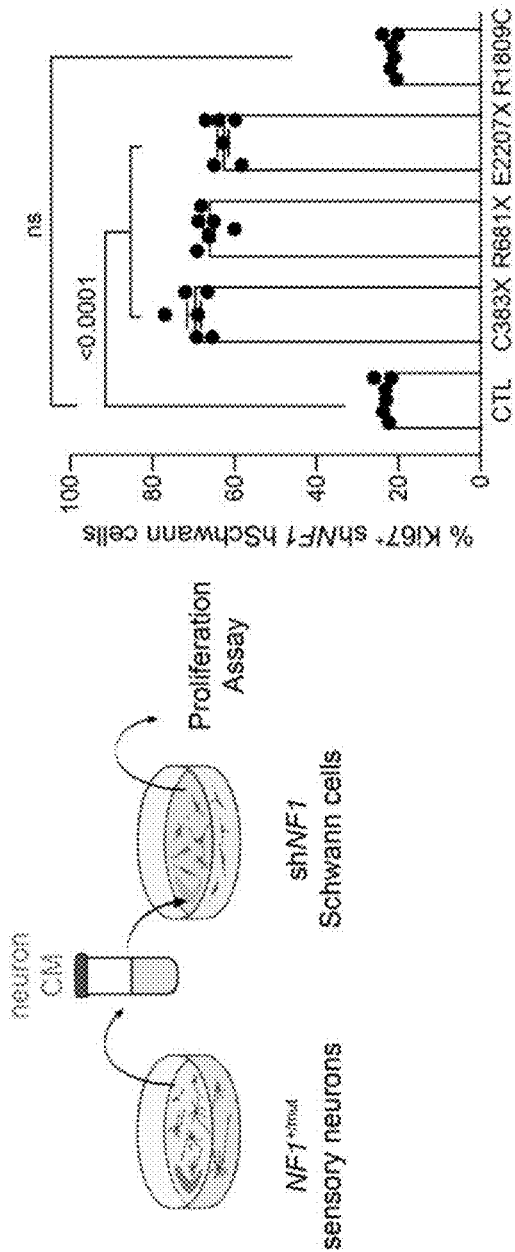
Figure 33A:
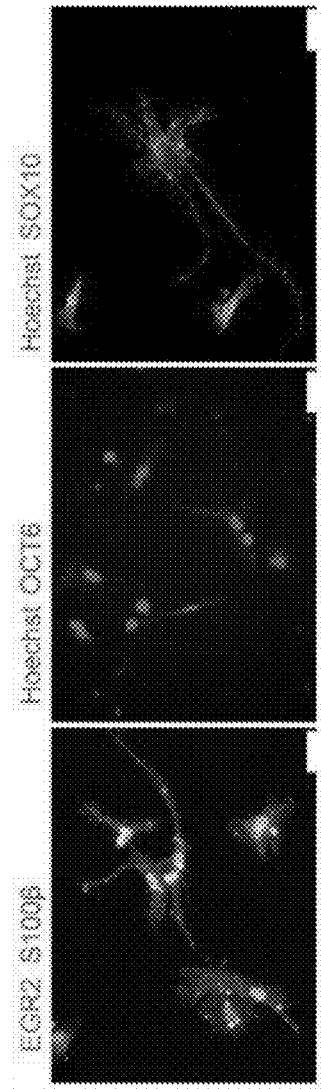
FIG. 33A-FIG. 33D shows an exemplary embodiment of human shNF1 Schwann cell and sensory neuron analysis in accordance with the present disclosure.
Figure 33B:
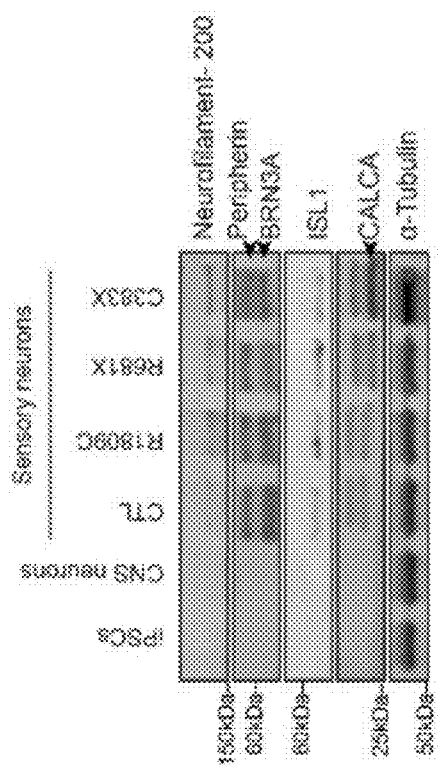
Figure 33C:
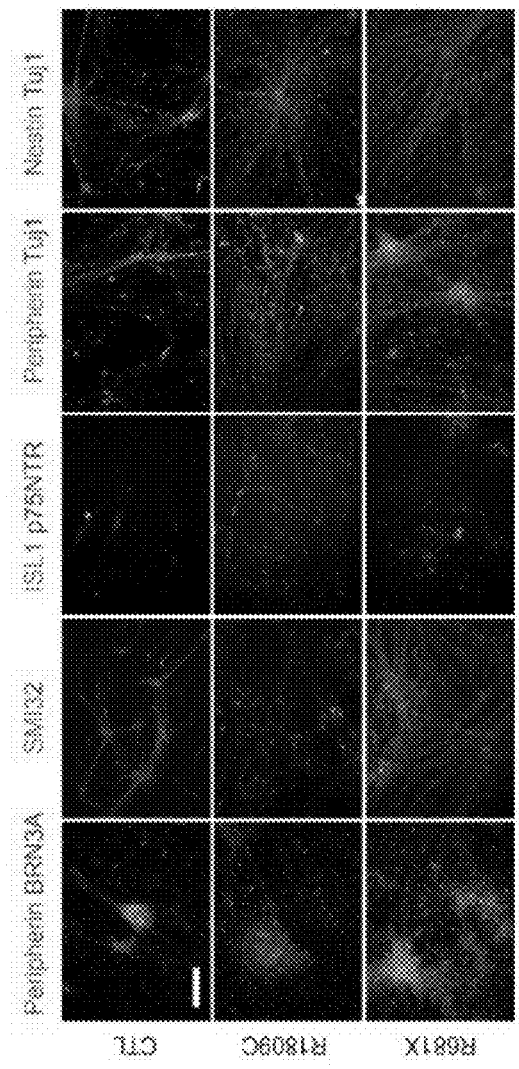
Figure 33D:
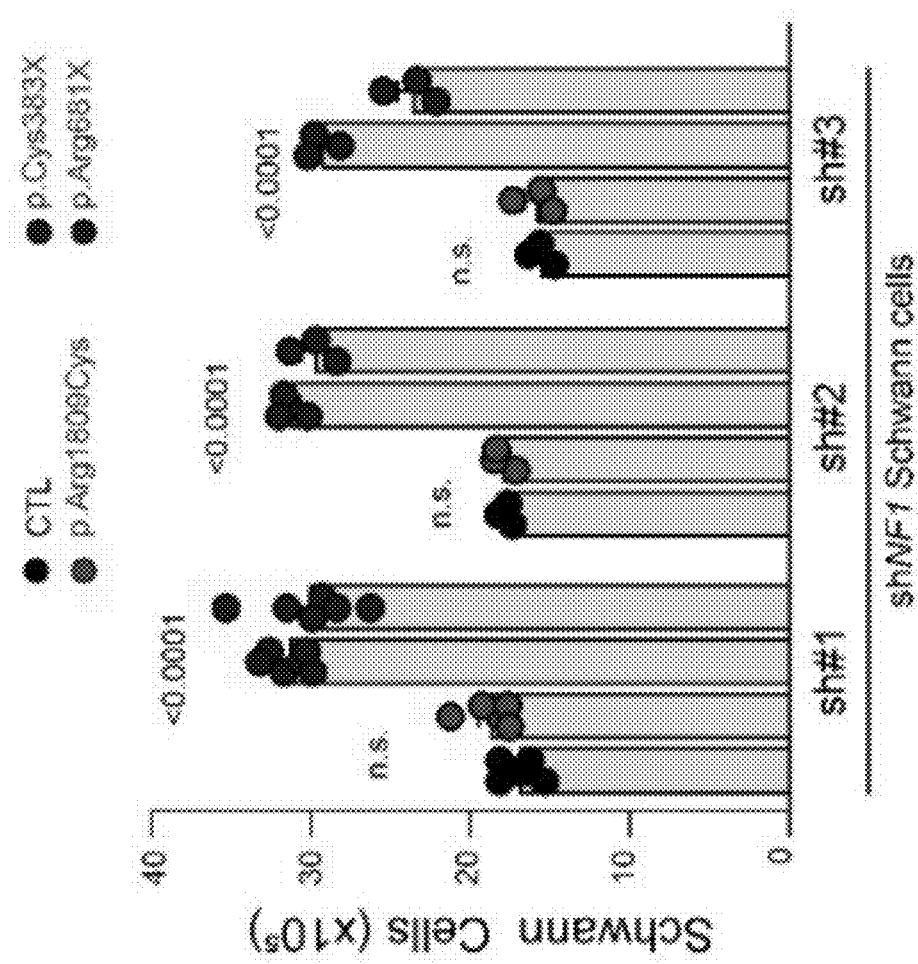

Based on these findings in the CNS, it was hypothesized that PNS tumor (plexiform neurofibroma) growth is also dependent upon neuron activity-dependent paracrine factor secretion. Since neuronal trophic factors that mediate plexiform neurofibroma preneoplastic cell (NF1$^{-/-}$ Schwann cells; shNF1 SCs, see e.g., FIG. 1A) growth have not yet been identified, hiPSC-derived sensory neurons were leveraged that harbor heterozygous NF1 mutations found in patients with (c.1149 C>A, p.Cys381X; c.2041 C>T, pArg681X; c.6619 C>T, p.Gln2207X; Group 1) or without (c.5425 C>T; p.Arg1809Cys; Group 2) neurofibromas (see e.g., FIG. 32C and FIG. 33A-FIG. 33C). As Schwann cells are the proliferative neoplastic cells in neurofibromas, the in vitro proliferation was used as a proof-of-principle measure of their potential to proliferate within a neurofibroma in vivo. Conditioned media (CM) from group 1, but from not group 2, NF1-mutant neurons increased preneoplastic shNF1 Schwann cell proliferation (3.4-3.6-fold increase in Ki67$^+$ Schwann cells; see e.g., FIG. 32C and FIG. 33D).

Figure 34:
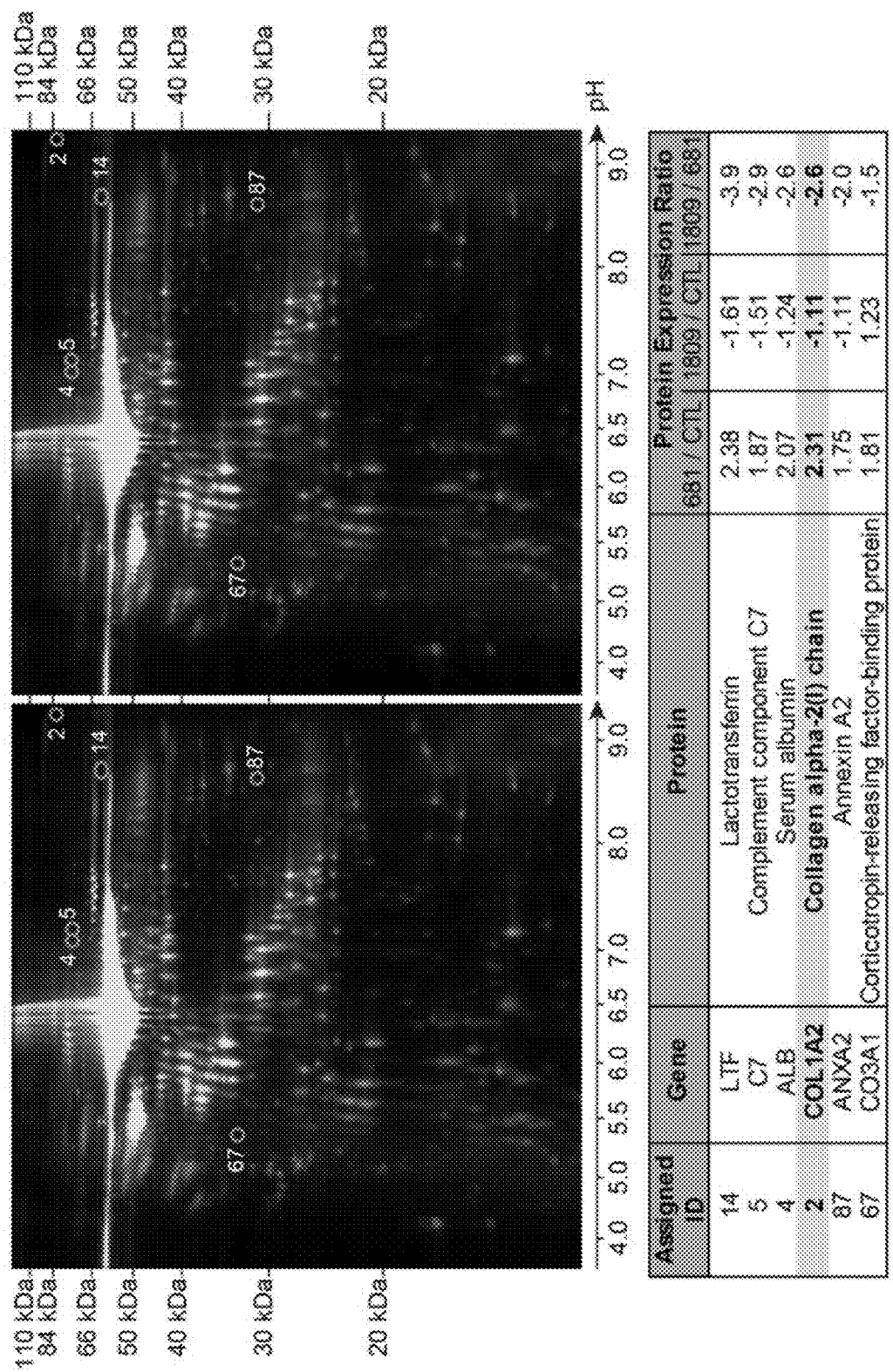
FIG. 34 shows an exemplary embodiment of pNF-associated NF1-mutant PNS neurons exhibit increased activity and COL1A2-dependent preneoplastic NF1$^{-/-}$ Schwann cell growth in accordance with the present disclosure.
Figure 35A:
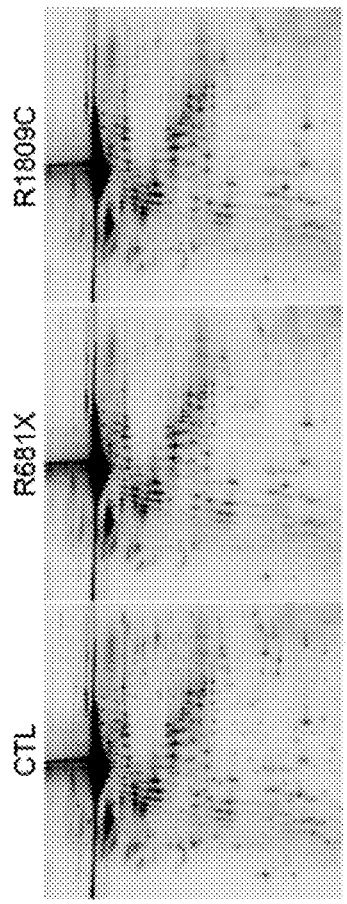
FIG. 35A-FIG. 35B shows an exemplary embodiment of COL1A2 is uniquely expressed by NF1-mutant peripheral nervous system neurons in accordance with the present disclosure.
Figure 35B:
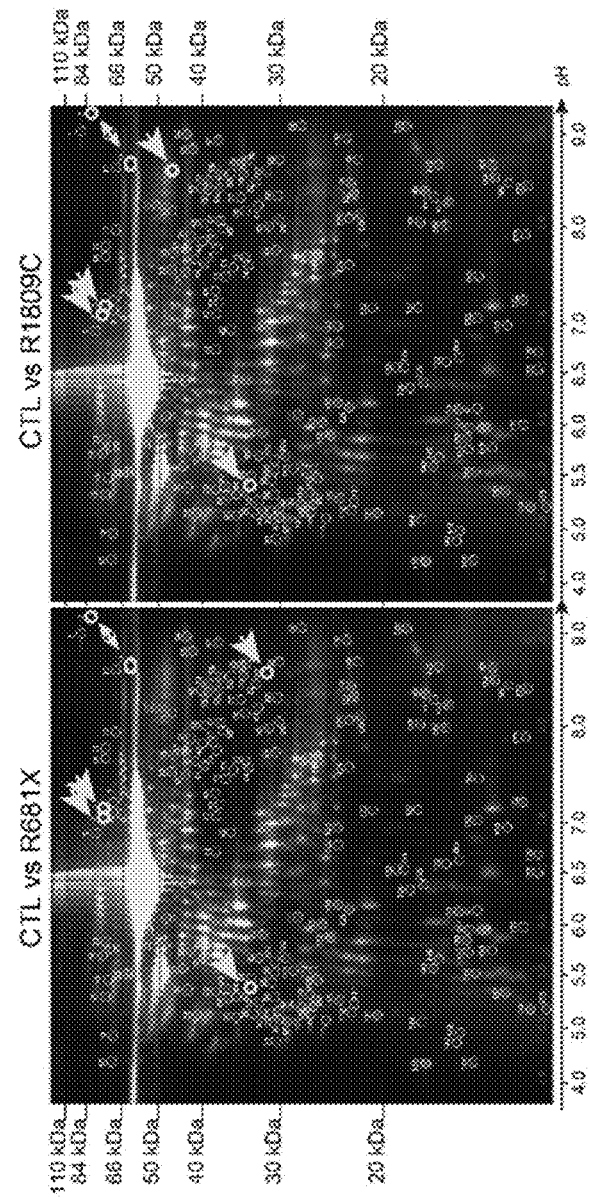
Figures 36A, 36B, 37A:
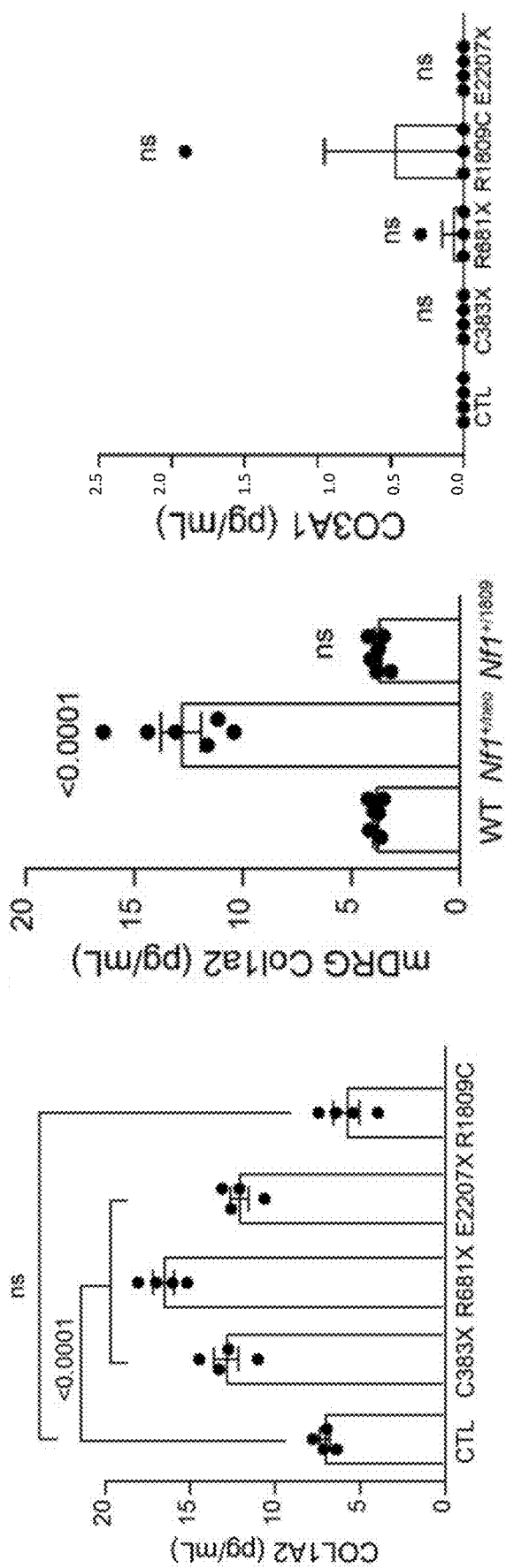
FIG. 36A-FIG. 36B shows an exemplary embodiment of pNF-associated NF1-mutant PNS neurons exhibit increased activity and COL1A2-dependent preneoplastic NF1$^{-/-}$ Schwann cell growth in accordance with the present disclosure.
FIG. 37A-FIG. 37E shows an exemplary embodiment of COL1A2 is uniquely expressed by NF1-mutant peripheral nervous system neurons in accordance with the present disclosure.
Figures 37B, 37C, 37D:
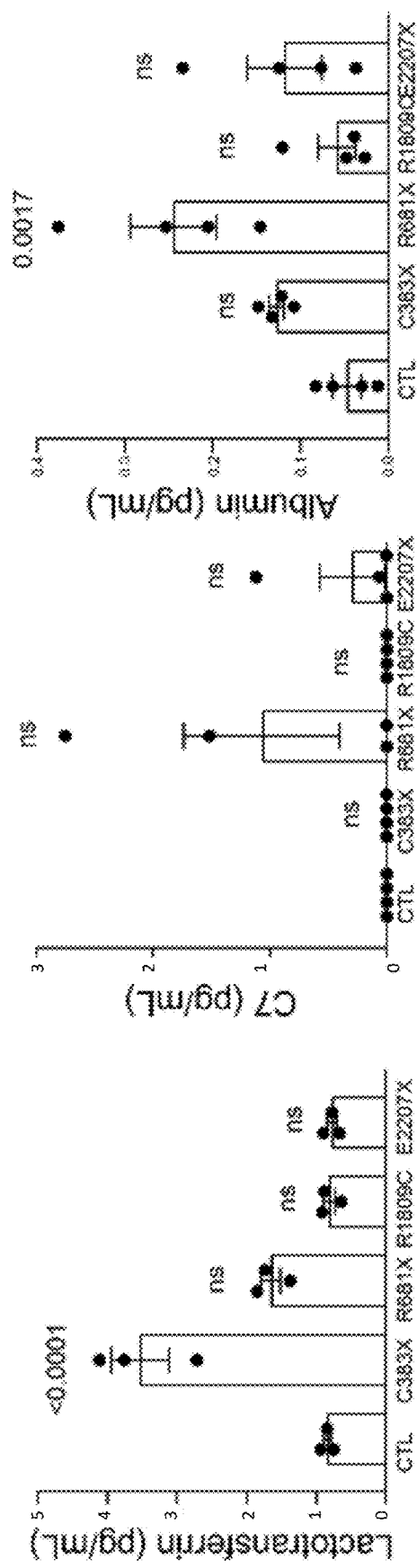
Figure 39A:
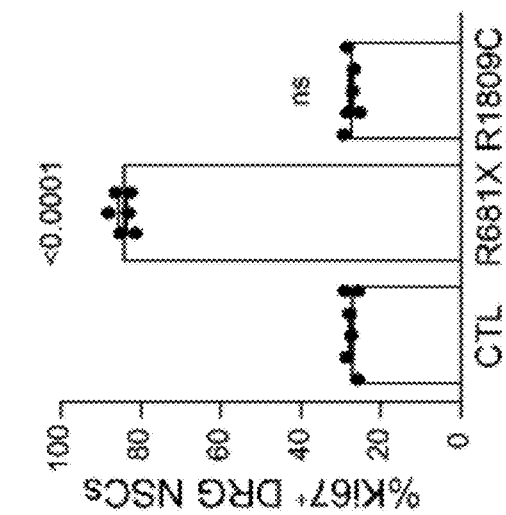
FIG. 39A-FIG. 39B shows an exemplary embodiment of COL1A2 is uniquely expressed by NF1-mutant peripheral nervous system neurons in accordance with the present disclosure.
Figure 38:
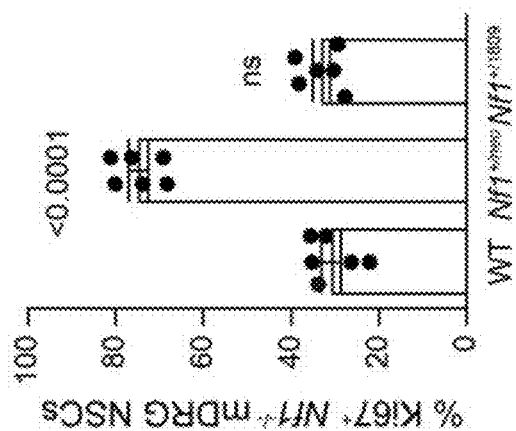
FIG. 38 shows an exemplary embodiment of pNF-associated NF1-mutant PNS neurons exhibit increased activity and COL1A2-dependent preneoplastic NF1$^{-/-}$ Schwann cell growth in accordance with the present disclosure.
Figure 37E:
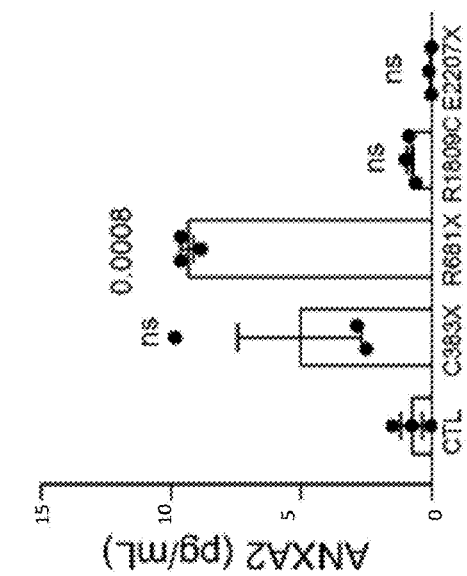
Figure 39B:
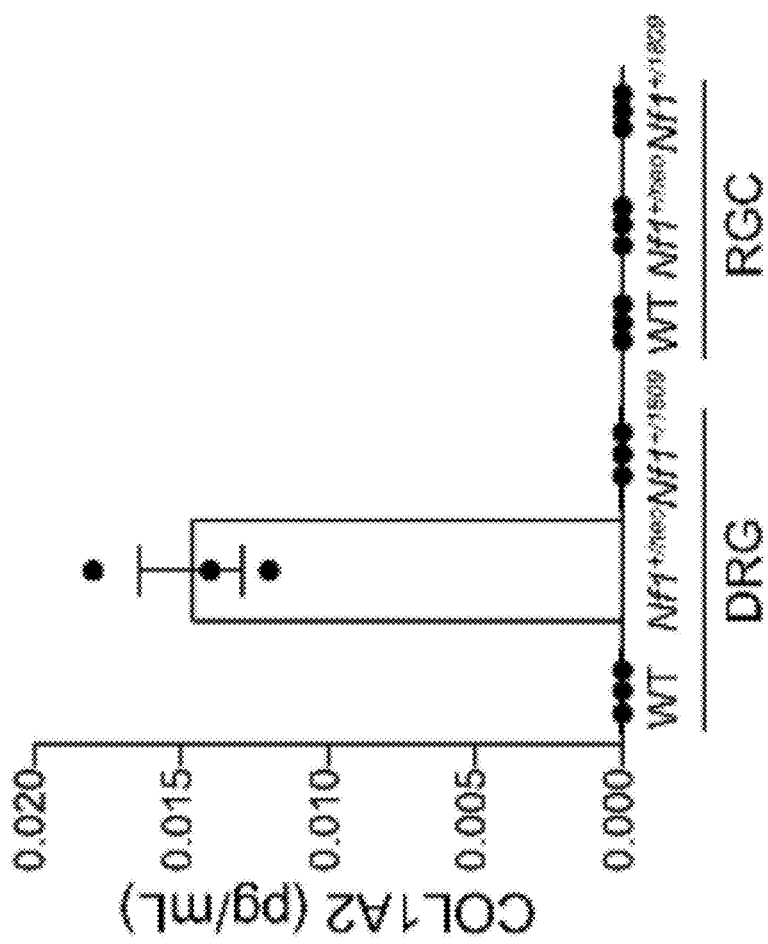

Leveraging these observations, unbiased protein secretome analyses on CM from control, and representative sensory neurons from group 1 (NF1R681X) and group 2 (NF1R1809C; see e.g., FIG. 34 and FIG. 35A-FIG. 35B) were leveraged. The secreted proteins from both NF1-mutant neurons were compared to those of the controls and each differentially regulated protein was assigned an arbitrary identification number. From the 176 differentially regulated proteins, the expression of six proteins was uniquely increased more than 1.5-fold in the tumor-associated NF1R681X CM but not in the non-tumor-associated NF1-R1809C CM relative to control CM (see e.g., FIG. 34). As a secondary validation, CM from independently generated sensory neurons was used to confirm the presence and concentration of the six identified proteins. Of these, only COL1A2 was elevated in the CM from the tumor-associated group 1, but not in the non-tumor-associated group 2, hiPSC-sensory neurons, as well as in mouse Nf1$^{+/neo}$ but not Nf1$^{+/1809}$ DRG neurons (2.4-3.2-fold increase; see e.g., FIG. 36A-FIG. 36B and FIG. 37A-FIG. 37E). Importantly, both Nf1$^{+/neo}$ mouse DRG (see e.g., FIG. 38) and NF1-R681X hiPSC-sensory neuron CM (see e.g., FIG. 39A) increased Nf1$^{-/-}$ DRG-NSCs (murine Schwann cell progenitors) proliferation (2-8-3.1-fold increase in % Ki67$^+$ cells) relative to control and Nf1$^{+/1809}$ or NF1-R1809C neuron CM. Notably, COL1A2 was uniquely expressed by NF1-mutant PNS, but not CNS, neurons (see e.g., FIG. 39B).

COL1A2 is Both Necessary and Sufficient for Preneoplastic NF1-Null Schwann Cell Proliferation In Vitro.

Figure 40A:
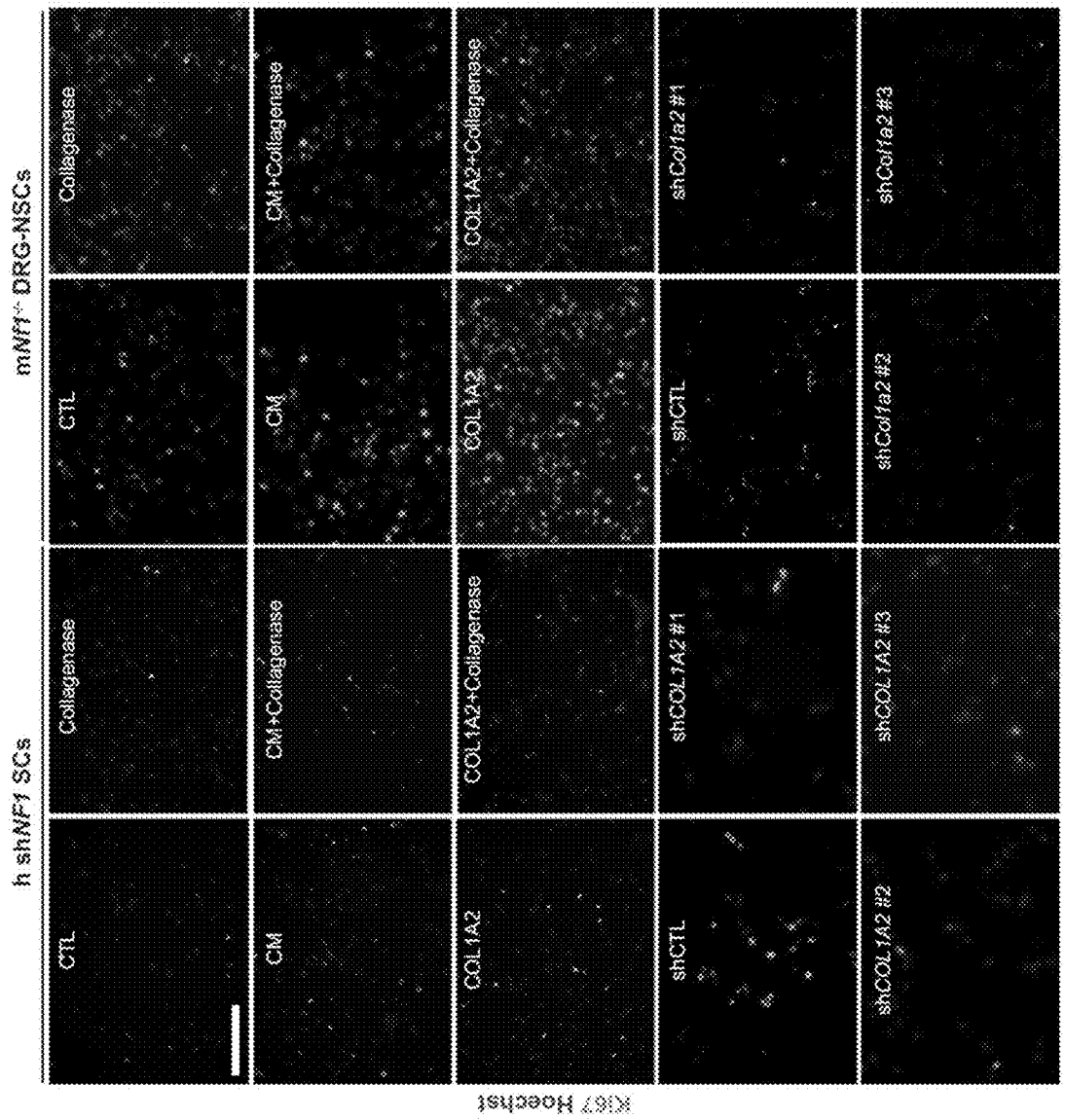
FIG. 40A-FIG. 40B shows an exemplary embodiment of COL1A2 is necessary and sufficient for NF1-deficient Schwann cell growth in vitro in accordance with the present disclosure.
Figure 40B:
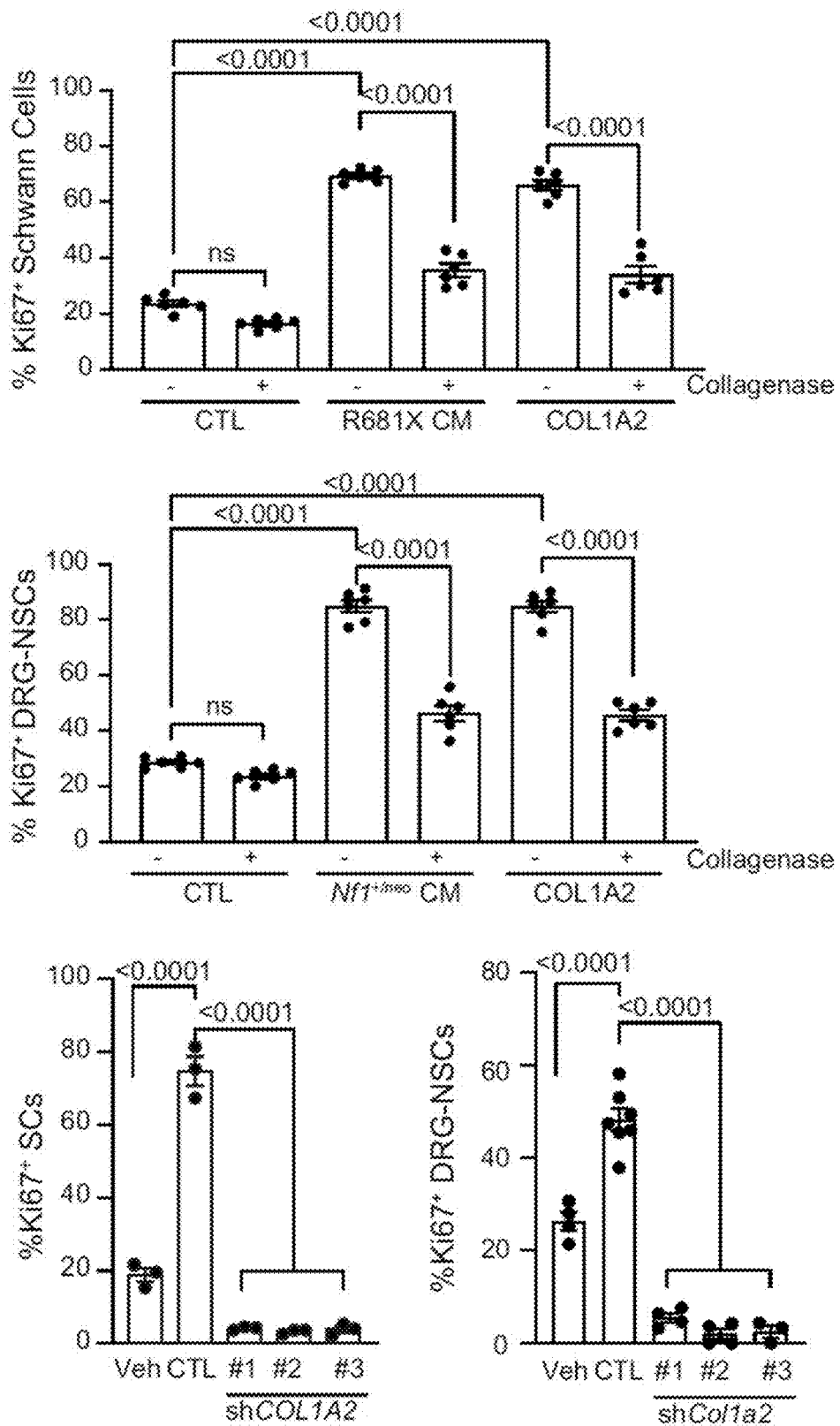
Figure 41C:
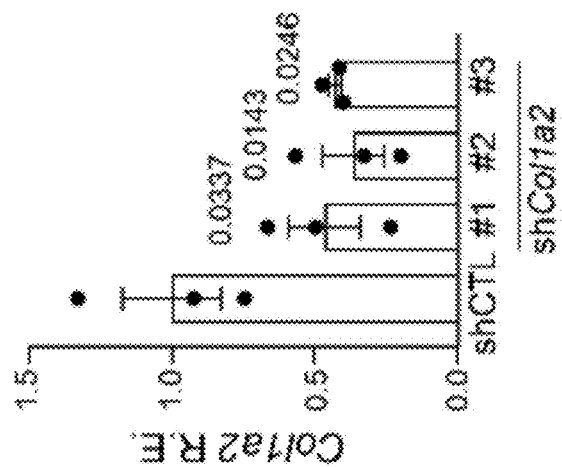
FIG. 41A-FIG. 41D shows an exemplary embodiment of COL1A2 is uniquely expressed by NF1-mutant peripheral nervous system neurons in accordance with the present disclosure.
Figure 41B:
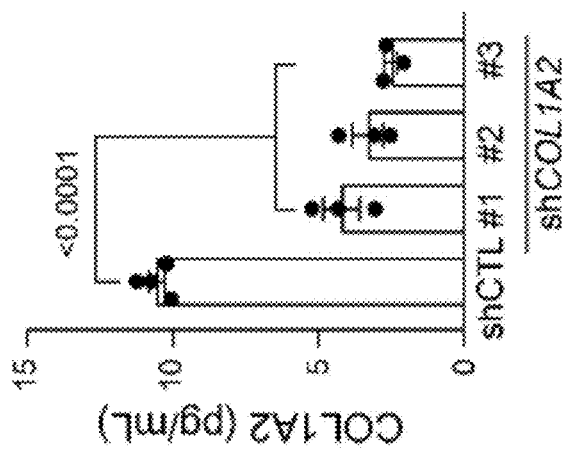
Figure 41A:
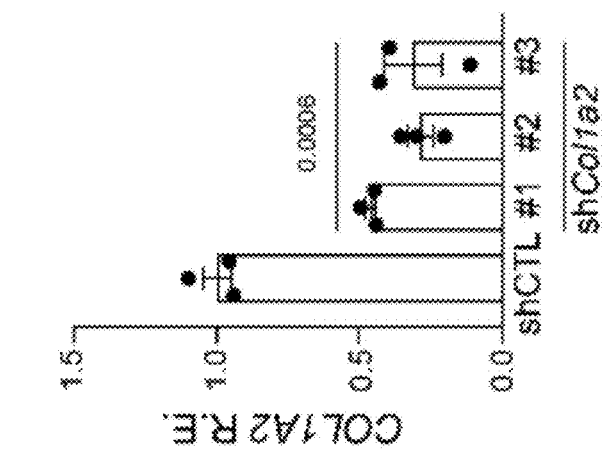
Figure 41D:
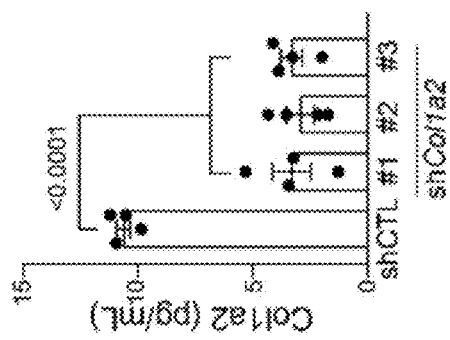
Figure 42A:
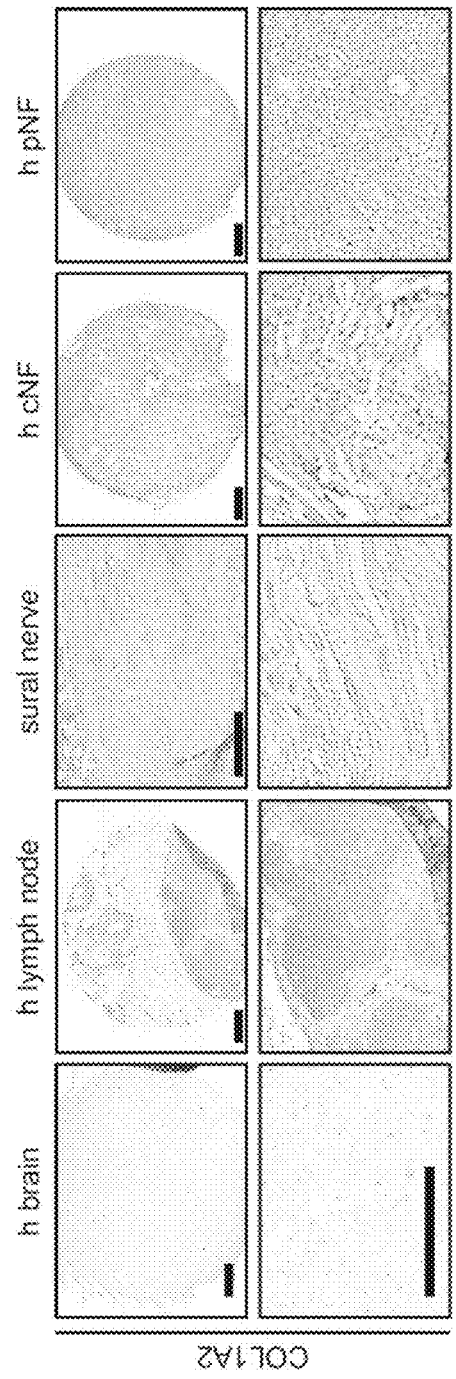
FIG. 42A-FIG. 42D shows an exemplary embodiment of COL1A2 is necessary and sufficient for NF1-deficient Schwann cell growth in vitro in accordance with the present disclosure.
Figure 42B:
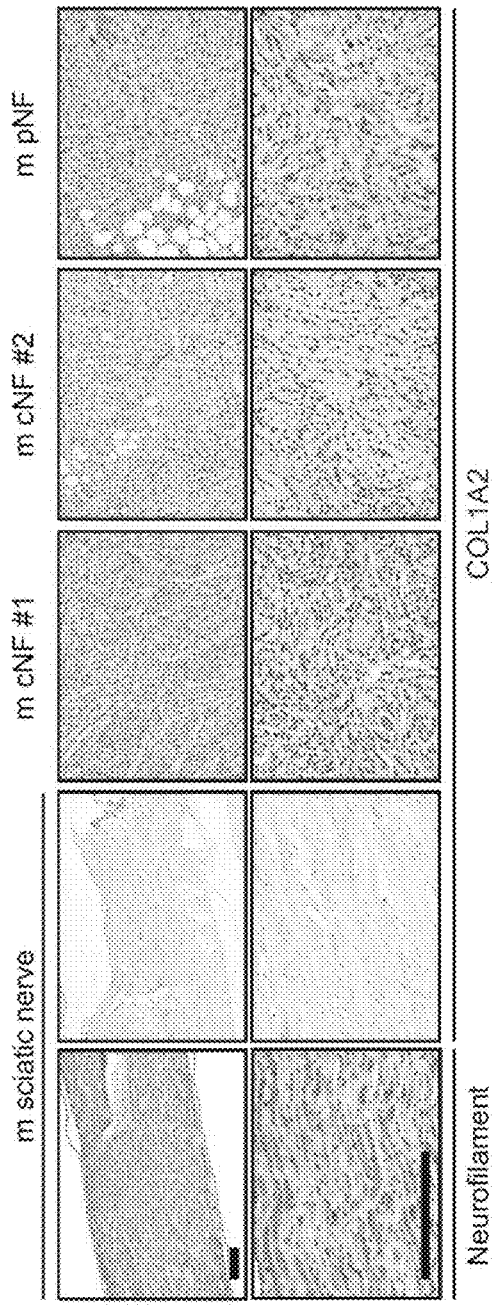
Figure 42C:
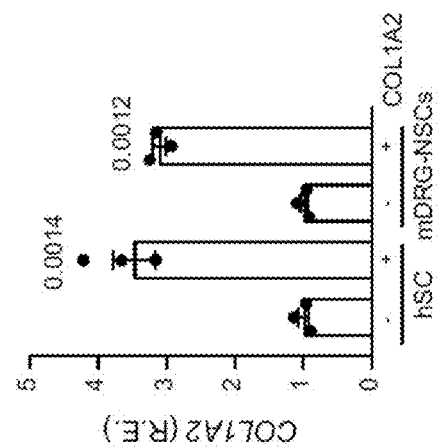
Figure 42D:
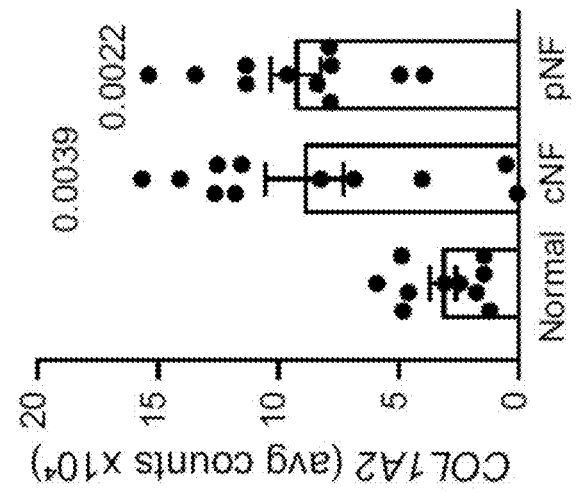

To determine whether COL1A2 can increase NF1-deficient preneoplastic Schwann cell proliferation in vitro, human shNF1 SCs and murine Nf1$^{-/-}$ DRG NSCs were treated with COL1A2 at the concentration quantified in sensory neuron CM (12.5 μg/mL). As such, COL1A2 treatment increased the proliferation of shNF1 SCs and Nf1$^{-/-}$ DRG NSCs (2.5-2.9-fold increase in Ki67$^+$ cells) to levels similar to NF1-mutant sensory neuron CM. The increase in proliferation conferred by NF1-mutant sensory neuron CM or COL1A2 alone was completely abrogated by neuron treatment with collagenase (see e.g., FIG. 40A-FIG. 40B), as well as by genetic COL1A2 short hairpin-mediated genetic reduction (shCOL1A2 1-3; 65.1% reduction, see e.g., FIG. 41A-FIG. 41B and FIG. 40A-FIG. 40B), or Col1a2 (shCol1a2 1-3; 70.2% reduction, see e.g., FIG. 41C-FIG. 41D and FIG. 40A-FIG. 40B). In addition, both human (see e.g., FIG. 42A) and murine (see e.g., FIG. 42B) cutaneous and plexiform neurofibromas exhibited strong COL1A2 immunoreactivity, in contrast to minimal expression in normal sural and sciatic nerves, lymph nodes, or brain. Similar to neuroligin-3 autocrine regulation of tumoral NLGN3 production, incubation of shNF1 SCs and Nf1$^{-/-}$ DRG NSCs with COL1A2 induced a feed-forward increase in COL1A2 transcript levels (see e.g., FIG. 42C). This feed-forward induction suggests a paracrine effect of neuronal COL1A2 on preneoplastic Schwann cell COL1A2 transcription. Consistent with these findings, Schwann cells isolated from human cNFs or pNFs express higher levels of COL1A2 relative to non-neoplastic SCs (see e.g., FIG. 42D). Together, these findings establish COL1A2 as a unique neuronal-secreted factor critical for pNF-associated NF1$^{-/-}$ neoplastic Schwann cell proliferation.

COL1A2 Secretion is Neuronal Activity-Dependent.

Figure 43B:
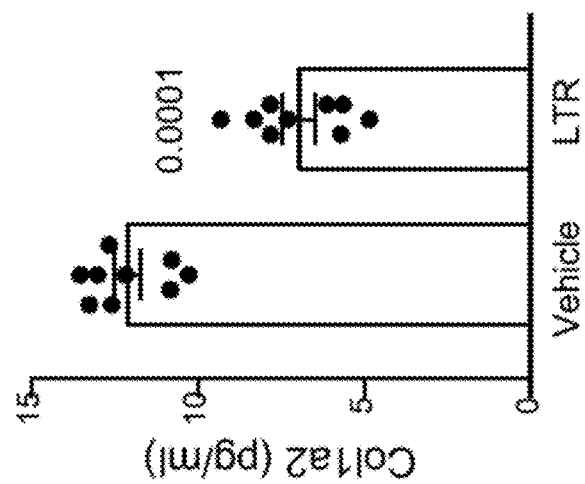
FIG. 43A-FIG. 43H shows an exemplary embodiment of Col1a2 secretion is regulated by HCN channel-regulated sensory neuron activity in accordance with the present disclosure.
Figure 43A:
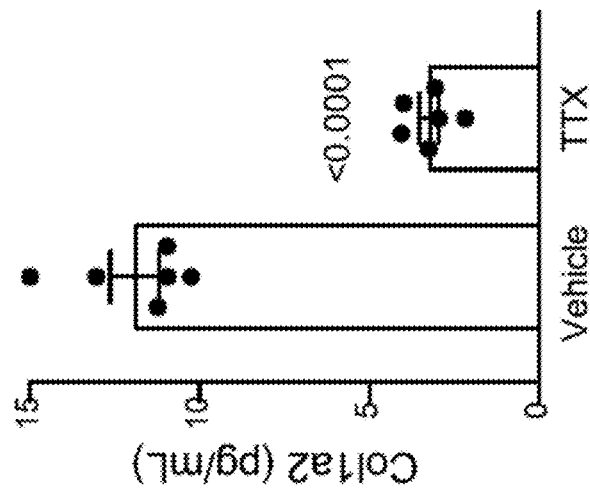
Figures 43C, 43D, 43E:
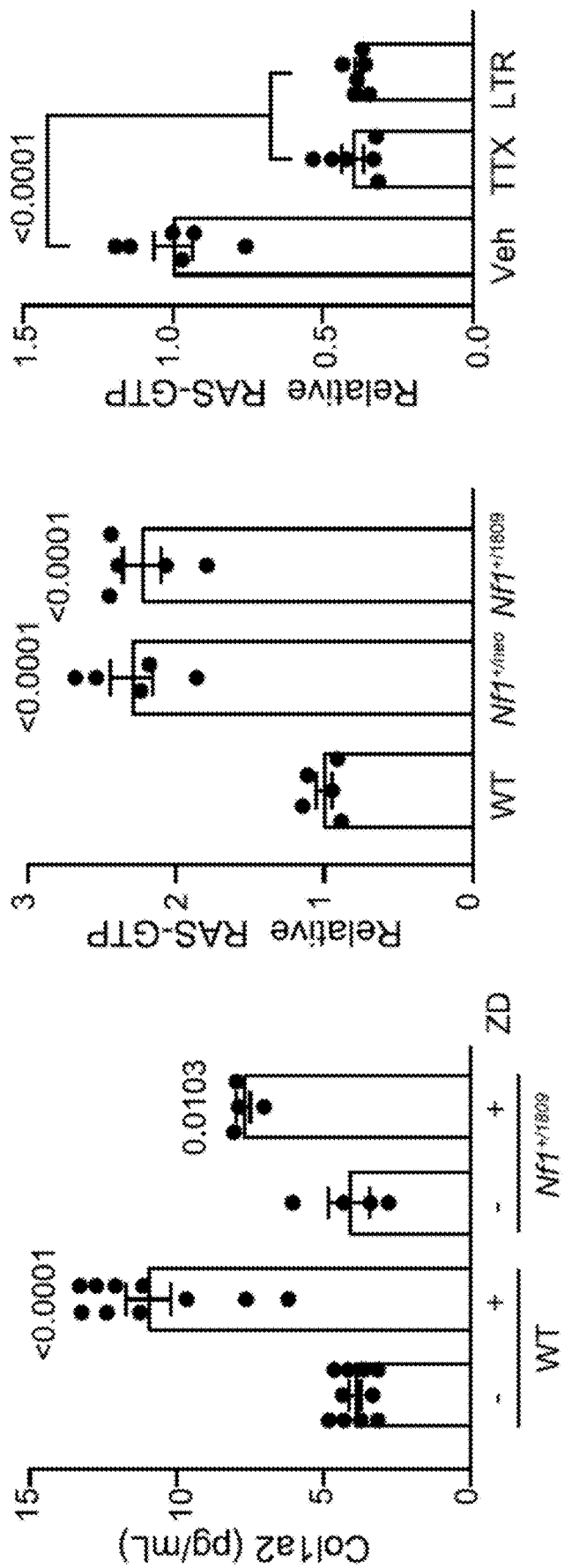
Figure 43F:
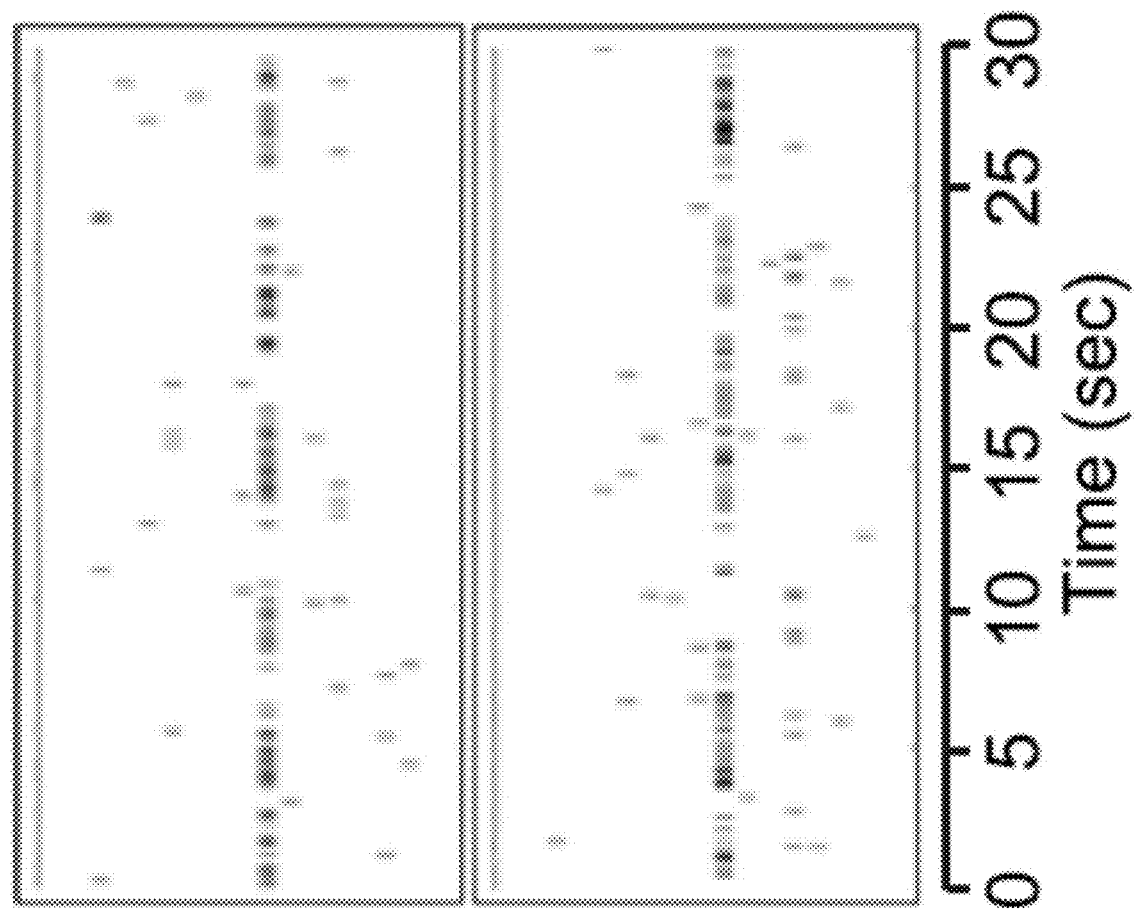
Figure 43F:
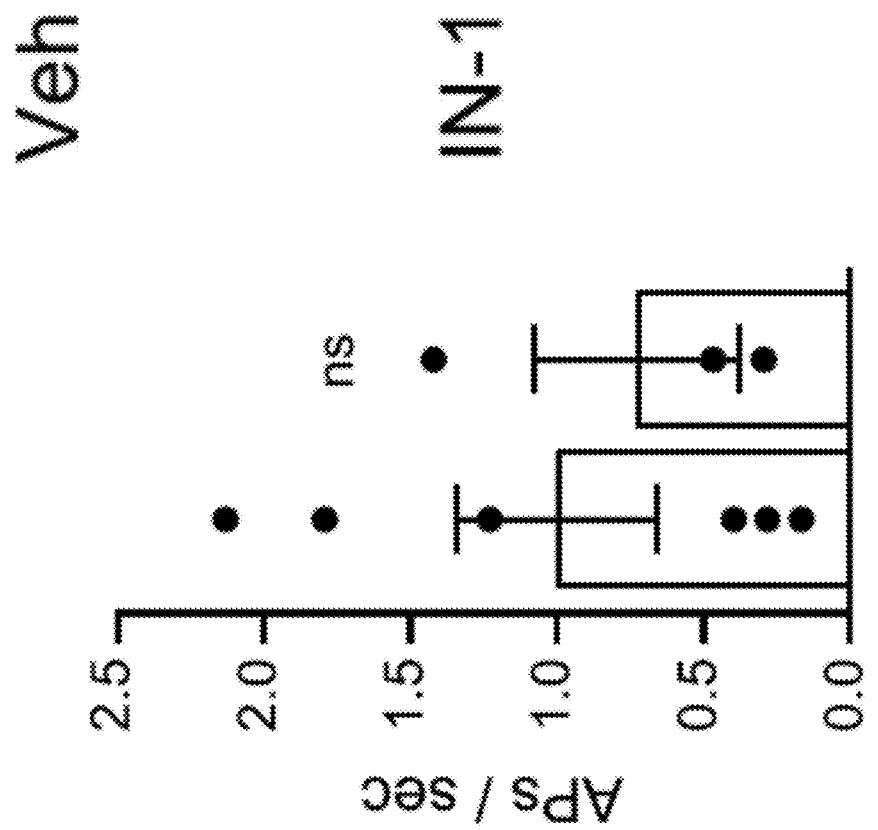
Figure 43G:
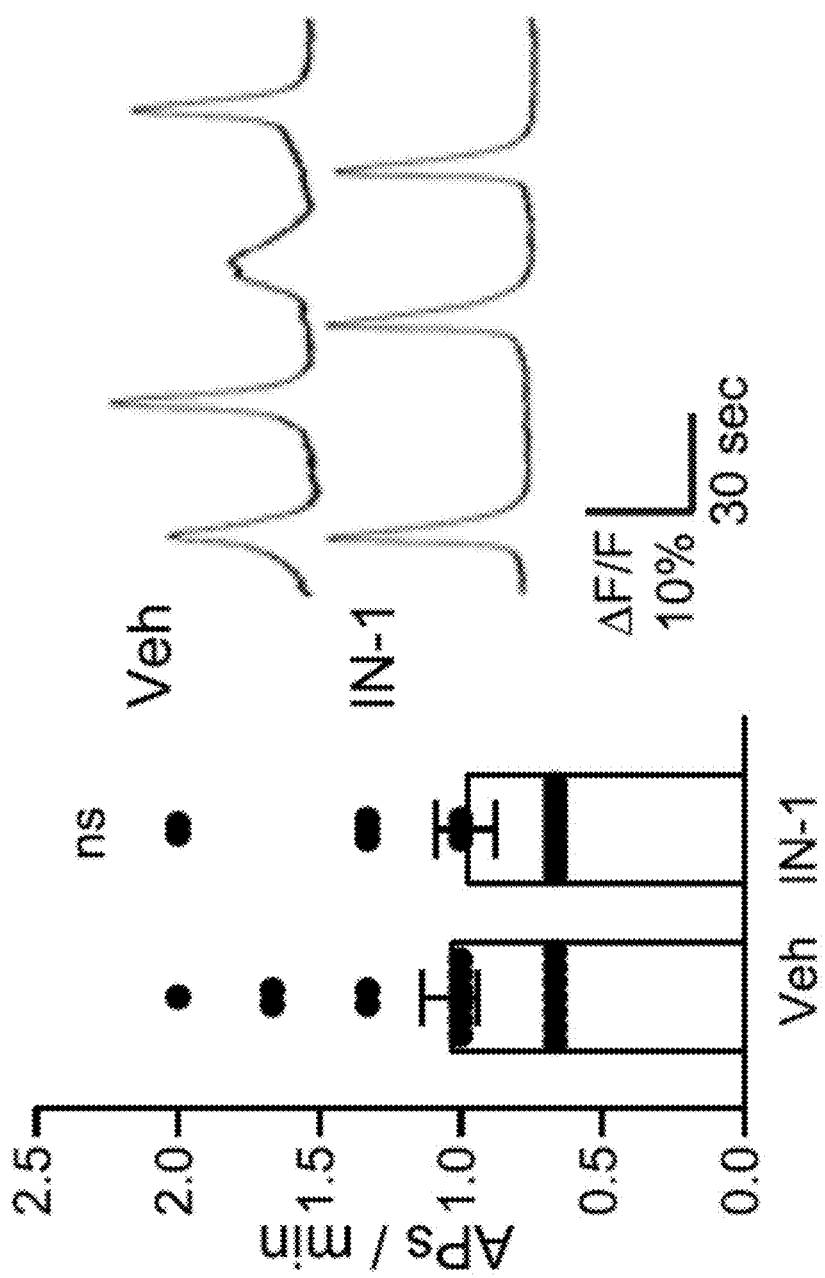
Figure 43H:
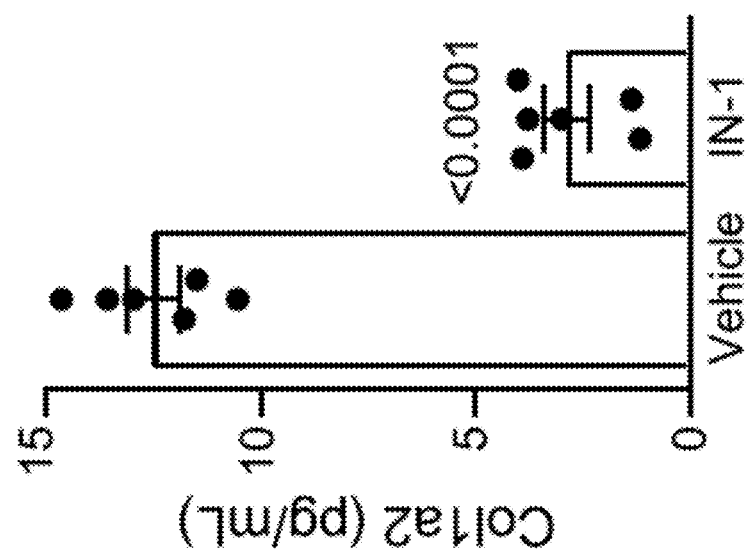
Figure 44A:
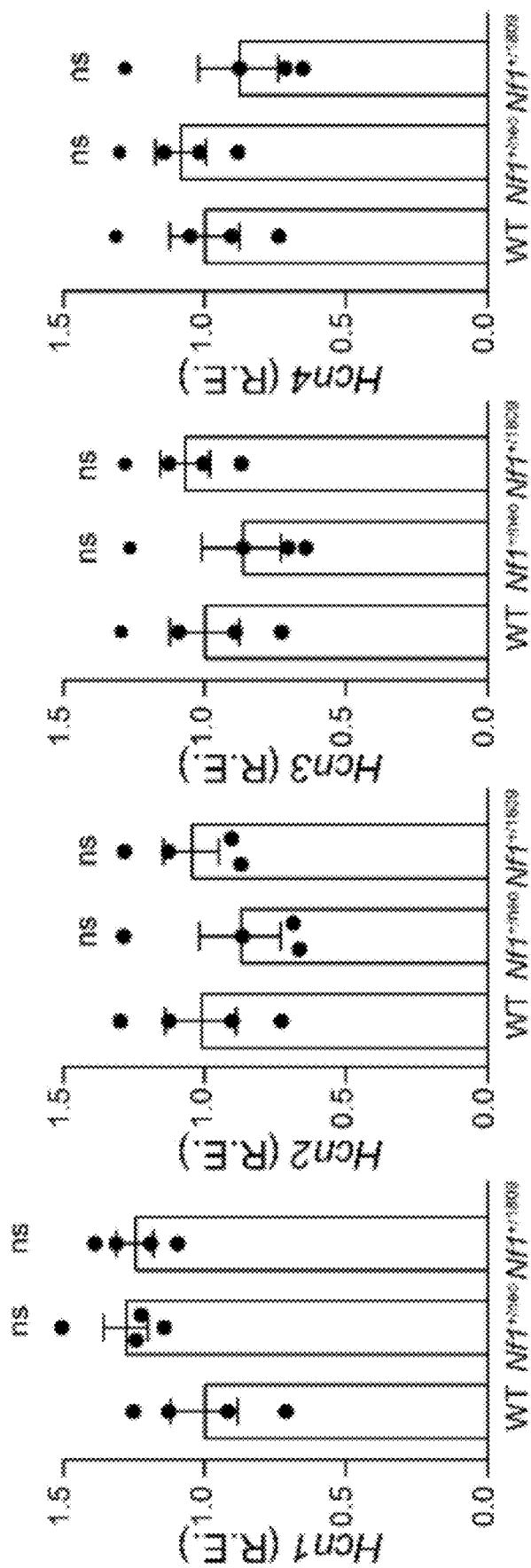
FIG. 44A-FIG. 44C shows an exemplary embodiment of COL1A2 is uniquely expressed by NF1-mutant peripheral nervous system neurons in accordance with the present disclosure.
Figures 44B, 44C, 45A:
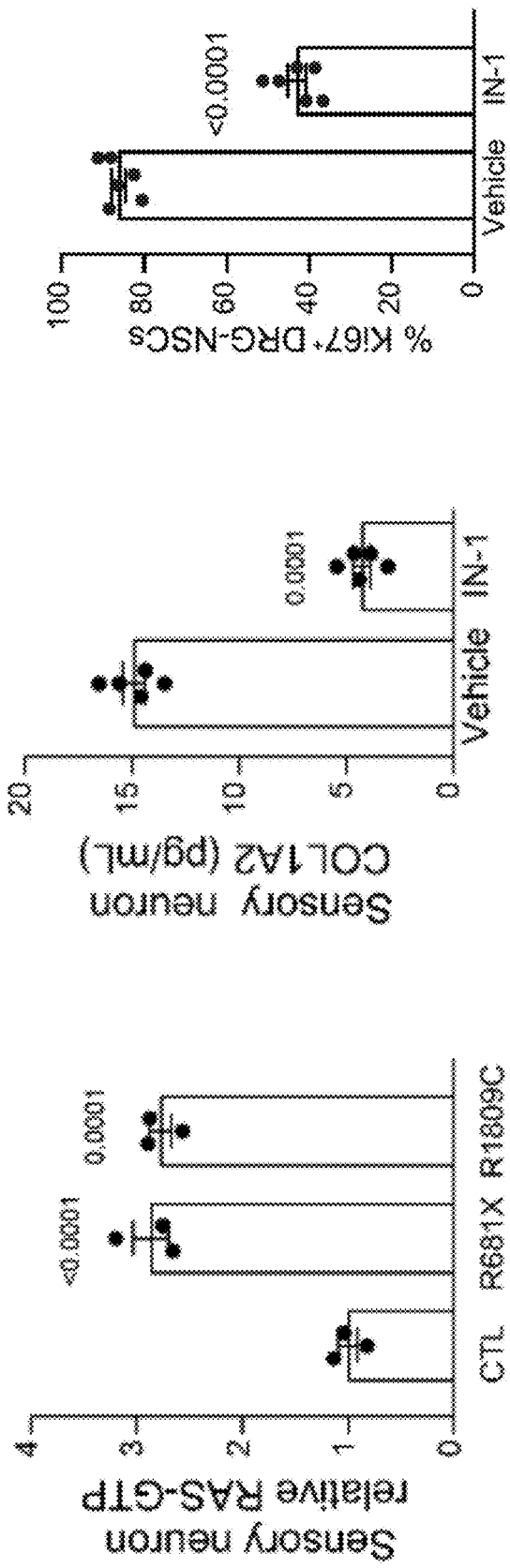
FIG. 45A-FIG. 45B shows an exemplary embodiment of Col1a2 secretion is regulated by HCN channel-regulated sensory neuron activity in accordance with the present disclosure.
Figure 45B:
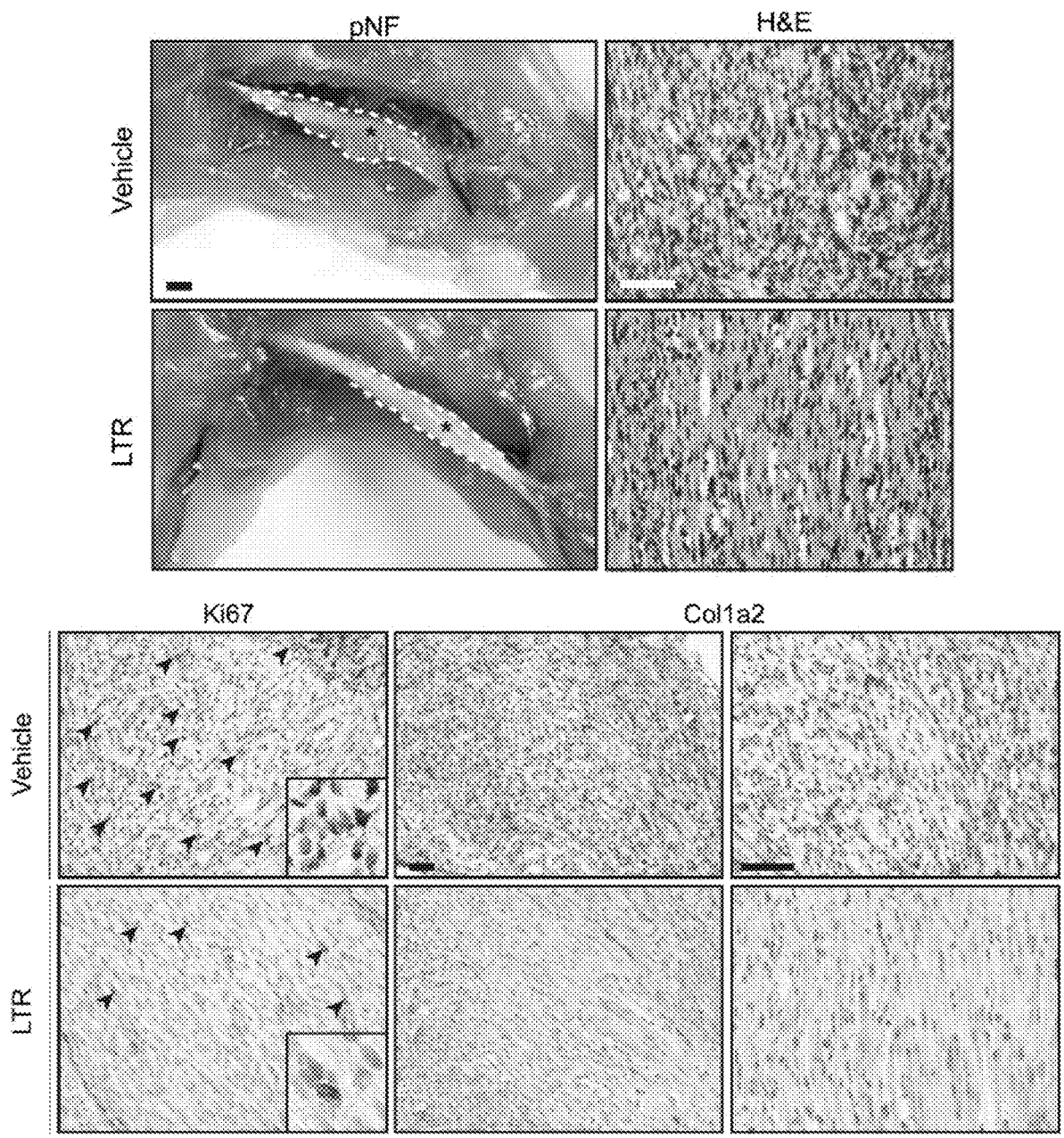
Figure 49A:
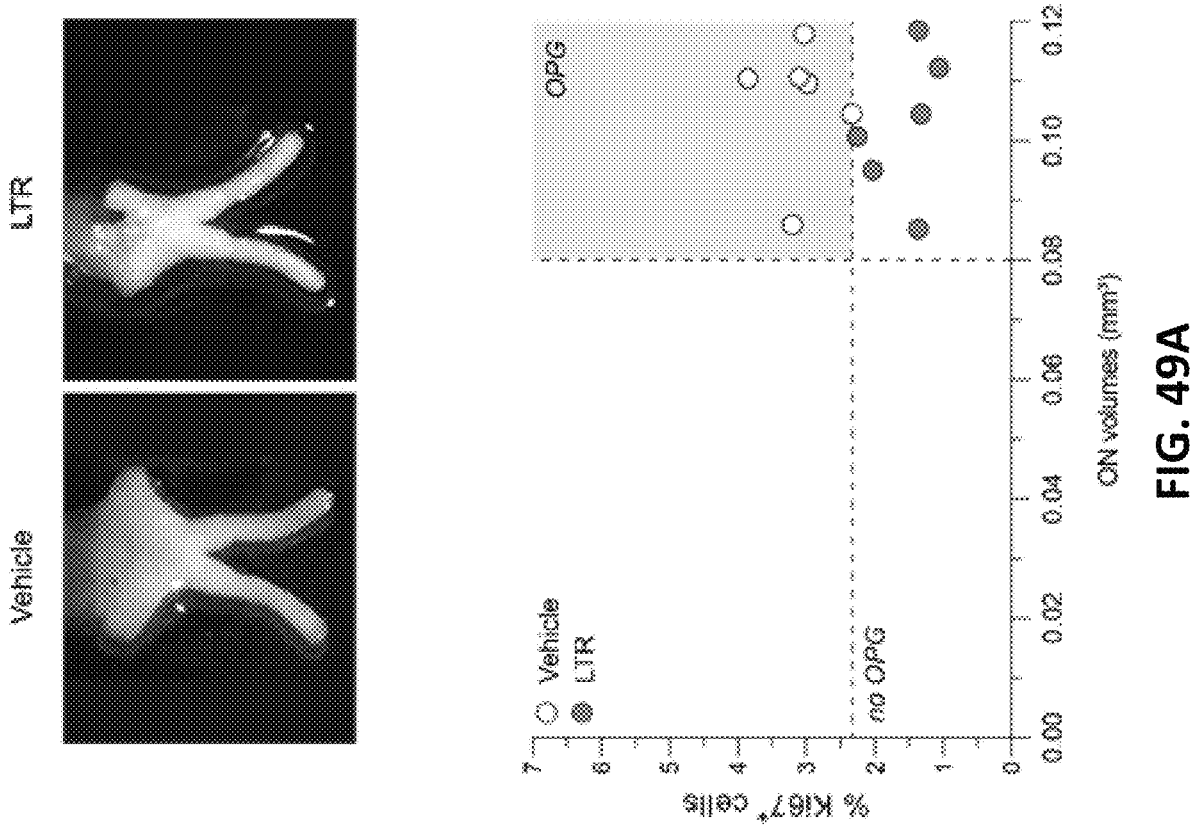
FIG. 49A-FIG. 49B shows an exemplary embodiment of lamotrigine in accordance with the present disclosure. Lamotrigine treatment from 4-8 weeks had a durable effect in reducing optic nerve proliferation (% Ki67+ cells; 1.5-fold decrease), as well as microglia (% Iba1+ cells; 1.4-fold decrease) content in 6 month-old treated Nf1-OPG mice, relative to vehicle-treated Nf1-OPG mice.
Figure 49B:
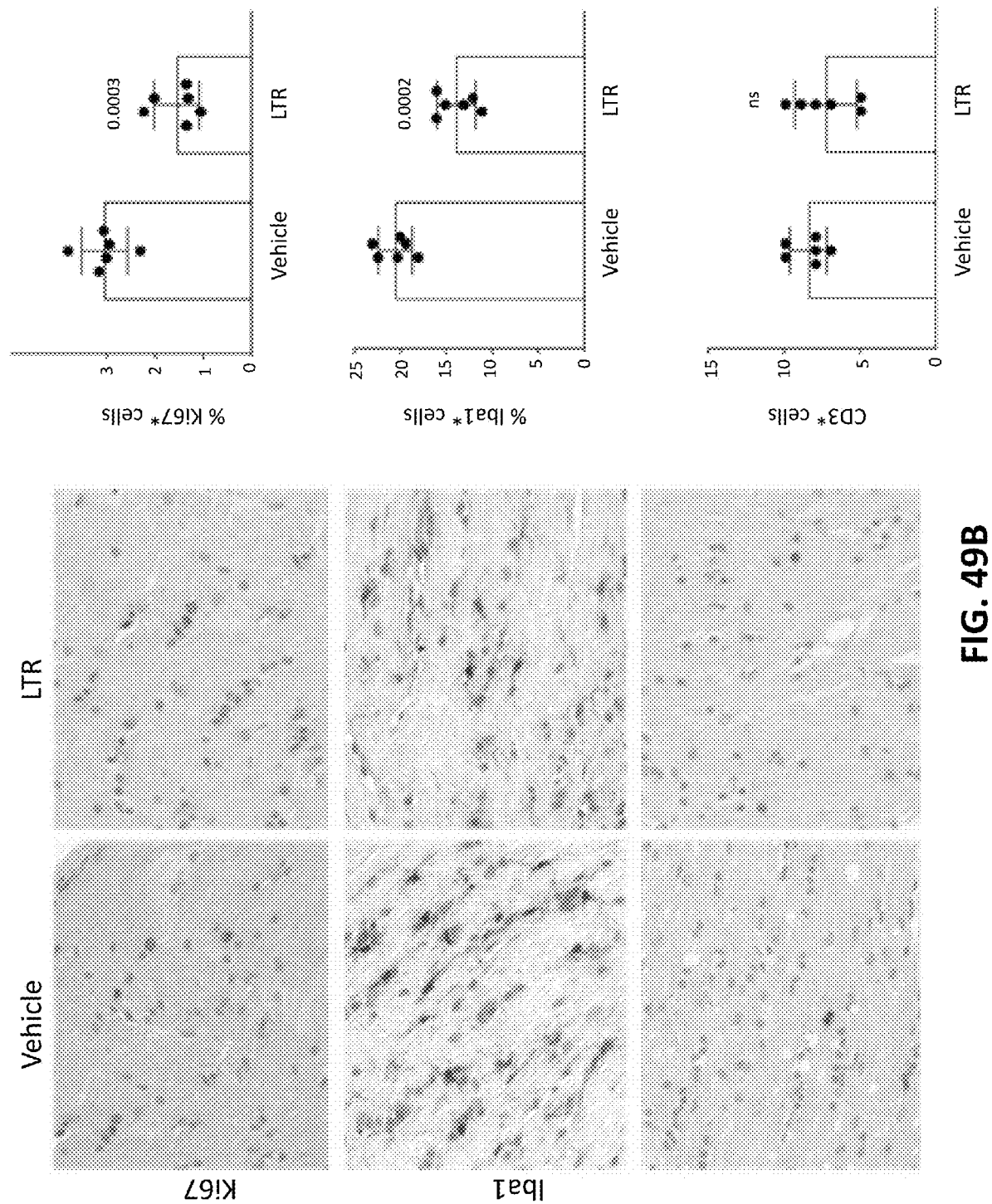
Figure 50:
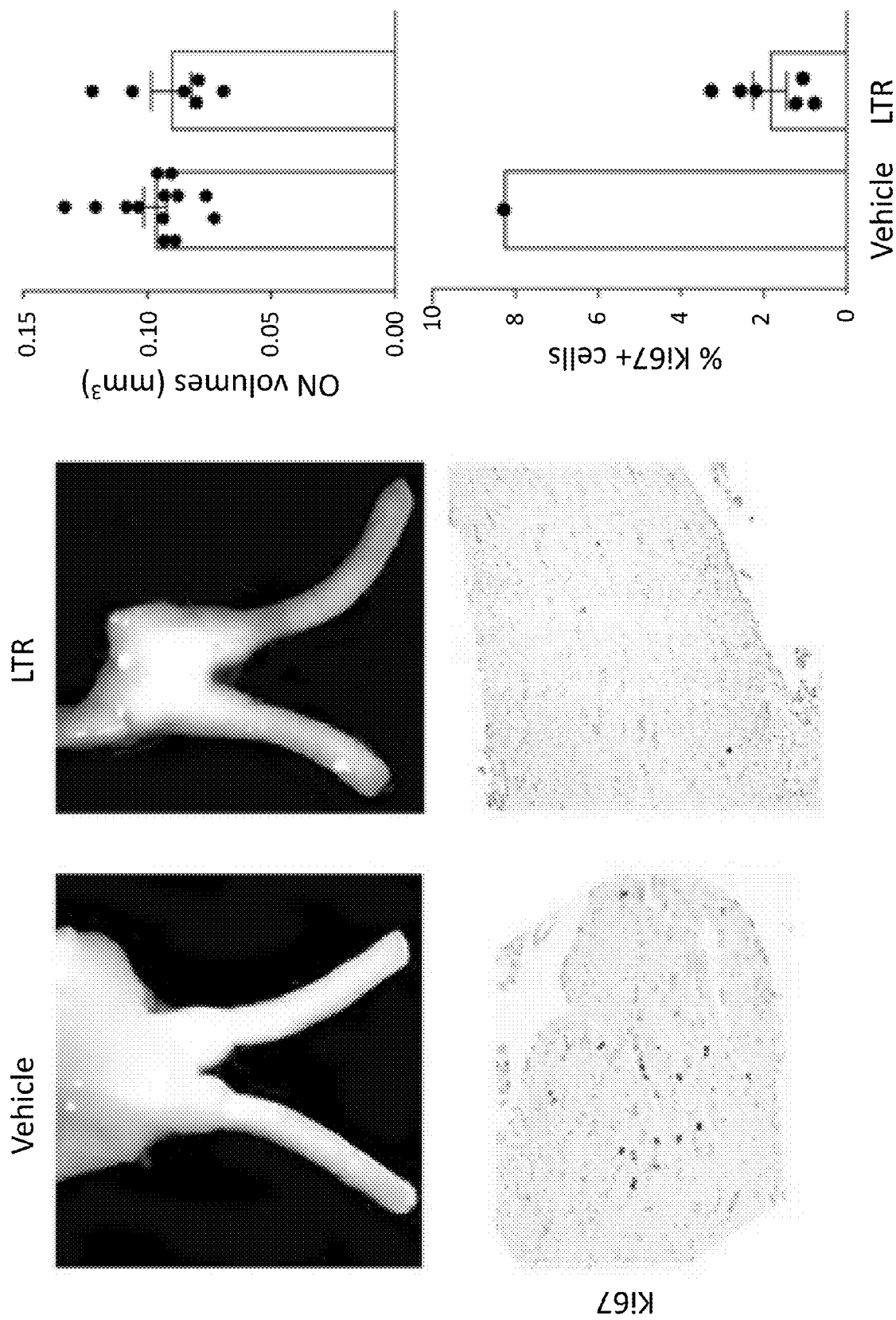
FIG. 50 is an exemplary embodiment of lamotrigine treatment with human dosing and parameters (oral gavage, 10 mg/kg/day) reducing optic nerve proliferation (% Ki67+ cells; 4-fold decrease) content in 3 month-old treated Nf1-OPG mice, relative to vehicle-treated Nf1-OPG mice, in accordance with the present disclosure.

To determine whether neuronal excitability similarly controls PNS mitogen secretion, Col1a2 was analyzed in CM from TTX- and lamotrigine-treated Nf1$^{+/neo}$ DRG neurons. Similar to midkine in their CNS counterparts, both TTX and lamotrigine reduced Nf1$^{+/neo}$ DRG neuronal Col1a2 secretion (3.6-, 1.8-fold reduction, respectively; see e.g., FIG. 43A-FIG. 43B), while ZD7288 increased DRG Col1a2 secretion in WT and Nf1$^{+/1809}$ DRG neurons (2-2.8-fold increase; see e.g., FIG. 43C). In addition, RAS activity was higher in both Nf1$^{+/neo}$ and Nf1$^{+/1809}$ DRG neurons (2.1-fold increase, see e.g., FIG. 43D). The increased RAS activity in Nf1$^{+/neo}$ DRG neurons was reduced following neuronal activity inhibition either by TTX or lamotrigine exposure (2.5-2.7-fold decrease; see e.g., FIG. 43E). In addition, RAS inhibition had no effect on DRG neuronal activity (see e.g., FIG. 43F-FIG. 43G), but reduced COL1A2 expression both in mouse (4.5-fold reduction, see e.g., FIG. 43H) and human (2.6-fold reduction; see e.g., FIG. 44A-FIG. 44C) sensory neurons, and decreased Nf1$^{-/-}$ DRG-NSC proliferation in vitro (see e.g., FIG. 45A). These findings demonstrate that Col1a2 is secreted by tumor-associated Nf1$^{+/neo}$ sensory neurons in an HCN channel activity-dependent manner. Finally, to determine whether HCN channel function can govern pNF progression in vivo, mice harboring NF1-pNFs received intraperitoneal injections of lamotrigine for 6 weeks. HCN activation reduced pNF size, partly restored neuronal histology, and reduced both proliferation (Ki67$^+$ cells), as well as Col1A2 immunoreactivity, within the tumors (see e.g., FIG. 45B). Together, these data firmly establish that HCN channel-mediated sensory neuron Col1a2 production regulates pNF progression in vivo. See also FIG. 49A, FIG. 49B, and FIG. 50.

DISCUSSION

Figure 46A:
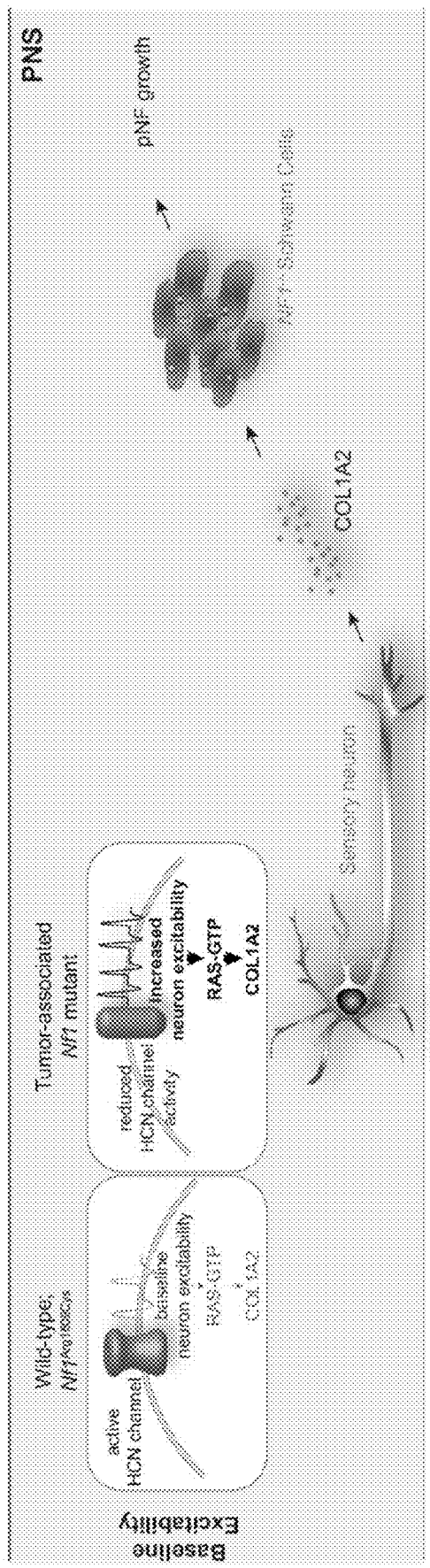
FIG. 46A-FIG. 46B shows an exemplary embodiment of the proposed model for NF1 mutation-induced, neuronal hyperexcitability-regulated low-grade tumor growth in accordance with the present disclosure.
Figure 46B:
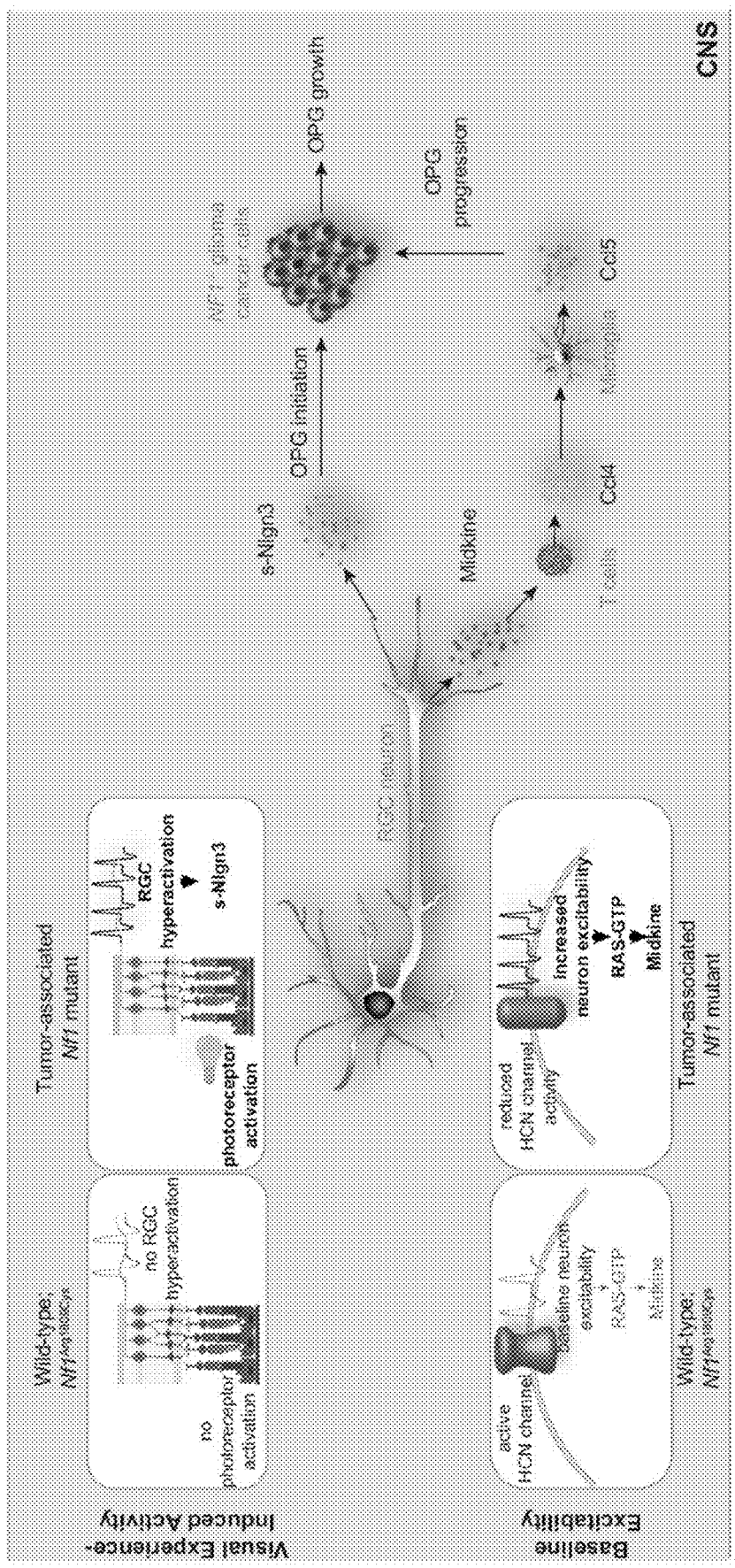

Exploiting a unique, naturally occurring germline mutation in patients with the NF1 tumor predisposition syndrome who fail to develop neurofibromas or optic gliomas (Arg1809Cys), hiPSCs and genetically engineered mice were employed to identify two distinct mechanisms underlying neuronal activity regulation of nervous system tumor progression (see e.g., FIG. 46A-FIG. 46B). In this study, and similar to what is observed in patients with NF1, it was shown that Nf1$^{+/1809}$ mice do not form pNFs or OPGs. Consistent with the lack of tumor formation, Arg1809Cys-mutant neurons do not induce Adam10-mediated cleavage and shedding of Nlgn3, a growth factor required for murine Nf1-OPG initiation and growth. In addition, a neuron-immune-cancer cell axis was previously described, where neurons indirectly regulate Nf1-OPG progression through their effects on T-cell Ccl4-mediated induction of microglial growth factor (Ccl5) production. Since Nf1$^{+/1809}$ T cells produce Ccl4 in response to midkine and Nf1$^{+/1809}$ microglia produce Ccl5 in response to Ccl4, the Arg1809Cys mutation appears to operate at the level of the neuron, such that human and mouse neurons with this mutation fail to increase midkine expression or activate optic glioma-infiltrating T cells to drive Nf1-OPG progression. Importantly, tumor initiation may also be influenced by the germline Nf1 mutation acting on the tumor cells of origin, requiring investigations of the impact of the NF1 Arg1809Cys mutation on third ventricle neural progenitors (OPG) and Sox10$^+$, GAP43$^+$ Schwann cell precursors (neurofibroma). Second, COL1A2 was identified as a sensory neuron-derived paracrine factor important for NF1-deficient Schwann cell proliferation.

Of note, Schwann cells are the neoplastic cells of two distinct types of tumors, neurofibromas, and schwannomas, which differ both in pathology and immunohistochemical profiles. Specifically, neurofibromas, which occur both sporadically and in the setting of NF1, are heterogeneous tumors with small and wavy nuclei, excess "shredded" type collagen, and are immunopositive for neurofilament expression. In contrast, schwannomas arising either sporadically or in patients with neurofibromatosis type 2 (NF2) and Schwannomatosis are encapsulated tumors with more homogeneous Schwann cell proliferation, larger nuclear sizes, and the presence of hyalinized vessels. The importance of collagen to neurofibroma-associated Schwann cell growth is underscored by the observation that collagen accounts for the majority of the extracellular matrix in human neurofibromas and as much as 50% of neurofibroma dry weight.

While type 1 collagens increase Schwann cell and Schwann cell progenitor adhesion, survival, and proliferation, it was shown herein that NF1 mutation in human and mouse peripheral sensory neurons induces activity-dependent production of COL1A2, which, similar to NLGN3 in the brain, induces a feed-forward loop of COL1A2 transcription in Schwann cells and Schwann cell progenitors, resulting in elevated tumoral collagen levels. While the abundance of collagen and its production by other cell types (fibroblasts) in neurofibromas prompted human clinical trials with broad-spectrum anti-fibrotic agents, like Pirfenidone, no efficacy was observed, possibly due to the low abundance of collagen-synthesizing fibroblasts in pNFs. Ongoing studies are focused on determining whether targeting of sensory neuron-specific COL1A2 production will reduce neurofibroma growth.

Third, examination of NF1$^{+/1809}$ neurons revealed unique non-RAS functions for the NF1 protein, neurofibromin. In this regard, NF1$^{+/1809}$ neurons exhibit elevated RAS activity, similar to neurons with NF1 mutations from patients who develop neurofibromas or optic gliomas. However, Nf1$^{+/1809}$ neurons do not exhibit increased action potential firing rates necessary to drive Nlgn3 and midkine (retinal ganglion cells) or COL1A2 (sensory neurons) secretion. These findings uncouple RAS regulation from the control of baseline neuronal excitability, and suggest that other non-RAS-dependent mechanisms account for these neurofibromin-regulated effects in neurons. While there are a few examples of non-RAS-dependent functions for neurofibromin, additional studies will be necessary to determine whether the NF1 Arg1809Cys mutation, located within the PH-like domain of neurofibromin, affects the conformation of the protein relative to neurofibromin dimerization, secondary structure, or associations with other neurofibromin-binding partners in neurons.

Fourth, it was demonstrated herein that NF1 mutation regulates neuronal hyperexcitability intrinsically through HCN channel function, and this hyperexcitability is evident in visual experience-evoked activation. The finding of hyperexcitability parallels prior studies of Nf1$^{+/neo}$ sensory neurons, which have greater numbers of action potentials, lower firing thresholds, lower rheobase currents, and shorter firing latencies. Herein, it was demonstrated that baseline NF1 regulation of neuronal hyperexcitability involves dysregulated HCN channel function (midkine, COL1A2 production). HCN channels are voltage-operated cation channels expressed in RGC and DRG neurons. Inhibition of HCN channel signaling with antagonists, such as ZD7288, increases neuron firing rates in vivo, paralleling the effects of HCN channel agonist (LTR) and antagonist (ZD7288) treatments on CNS and PNS neuron hyperexcitability and activity-dependent regulation of midkine and Col1a2 expression. Additionally, RGC hyperexcitability in the context of visual experience and consequent Adam10/Nlgn3 production are required for Nf1-OPG initiation, such that Nf1-optic glioma-prone mice do not develop tumors if reared in the dark during critical periods of tumorigenesis, or if Nlgn3 is genetically or pharmacologically blocked. As light-induced activity did not affect RGC midkine expression and Adam10/Nlgn3 production was not dependent on HCN channel function, Nf1-OPG initiation may rely on light-mediated RGC activation and Nlgn3 shedding, whereas OPG progression requires both Nlgn3 shedding and HCN channel-regulated baseline neuronal activity and midkine production.

Taken together, the findings reported herein advance the growing appreciation of neurons as active participants in tumor biology. While it was conclusively established that neuronal hyperexcitability drives mouse Nf1 OPG and pNF progression, future work using genetically engineered mouse strains and ectopic gene delivery methods may demonstrate that midkine and Col1a2 expression are solely sufficient to maintain murine OPG and pNF growth in vivo, respectively. Additional efforts will include the identification of key modulators of central and peripheral nervous system neuron-dependent tumorigenesis. This presents unique opportunities to repurpose FDA-approved compounds that target neuron-produced mitogens (e.g., collagenase) or HCN channels (e.g., Lamotrigine; Ivabradine) for the treatment of NF1-associated nervous system tumors, expanding the toolbox for targeting neuron-low-grade tumor interactions in cancer.

Methods

All experiments were performed in compliance with active Animal Studies Committee protocols at Washington University and UT Southwestern.

Mice.

All experiments were performed under active Animal Studies Committee protocols at Washington University School of Medicine (Washington University in St Louis Institutional Animal Care and Use Committee) and UT Southwestern (UT Southwestern Institutional Animal Care and Use Committee). According to these ethics committees, any animals with compromised motion/eating habits or an unhealthy appearance are euthanized. No animals were euthanized due to their tumor burden or as a result of the treatments performed in this study. Mice were maintained on a 12 light/dark cycle in a barrier facility, at 21° C. and 55% humidity, and had ad libitum access to food and water. Heterozygous Nf1 c.5425 C>T; Arg1809Cys mutant mice were generated by CRISPR/Cas9 engineering directly into C57Bl/6J embryos, resulting in mice with one wild-type Nf1 allele and one missense R1809C mutation. The mutation was confirmed by direct sequencing (IDT Technologies). R1809C Nf1-mutant mice, as well as heterozygous R681X and c.3827G>C43 Nf1-mutant mice were backcrossed to C57Bl/6J and wild-type littermates were used as controls. For pNF studies, mice were generated with the R1809C mutation or a neomycin cassette inserted in exon 3146 as the germline Nf1 allele and somatic Nf1 inactivation in Hoxb7-Cre cells78 (Nf1$^{flox/-}$; Hoxb7-Cre; Nf1$^{flox/1809}$; Hoxb7-Cre). In addition, conditional knockout Nf1$^{flox/flox}$; Hoxb7-Cre mice were used. Optic glioma-prone mice were generated with the R1809C mutation or a neomycin cassette inserted in exon 3146 as the germline Nf1 allele and somatic Nf1 inactivation in neuroglial progenitor cells (Nf1$^{f/1809}$; hGFAP-Cre or Nf1$^{f/neo}$; hGFAP-Cre mice). Littermate Nf1$^{flox/flox}$ mice were used as controls. For light/dark-rearing experiments, eight Nf1$^{+/neo}$ mice were reared in the dark for 4 weeks from 4 weeks of age. Eight littermate controls were reared in normal 12 h light/dark cycles. For in vivo lamotrigine treatment of NF1-pNFs, 8-week-old athymic nude mice (Charles River, Stock No. 490) underwent surgery to implant pNF progenitor cells. Mice of both sexes were randomly assigned to all experimental groups without bias, and the investigators were blinded until the final data analysis during all of the experiments.

Human-Induced Pluripotent Stem Cells and Neuronal Differentiation.

NF patient heterozygous germline NF1 gene (Transcript ID NM_000267) mutation were CRISPR/Cas9-engineered into a single commercially available male control human iPSC line (BJFF.6) by the Washington University Genome Engineering and iPSC Core Facility (GEiC). hiPSCs were authenticated based on morphology, as well as by immunocytochemical expression of pluripotency markers. Human iPSCs were differentiated into neural progenitor cells after 7 days of embryoid body formation (StemDiff Neural induction media; STEMCELL Technologies), followed by embryoid body dissociation and plating in PLO/Laminin-coated flasks in 50% DMEM/F12, 50% Neurobasal medium supplemented with N2, B27, 2 mM GlutaMAX (all Gibco), 10 ng/ml hLIF, 3 μM CHIR99021 and 2 μM SB431541 (all STEMCELL Technologies). NPCs were subsequently differentiated either into excitatory CNS neurons following incubation in neurobasal medium supplemented with B27, 2 mM glutamine, and 50 U/mL penicillin/streptomycin for a minimum of 2 weeks, or into GABAergic CNS neurons following incubation in neurobasal medium supplemented with 1 μM cAMP, 10 ng/mL BDNF, 10 ng/ml GDNF, and 10 ng/ml IGF147. For sensory neuron differentiation, iPSCs were incubated for 8 days in DMEM/F12 supplemented with LDN-193189, CHIR99021, A83-01, RO4929097, SU5402, retinoic acid, and 10% knockout serum replacement followed by 4 weeks of neurobasal medium supplemented with NT3, nerve growth factor, brain-derived neurotrophic factor, and glial-derived neurotrophic factor. No commonly misidentified cell lines were used in this study.

Spinal Cord Dissection and Optic Nerve Processing.

Mice were transcardially perfused at 3 months of age with Ringer's solution and 4% paraformaldehyde. Whole spinal cords were isolated following the removal of gross and muscle tissue and the breaking of vertebral column bones under a microdissection microscope. The entire spinal cord and peripheral nerves were rinsed and fixed in 10% formalin-buffered solution. DRG diameters were measured as previously reported and tumor volumes were calculated as volume=length×width$^2$×0.52, which approximates the volume of a spheroid. Optic nerves were isolated, imaged using a Leica DFC 3000 G camera, and their volumes were calculated as previously described. Using ImageJ, four diameter measurements were taken to estimate the thickness of each optic nerve beginning at the chiasm ($D_0$), at 150 ($D_{150}$), 300 ($D_{300}$), and 450 μm ($D_{450}$) anterior to the chiasm. The following equation was used to calculate the estimated optic nerve volume in each of the three sections, the sum of which was ultimately used to calculate the total optic nerve volume: $V_1 = \frac{1}{12} \pi h (D_0^2 + D_0 D_{150} + D_{150}^2)$.

Primary Hippocampal, RGC, and DRG Neuron Cell Culture.

Primary neuron cultures were generated from postnatal day 4-10 WT, Nf1$^{+/neo}$ or Nf1$^{+/1809}$ mice. Hippocampi were dissected in Hibernate-A (Gibco) and primary hippocampal neurons were established after papain dissociation, following the manufacturer's instructions (Worthington). Hippocampal neurons were grown for 7 days prior to analyses. Retinae were dissected in Hibernate-A (Gibco), dissociated in papain (Worthington) and ovomucoid inhibitor (Worthington) before being filtered withCD11b magnetic beads (Miltenyi Biotech) to deplete microglia. The remaining RGCs were plated on poly-D-lysine (Sigma)-coated plates and incubated in neurobasal media supplemented with N2, T3, transferrin, BSA, progesterone, putrescine, sodium selenite, L-glutamine, insulin, N-acetyl cysteine, and forskolin. RGC neurons were grown for 4 days prior to analyses. DRG tissues were isolated in HBSS (Gibco), dissociated in papain (Worthington biochemical) and collagenase type I (STEMCELL Technologies), prior to being strained (70 μm), plated in fibronectin (Fisher)-coated plates, and incubated in 10% fetal bovine serum in DMEM (Gibco). DRG neurons were grown for 7 days.

T Cell and Microglia Isolation.

Four to six-week-old WT and Nf1$^{+/1809}$ mouse spleens were homogenized into single-cell suspensions by digestion in PBS containing 0.1% BSA and 0.6% sodium citrate. The homogenates were subsequently washed and incubated with 120 Kunitz units of DNase I for 15 min following red blood cell lysis (eBioscience). Cells were then filtered through a 30 μM cell strainer to obtain a single-cell suspension. T cells were maintained at 2.5×106 cells ml$^{-1}$ in RPMI-1640 medium supplemented with 10% FBS and 1% penicillin/streptomycin. T cells were treated with 100 ng/μL midkine (R&D Systems) for 48 h. Microglia isolation was performed on 4-6-week-old WT and Nf1$^{+/1809}$ mouse brains using the multi-tissue dissociation kit (Miltenyi Biochemicals) following published protocols. The resulting cells, microglia attached to a monolayer of astrocytes, were maintained in minimal essential medium supplemented with 1 mM L-glutamine, 1 mM sodium pyruvate, 0.6% D-(+)-glucose, 1 ng/ml GM-CSF, 100 µg/ml P/S, and 10% FBS. From 11 days in vitro onwards, the cells were incubated in medium without GM-CSF and at 13 days in vitro, the cells were treated with 6000 pg/mL of recombinant Ccl4 (R&D Systems) for 24 h. At 14 days in vitro, the microglia were mechanically dissociated from the astrocyte layer by gentle shaking (200 g, 5 h, 37° C.). T-cell and microglia conditioned media were collected for subsequent ELISA experiments, both from control and treated cells following 22 µM filtration.

shNF1 Schwann Cell and Nf1$^{-/-}$ DRG-NSC Cultures.

Normal human Schwann cells (Sciencell) were incubated in SCM (Sciencell) on PDL-coated plates following the manufacturer's instructions and were infected with shNF1 1-3 lentiviral particles (Sigma; 39714, 39715, 39717). NF1 knockdown was confirmed by western blotting. Nf1$^{flox/flox}$; Cre (Nf1$^{-/-}$) DRG dorsal nerve root sphere cells (DRG-NSCs) were isolated from E13.5 embryo DRG/nerve roots, and were infected with Ad-CMV-Cre. DRG-NSCs were incubated in DMEM supplemented with heparin, glucose, HEPES, L-glutamine, N2, B27, sodium carbonate, EGF and bFGF in ultralow cell attachment flasks, or fibronectin-coated flasks for 2D cell proliferation assays.

Sensory Neuron Conditioned Media Protein Analysis and Validation of Candidate Proteins.

Control, NF1$^{+/R1809C}$ or NF1$^{+/R681X}$ sensory neurons were washed with PBS and were incubated with artificial cerebral spinal fluid (aCSF) for 24 h prior to collecting conditioned media (CM). The media was treated with protease inhibitors (Cell Signaling Technologies), was snap frozen, and sent to Applied Biomics for 2D gel electrophoresis analysis. The conditioned media was run on a 2D electrophoresis gel and the proteins were separated by size and pH, as per the vendor's specifications. The resulting digital images of the 2D gels of CTL, NF1$^{+/R681X}$ and NF1$^{+/R1809C}$ conditioned media (see e.g., FIG. 35A) were digitally superimposed pairwise by Applied Biomics (CTL vs NF1$^{+/R681X}$ and CTL vs NF1$^{+/R1809C}$) in order to detect differentially expressed proteins between each of the NF1-mutant neurons and the controls. In total, 176 dots (proteins) were upregulated or downregulated more than 1.5-fold relative to the CTL conditioned media, each dot was assigned a random identification number, and the intensity of the relative expression of each protein was translated into numerical values by the vendor. From the 176 differentially regulated proteins, only six (circled in blue; see e.g., FIG. 32C) were upregulated more than 1.5-fold in NF1$^{+/R681X}$ but not NF1$^{+/R1809C}$ relative to CTL sensory neuron CM. As such, the identity of these six proteins alone was determined by mass spectrometry by Applied Biomics, following vendor specifications (Sourcedata). No large-scale mass spectrometry or raw proteomics data was generated for these analyses. The concentration of each of these six identified proteins was assayed in independently generated CTL and NF1-mutant Schwann cell growth-promoting (NF1$^{C383X}$, NF1$^{R681X}$, NF1$^{E2207X}$) and NF1-mutant non-Schwann cell growth-promoting (NF1$^{R1809C}$) sensory neurons (see e.g., FIG. 34 and FIG. 37A-FIG. 37E) conditioned media by respective ELISA assays.

Small-Molecule Treatments.

A subset of mouse and human CNS and PNS neurons were treated with tetrodotoxin (TTX; 1 µM), pan-RAS inhibitor IN-1 (1 µM), lamotrigine (LTR; 200 µM), or ZD7288 (ZD; 30 µM) for 3 min prior to collection of cells or conditioned media. A subset of shNF1 SCs and Nf1$^{-/-}$ DRG NSCs were treated with collagenase (0.001 U/mL), human COL1A2 (12.5 pg/mL), or mouse Col1a2 (12.5 pg/mL) for 24 h.

Multi-Electrode Array (MEA) Recordings and Analyses.

Primary hippocampal (300,000 cells/well), RGC (300, 000 cells/well), or DRG neurons (150,000 cells/well) from each of the strains assayed (WT, Nf1$^{+/neo}$, Nf1$^{+/1809}$) were plated on AXION Biosystems 48-well MEA plates and grown for 10 days in their respective optimal growth media. Each well included neurons from a single mouse. A minimum of six individual mice originating from a minimum of three independent litters were analyzed. Neurons isolated from each animal were plated in a minimum of triplicate technical replicate wells of the MEA plate. For experiments involving pharmacological treatments, neurons isolated from each Nf1$^{+/neo}$ mouse were plated in a minimum of six individual wells, with a minimum of three wells serving as the vehicle-treated controls and a minimum of three wells as the treated cohort.

All efforts were taken to ensure even spreading of the neurons throughout each well. Not all 16 electrodes present within each well were within the optimal proximity to neurons and as such not all electrodes detected action potentials (APs). To account for this variation, all metrics were normalized to the number of the active electrodes only. In addition, as the number of active electrodes/well varied between technical replicates of each animal, the AP firing rate of all the replicate wells of each animal was averaged. As such, each data point graphed represents the average of all technical replicates for each given animal. All neurons were recorded for 3 min at a 4.5 standard deviation threshold level and 5000 Hz as a digital filter using AXION Biosystems integrated studio (AxIS) version 2.5.1 software. AP firing rates were calculated from the total number of APs/3 min and are represented as APs/min, only accounting for active electrodes. Representative traces of action potentials were extracted using the AXION Biosystems neural metric tool and Offline sorter x64 version 4 software.

Calcium Imaging of Neurons.

Primary RGC (150,000 neurons/well) or DRG (75,000 neurons/well) neurons were plated onto poly-D-lysine and laminin-coated 96-well plates for 10 days. At 10 days, the cells were treated with Fluo-8/AM (1345980-40-6, AAT Bioquest), PowerLoad (P10020, ThermoFisher) and Probenecid (P36400; ThermoFisher) for 30 min at 37° C. and for another 30 min at room temperature. The neurons were subsequently washed with HBSS and incubated for a minimum of 10 min in fresh culture medium supplemented with 5% neurobackground suppressor (F10489; ThermoFisher). The neurons were imaged on a Nikon spinning disk upright epi-fluorescence confocal microscope equipped with a ×10 dry objective, and a 488 nm wavelength laser was used for wide-field imaging. The neurons were stimulated by a Ti LAPP DMD (Deformable Mirror Device) LED source for ultrafast photo-stimulation, with 0.1 mW applied during each recording for Fluo-8 excitation. Fluo-8 images were collected at 15 Hz (2048×2048 pixels, 1×1 mm) and the duration of each region of interest (ROI) was limited to 10 min. The fluorescence intensity and optical response to depolarizing membrane potential transients (ΔF/F) were calculated in Matlab programming environment to generate single-neuron activity traces. The ΔF/F threshold was set at 4 standard deviation beyond baseline fluorescence. Following data acquisition, the duration and shape of each AP spike were compared by merging all the spikes in the same time window. Neurons from each animal were seeded in six wells and a minimum of three neurons were recorded per well. Data recorded from a minimum of 18 neurons per animal were averaged. Each data point represents a single animal.
Immunohistochemistry and Immunocytochemistry.

All spinal cord and optic nerve fixed tissues as well as human brain tissue, lymph nodes, normal sural nerve, cutaneous neurofibromas or plexiform neurofibromas, and mouse sciatic nerve, cutaneous or plexiform neurofibromas were paraffin-embedded, serially sectioned (5 μm) and immunostained with GFAP, Iba1, Ki67, CD3, Midkine, GAP43, CD34, Factor XIIIa, SOX10, neurofilament-200, and Col1a2 (see e.g., TABLE 1).

TABLE 1

Antibodies used.

| Antibody | Dilution | Validation (application) | Manufacturer | Catalog# Number |
|---|---|---|---|---|
| Alexa Fluor 488 goat anti-mouse secondary antibody | 1:200 | Fisher Scientific (IF/ICC) | Fisher Scientific | A11029 |
| Alexa Fluor 568 goat anti-rabbit secondary antibody | 1:200 | Fisher Scientific (IF/ICC) | Fisher Scientific | A11011 |
| Anti-actin | 1:5,000 | CST (WB) | Cell Signaling Technologies | 4970 |
| Anti-alpha-tubulin | 1:5,000 | Sigma-Aldrich (WB) | Sigma Aldrich | T9026 |
| Anti-beta III Tubulin antibody [2G10] | 1:1,000 | Abcam (WB, ICC) | Abcam | ab78078 |
| Anti-BRN3A, Rabbit monoclonal [EPR23257-285] | 1:1,000 | Abcam (IHC, WB) | Abcam | ab245230 |
| Anti-CD3 antibody | 1:50 | Abcam (IHC) | Abcam | ab11089 |
| Anti-CD34 | 1:2,500 | Abcam (IHC) | Abcam | ab81289 |
| Anti-CGRP (CALCA) | 1:500 | Abcam (WB) | Abcam | ab189786 |
| Anti-Col1a2 (for mouse samples) | 1:200 | ThermoFisher (IHC) | ThermoFisher | PA5-106555 |
| Anti-COL1A2 antibody (for human samples) | 1:200 | Abcam (ICC) | Abcam | ab96723 |
| Anti-EGR2 | 1:100 | Abcam (ICC) | Abcam | ab156765 |
| Anti-Factor XIIIa | 1:100 | Abcam (IHC) | Abcam | ab1834 |
| Anti-GABA | 1:1,000 | Sigma (ICC) | Sigma Aldrich | A2052 |
| Anti-GAD2, Rabbit monoclonal [D5G2] | 1:500 | CST (IF) | Cell Signaling Technologies | 5843S |
| Anti-GAP43 | 1:2000 | Abcam (IHC) | Abcam | ab12274 |
| Anti-GFAP, Rat monoclonal [2.2B10] | 1:500 | ThermoFisher (IHC, ICC, IF) | ThermoFisher | 13-0300 |
| Anti-Glutamate synthetase mouse monoclonal [3B6] | 1:500 | Abcam (ICC) | Abcam | ab64613 |
| Anti-Glutamate synthetase rabbit polyclonal | 1:500 | Abcam (ICC) | Abcam | ab228590 |
| Anti-Iba1 | 1:500 | Wako (IHC) | Wako | NC9288364 |
| Anti-ISL-1 Rabbit monoclonal [EP4182] | 1:250 | Abcam (ICC) | Abcam | ab109517 |
| anti-Ki-67, Mouse monoclonal [B56] | 1:500 | BD Biosciences (ICC), (1) | BD Biosciences | BDB556003 |

TABLE 1-continued

Antibodies used.

| Antibody | Dilution | Validation (application) | Manufacturer | Catalog# Number |
|---|---|---|---|---|
| Anti-Midkine C-terminal | 1:200 | Abcam (IHC/IF), (2) | Abcam | ab170820 |
| Anti-Mouse IgG Polyclonal Secondary Antibody IRDye ® 800RD | 1:5,000 | Li-Cor Biosciences (WB) | Li-Cor Biosciences | 926-32210 |
| Anti-Nestin | 1:200 | Abcam (ICC) | Abcam | ab92391 |
| Anti-NeuN mouse monoclonal [A60] | 1:500 | Sigma-Aldrich (ICC) | Sigma-Aldrich | MAB377 |
| Anti-Neurofilament H (NF-H) Non-phosphorylated Antibody mouse monoclonal SMI32 | 1:500 | Biolegend (WB, IF) | Biolegend | 801701 |
| Anti-neuroligin-3 | 0.4 µg/mL | Novus (WB), (1) | Novus | NBP1-90080 |
| Anti-OCT6 | 1:200 | Abcam (ICC) | Abcam | ab272925 |
| Anti-p75 NTR rabbit monoclonal [D4B3] | 1:1000 | CST (ICC) | Cell Signaling Technologies | 8238S |
| Anti-peripherin | 1:500 | Abcam (ICC) | Abcam | ab4666 |
| Anti-Rabbit IgG Polyclonal Secondary Antibody IRDye ® 680RD | 1:5,000 | Li-Cor Biosciences (WB) | Li-Cor Biosciences | 926-68071 |
| Anti-Rbpms | 1:1,000 | Phospho Solutions (ICC/IF) | Phospho Solutions | 1832-RBPMS |
| Anti-S100β antibody, Rabbit monoclonal [EP15/6Y] | 1:100 | Abcam (ICC) | Abcam | ab52642 |
| Anti-SOX10 antibody, Rabbit monoclonal [EPR4007-104] (for mouse tumors) | 1:250 | Abcam (IHC), (3) | Abcam | ab180862 |
| Anti-SOX10, Rabbit monoclonal [SP267] (for human cells) | 1:50 | Abcam (ICC) | Abcam | ab227680 |
| Biotinylated anti Mouse secondary antibody | 1:200 | Fisher (IHC) | Vector Laboratories | BA9200 |
| Biotinylated anti Rabbit secondary antibody | 1:200 | Fisher (IHC) | Vector Laboratories | BA-1000 |

WB, Western blot;
IHC, immunohistochemistry;
IF, immunofluorescence;
ICC, immunocytochemistry Immunohistochemical staining was performed using the Vectastain ABC kit (Vector Laboratories) and appropriate biotinylated secondary antibodies (Vector Laboratories). Hematoxylin and eosin (H&E) staining was performed following the manufacturer's instructions (StatLab). Primary RGCs, hippocampal neurons, DRG neurons, shNF1 Schwann cells, and hiPSC-sensory neurons were immunostained with appropriate primary (RGCs: Rbpms, Tuj-1; hippocampal neurons: GAD65, Glutamine synthetase, Tuj-1; DRG neurons: Peripherin, ISL1, Tuj-1; SCs: EGR2, S100β, OCT6, SOX10; sensory neurons: peripherin, BRN3A, SMI32, ISL1, p75NTR, Nestin, Tuj-1) and secondary Alexa-fluor-conjugated antibodies (see e.g., TABLE 1). Images were acquired using Image Studio Lite Version 5.2 software, and LAS AF Lite 3.2.0 software and analyzed using ImageJ 1.53a software, as well as Adobe Photoshop version 21.1.1.

RAS, Midkine, COL1A2, Ccl4, Ccl5 ELISA Assays.

RAS activity (ThermoFisher), COL1A2 (Fisher Scientific,), Ccl4 (R&D Systems), Ccl5 (Fisher), and Midkine (mouse; LSBio; human; Abcam) ELISAs were performed on homogenized cell pellets (RAS-GTP) or filtered (0.22 μm) conditioned media (COL1A2, Ccl4, Ccl5, Midkine) following the manufacturer's instructions. Each assay was performed using a minimum of four independently generated biological replicates. Data from all of these colorimetric assays were collected on a Bio-Rad iMark microplate reader and analyzed using MPM6 v6.3 (Bio-Rad Laboratories) software.

Western Blotting.

Western blotting was performed on snap-frozen cells and tissues. Samples were lysed in RIPA buffer (Fisher) supplemented with a protease inhibitor cocktail (Cell Signaling) and were blotted using appropriate primary (s-Nlgn3, neurofilament-200, peripherin, BRN3A, ISL1, CALCA, α-tubulin, β-actin; see e.g., TABLE 1) and NIR-conjugated secondary antibodies (Licor). Images were captured and analyzed using the Li-Cor Image Studio Lite Version 5.2 software and are representative of more than three independently generated biological replicates.

Quantitative Real-Time PCR.

Total RNA was extracted following the manufacturer's instructions (QIAGEN) and reverse-transcribed using a high-capacity cDNA reverse transcription kit (Applied Biosystems) qPCR was performed using TaqMan gene expression assays (Mdk, Col1a2, COL1A2, Nlgn3, Adam10, NLGN3, ADAM10, Hcn1-4; Supplementary Table 2) and TaqMan Fast Advanced Master Mix (Applied Biosystems) according to the manufacturer's instructions. All reactions were performed using the Bio-Rad CFX96 Real-Time PCR system equipped with Bio-Rad CFX Manager 3.1 software. Gene expression levels of technical replicates were estimated by ΔΔCt method using GAPDH or Gapdh (see e.g., TABLE 2) as reference genes.

TABLE 2

Oligonucleotides used for quantitative real-time PCR

| Oligonucleotides | Manufacturer | Catalog Number |
| --- | --- | --- |
| ADAM10-TaqMan ® Gene Expression Assay FAM-MGB | ThermoFisher | Hs01109562_m1 |
| Adam10 - TaqMan ® Gene Expression Assay FAM-MGB | ThermoFisher | Mm00545742_m1 |
| COL1A2 - TaqMan ® Gene Expression Assay FAM-MGB | ThermoFisher | Hs01028940_g1 |
| Col1a2 - TaqMan ® Gene Expression Assay FAM-MGB | ThermoFisher | Mm00483888_m1 |
| GAPDH - TaqMan ® Gene Expression Assay FAM-MGB | ThermoFisher | Hs02786624_g1 |
| Gapdh - TaqMan ® Gene Expression Assay FAM-MGB | ThermoFisher | Mm99999915_g1 |
| Hcn1 - TaqMan ® Gene Expression Assay FAM-MGB | ThermoFisher | Mm00468832_m1 |
| Hcn2 - TaqMan ® Gene Expression Assay FAM-MGB | ThermoFisher | Mm00468538_m1 |
| Hcn3 - TaqMan ® Gene Expression Assay FAM-MGB | ThermoFisher | Mm01212852_m1 |
| Hcn4 - TaqMan ® Gene Expression Assay FAM-MGB | ThermoFisher | Mm01176084_m1 |
| Mdk - TaqMan ® Gene Expression Assay FAM-MGB | ThermoFisher | Mm00440279_m1 |
| NLGN3 - TaqMan ® Gene Expression Assay FAM-MGB | ThermoFisher | Hs01043809_m1 |
| Nlgn3 - TaqMan ® Gene Expression Assay FAM-MGB | ThermoFisher | Mm01225951_m1 |

In Vivo Mouse Lovastatin and Lamotrigine Treatments.

In total, 17 Nf1$^{flox/neo}$; GFAP-Cre (Nf1-OPG) mice were intraperitoneally administered vehicle (saline in 1% methylcellulose; n=9) or 25 mg/Kg body weight lamotrigine (Selleckchem; n=8) from four to six weeks of age, three times a week. The mice were then aged to 12 weeks for optic nerve and RGC analysis. For lovastatin treatments, 20 Nf1-OPG mice were administered with 25 mg/kg/day lovastatin (Santa Cruz Biotechnologies; n=10) or vehicle (saline in 1% methylcellulose; n=10) intraperitoneally for 4 weeks, 3 days a week, beginning at 4 weeks of age. The mice were analyzed at 12 weeks of age. A separate cohort of animals was administered with 25 mg/kg/day lovastatin (Santa Cruz Biotechnologies; n=10) or vehicle (saline in 1% methylcellulose; n=10) intraperitoneally for 4 weeks, 3 days a week, beginning at 4 weeks of age. These mice were analyzed at 24 weeks of age. A third cohort of animals was administered with 10 mg/kg/day lovastatin (Santa Cruz Biotechnologies; n=10) or vehicle (saline in 1% methylcellulose; n=10) by oral gavage for 4 weeks, 5 days a week, beginning at 4 weeks of age. These mice were analyzed at 12 weeks of age. For pNF analyses, Nf1$^{-/-}$ DRG-NSCs were implanted in sciatic nerves of 8-week-old athymic nude mice as previously described. Briefly, the mice underwent surgery to create a pocket by displacing the quadriceps muscle and exposing their sciatic nerve. In all, 1×10$^6$ Nf1$^{-/-}$ DRG-NSCs were implanted in the pocket around the sciatic nerve, such that the cells could be in direct contact with the nerve before the muscle and skin were sutured. Following recovery from the surgery, the mice were intraperitoneally administered vehicle (saline in 1% methylcellulose; n=5) or 25 mg/kg body weight lamotrigine (Selleckchem; n=5) three times a week for 6 weeks prior to histological analysis.

Published RNA Database Analysis.

The analysis for this paper was generated using Partek Flow software, version 10.0 using publicly available datasets (GEO: GSE14038; see e.g., TABLE 3).

TABLE 3

Available microarray datasets used for COL1A2 analysis.

| Sample | Sample name | GSM352--- |
|---|---|---|
| normal SCs | batch1c-NHSC_303_HG_U133_Plus_2.CEL | 487 |
| normal SCs | batch1c-NHSC_339_HG_U133_Plus_2.CEL | 489 |
| normal SCs | batch1c-NHSC_771_HG_U133_Plus_2.CEL | 490 |
| normal SCs | batch2a-NHSC216_HG_U133_Plus_2.CEL | 501 |
| normal SCs | batch2b-NHSC323_HG_U133_Plus_2.CEL | 515 |
| normal SCs | batch2c-NHSC338_HG_U133_Plus_2.CEL | 526 |
| normal SCs | batch3a-NHSC_286_HG_U133_Plus_2.CEL | 535 |
| normal SCs | batch3b-NHSC_J017_HG_U133_Plus_2.CEL | 543 |
| normal SCs | batch3c-NHSC_02.8_HG_U13Plus_2.CEL | 550 |
| normal SCs | batch3c-NHSC_J037_HG_U13Plus_2.CEL | 551 |
| cNF | batch3a-dNFSC_ERS_HG_U133_Plus_2.CEL | 534 |
| cNF | batch3b-dNFSC_ABB_HG_U133_Plus_2.CEL | 542 |
| cNF | batch3c-dNFSC_JLM_HG_U13Plus_2.CEL | 549 |
| cNF | batch1c-ABC_8N_-I-_HG_U133_Plus_2.CEL | 479 |
| cNF | batch1c-AIBC_2N_-I-_HG_U133_Plus_2.CEL | 480 |
| cNF | batch1c-CLT_6N_+I-_HG_U133_Plus_2.CEL | 481 |
| cNF | batch1c-MGF_33N_+I-_HG_U133_Plus_2.CEL | 483 |
| cNF | batch1c-SCC_7N_-I-_HG_U133_Plus_2.CEL | 492 |
| cNF | batch2a-ADN1N_KO_HG_U133_Plus_2.CEL | 495 |
| cNF | batch2b-RMN9N_KO_HG_U133_Plus_2.CEL | 520 |
| cNF | batch2c-SCC5N_KO_HG_U133_Plus_2.CEL | 531 |
| pNF | batch3a-pNFSC_04.7_HG_U133_Plus_2.CEL | 537 |
| pNF | batch3a-pNFSC_05.4_HG_U133_Plus_2.CEL | 538 |
| pNF | batch3b-pNFSC_00.13_HG_U133_Plus_2.CEL | 544 |
| pNF | batch3b-pNFSC_05.5_HG_U133_Plus_2.CEL | 545 |
| pNF | batch3c-pNFSC_97.9_HG_U13Plus_2.CEL | 552 |
| pNF | batch1b-pNF00.6_HG_U133_Plus_2.CEL | 464 |
| pNF | batch1b-pNF95.3_HG_U133_Plus_2.CEL | 466 |
| pNF | batch1b-pNF95.6_HG_U133_Plus_2.CEL | 467 |
| pNF | batch2a-pNF03.3_HG_U133_Plus_2.CEL | 503 |
| pNF | batch2b-pNF04.4_HG_U133_Plus_2.CEL | 516 |
| pNF | batch2c-pNF05.3_HG_U133_Plus_2.CEL | 527 |

RNA-seq reads were aligned to the Ensembl release 100 top-level assembly with STAR version 2.7.8a. Gene counts and isoform expression were derived from Ensembl output. Sequencing performance was assessed for the total number of aligned reads, total number of uniquely aligned reads, and features detected. Normalization size factors were calculated for all gene counts by CPM to adjust for differences in sequencing depth. Genes not expressed on average with greater than two count-per-million were excluded from further analysis. Gene-specific analysis was then performed using the lognormal with shrinkage model (limma-trend method) to analyze for expression differences between conditions.

Short Hairpin Constructs, Lentiviral Production, and Neuronal Infection.

Human shCOL1A2 and mouse shCol1a2 lentiviral particles (TRCN0000090043; TRCN0000090045; TRCN0000335210) were generated as previously described61. NF1$^{+/R681X}$ or Nf1$^{+/neo}$ sensory neurons were infected with three independent shCOL1A2 lentiviral particles or shRNA scrambled control particles (sc-108080; Santa Cruz Biotechnology) for 24 h. Neuronal media was refreshed and conditioned media was collected for subsequent assays 48-72 h post infection.

Quantification and Statistical Analysis.

All statistical tests were performed using GraphPad Prism software (versions v5, v_8.2.1, and v_9.3.1). Paired or unpaired two-tailed Student's t tests or one-way analysis of variance (ANOVA) with Tukey's, Dunnett's, or Bonferroni post-test correction using GraphPad Prism 5 software. Statistical significance was set at $P<0.05$, and individual p values are indicated within each graphical figure. A minimum of three independently generated biological replicates was employed for each of the analyses. Numbers (n) are noted for each individual analysis.

Example 2: Rufinamide Reduces Midkine Production and Excitability in Neurons

Figure 47:
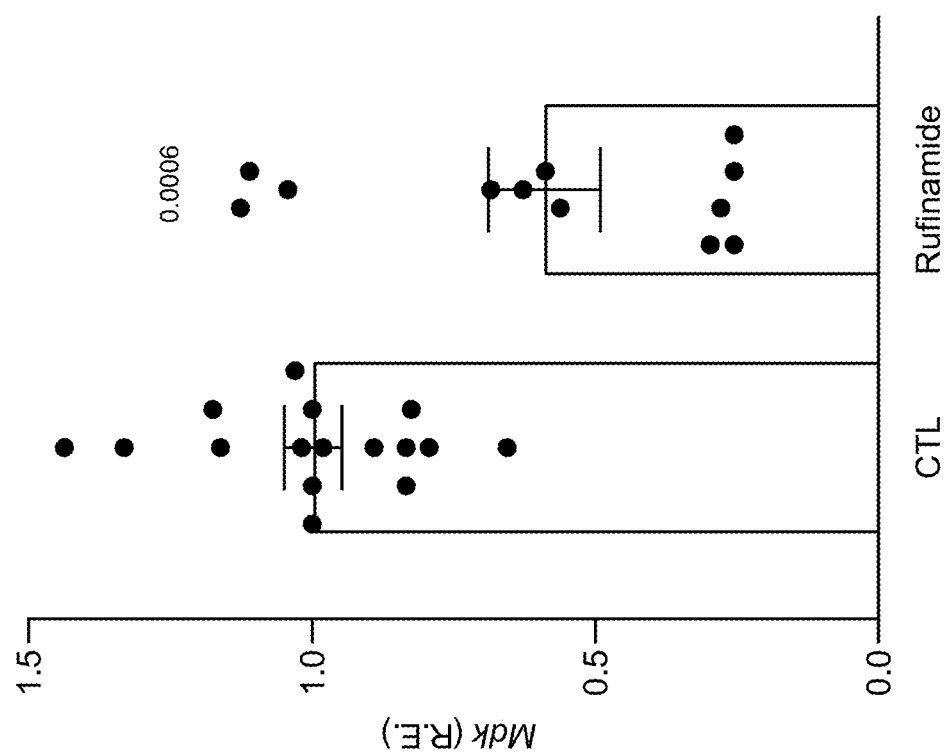
FIG. 47 is a bar graph showing rufinamide reduces Nf1-mutant neuronal Mdk (Midkine transcript) levels in accordance with the present disclosure.
Figure 48:
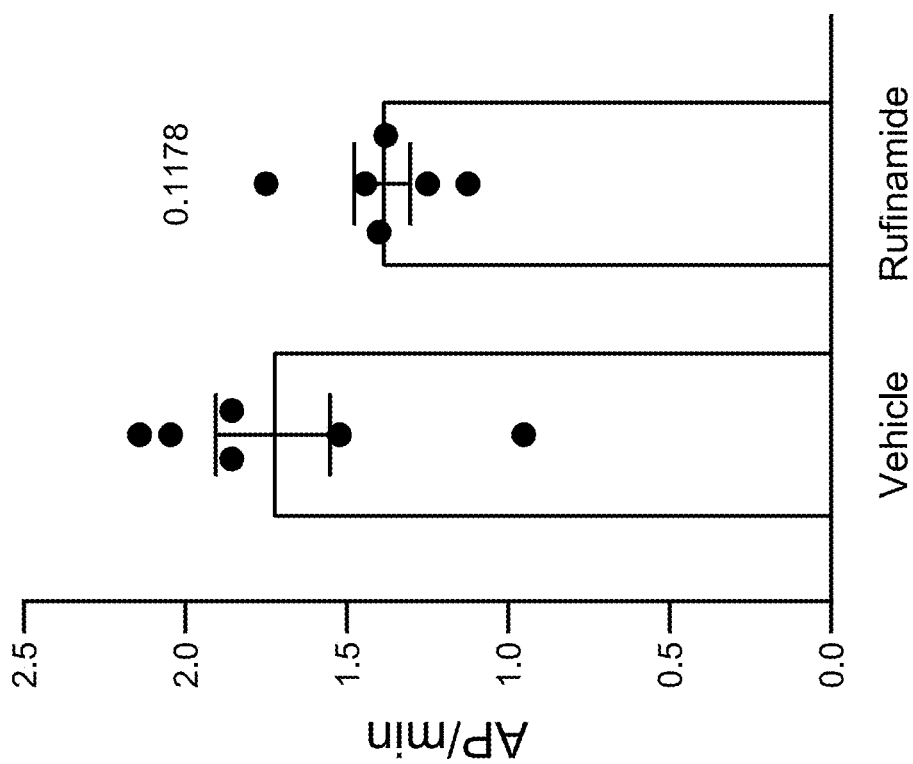
FIG. 48 is a bar graph showing rufinamide reduces Nf1-mutant neuronal excitability in accordance with the present disclosure.

Nf1-mutant neurons were treated with the antiepileptic drug rufinamide. Treatment with rufinamide reduced Midkine expression (see e.g., FIG. 47) and neuronal excitability (see e.g., FIG. 48).

What is claimed is:

1. A method of inhibiting tumor growth in a subject in need thereof, the method comprising:
   administering a therapeutically effective amount of a hyperpolarization-activated cyclic nucleotide-gated (HCN) channel agonist comprising at least one of lamotrigine and rufinamide to the subject;
   wherein the subject has Neurofibromatosis type 1 (NF1); and
   wherein the subject has a nervous system tumor.

2. The method of claim 1, wherein the subject has an NF1 gene mutation selected from c.1149 C>A, p.Cys381X; c.2041 C>T, pArg681X; or c.6619 C>T, p.Gln2207X.

3. The method of claim 1, wherein the nervous system tumor is a glioma, an optic pathway glioma (OPG), a peripheral nerve sheath tumor, or a neurofibroma.

4. The method of claim 1, wherein administering the HCN channel agonist to the subject reduces neuronal excitability, paracrine factor production or secretion, or Schwann cell proliferation in the subject.

5. The method of claim 4, wherein the HCN channel agonist reduces excitability or paracrine factor production of retinal ganglion cells (RGCs), sensory neurons, or dorsal root ganglion cells (DRGs).

6. The method of claim 1, wherein administering the HCN channel agonist to the subject reduces Nlgn3, midkine, or Col1a2 transcript or protein expression or secretion in the subject.

7. The method of claim 1, further comprising administering an effective amount of a COL1A2 inhibitor to the subject.

8. The method of claim 7, wherein the COL1A2 inhibitor is collagenase.

* * * * *